US007153650B2

(12) United States Patent
Stanton et al.

(10) Patent No.: US 7,153,650 B2
(45) Date of Patent: Dec. 26, 2006

(54) MARKER SYSTEM FOR PREPARING AND CHARACTERIZING HIGH-QUALITY HUMAN EMBRYONIC STEM CELLS

(75) Inventors: Lawrence W. Stanton, Singapore (SG); Ralph Brandenberger, Menlo Park, CA (US); Joseph D. Gold, San Francisco, CA (US); John M. Irving, San Mateo, CA (US); Ramkumar Mandalam, Union City, CA (US); Michael Mok, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 508 days.

(21) Appl. No.: 10/389,431

(22) Filed: Mar. 13, 2003

(65) Prior Publication Data

US 2004/0180347 A1    Sep. 16, 2004

(51) Int. Cl.
  *C12Q 1/00*   (2006.01)
  *C12Q 1/68*   (2006.01)
  *G01N 33/53*  (2006.01)
  *C12N 5/00*   (2006.01)
  *C12N 5/02*   (2006.01)
(52) U.S. Cl. .................... 435/4; 435/6; 435/7.1
(58) Field of Classification Search ............... None
  See application file for complete search history.

(56) References Cited

U.S. PATENT DOCUMENTS

| 5,256,643 A | 10/1993 | Persico et al. ................ 514/12 |
| 5,264,557 A | 11/1993 | Salomon et al. ............. 530/399 |
| 5,620,866 A | 4/1997 | Salomon et al. ........... 435/69.1 |
| 5,650,285 A | 7/1997 | Salomon et al. ............. 435/7.1 |
| 5,654,140 A | 8/1997 | Persico et al. ................. 435/6 |
| 5,856,136 A | 1/1999 | Au-Young ................ 435/69.3 |
| 6,090,622 A | 7/2000 | Gearhart et al. ............ 435/366 |
| 6,200,806 B1 | 3/2001 | Thomson ..................... 435/366 |
| 2002/0146678 A1 | 10/2002 | Benvenisty ..................... 435/4 |
| 2005/0095708 A1* | 5/2005 | Pera et al. .................. 435/369 |

FOREIGN PATENT DOCUMENTS

| AU | 764684 | 5/2000 |
| JP | 1271145 | 1/2003 |
| WO | WO 99/20741 | 4/1999 |
| WO | WO 00/46355 | 8/2000 |
| WO | WO 01/51610 | 7/2001 |
| WO | WO 01/51616 | 7/2001 |
| WO | WO 01/81549 | 11/2001 |
| WO | WO 01/88104 | 11/2001 |
| WO | WO 02/42445 | 5/2002 |
| WO | WO 02/42468 | 5/2002 |
| WO | WO 03/020920 | 3/2003 |
| WO | WO 2004/009758 | 1/2004 |

OTHER PUBLICATIONS

Carroll et al. Aberrant expression of gastrin-releasing peptide and its receptor by well-differentiated colon cancers in humans. Am. J. Physiol. 276 (Gastrointest. Liver Physiol. 39):G655-G665, 1999.*
Abdel-Rahman B et al, Expression of Transcription Regulating Genes in Human Preimplantation Embryos, Hum Reprod 10(10):2787 (1995).
Adamson Ed et al, Cripto: A Tumor Growth Factor and More, J Cell Physiol 190:267 (2002).
Adjaye J et al, cDNA Libraries from Single Human Preimplantation Embryos, Genomics 46:337 (1997).
Amit M et al, Clonally Derived Human Embryonic Stem Cell Lines Maintain Pluripotency and Proliferative Potential for Prolonged Periods of Culture, Dev Biol 227:271 (2000).
Draper JS et al, Surface Antigens of Human Embryonic Stem Cells: Changes Upon Differentiation in Culture, J Anat 200:249 (2002).
Eisen MB et al, Cluster Analysis and Display of Genome-Wide Expression Patterns, PNAS 95:14863 (Dec. 1998).
Fan Y et al, Forced Expression of the Homeobox-Containing Gene *Pem* Blocks Differentiation of Embryonic Stem Cells, Dev Biol 210:481 (1999).
Forrester LM et al, An Induction Gene Trap Screen in Embryonic Stem Cells: Identification of Genes that Respond to Retinoic Acid *in Vitro*, PNAS 93:1677 (Feb. 1996).
Gajović S et al, Genes Expressed After Retinoic Acid-Mediated Differentiation of Embryoid Bodies are Likely to be Expressed During Embryo Development, Exp Cell Res 242:138 (1998).
Gossier A et al, Mouse Embryonic Stem Cells and Reporter Constructs to Detect Developmentally Regulated Genes, Science 244:463 (Apr. 1989).
Henderson JK et al, Preimplantation Human Embryos and Embryonic Stem Cells Show Comparable Expression of Stage-Specific Embryonic Antigens, Stem Cells 20:329 (2002).
Hicks GG et al, Functional Genomics in Mice by Tagged Sequence Mutagenesis, Nat Gen 16:338 (Aug. 1997).
Höllrigl A et al, High-Throughput Site-Directed Mutagenesis in ES Cells, Biochem Biophys Res Commun 289:329 (2001).
Jackson M et al, Cloning and Characterization of *Ehox*, a Novel Homeobox Gene Essential for Embryonic Stem Cell Differentiation, J Biol Chem 277(41):38683 (Oct. 2002).

(Continued)

*Primary Examiner*—Quang Nguyen
(74) *Attorney, Agent, or Firm*—Bart W. Wise; J. Michael Schiff

(57) ABSTRACT

This disclosure provides a system for qualifying embryonic stem cells intended for human therapy. A large-scale sequencing project has identified important markers that are characteristic of undifferentiated pluripotent cells. Combinations of these markers can be used to validate the self-renewing capacity of ES cells, and their ability to differentiate into tissue types suitable for regenerative medicine. The marker system of this invention has been used to screen feeder cells, media additives, and culture conditions that promote proliferation of stem cells without differentiation. A culture system optimized by following these markers is suitable for rapid expansion of undifferentiated cells from existing lines, or the derivation of new lines that are equally apposite for clinical use.

6 Claims, 6 Drawing Sheets

OTHER PUBLICATIONS

Figure 1:
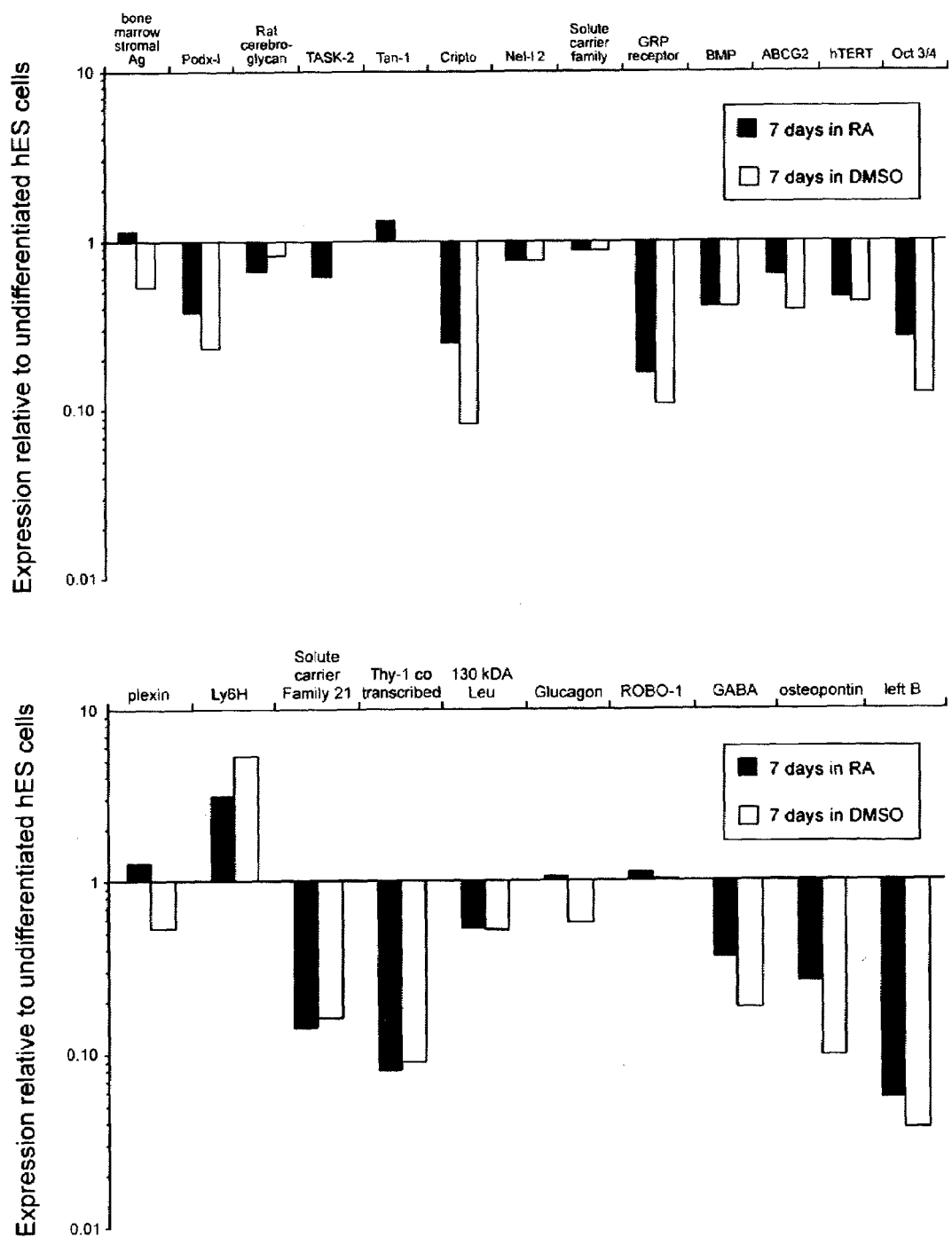

Kelly DL et al, DNA Microarray Analyses of Genes Regulated During the Differentiation of Embryonic Stem Cells, Mol Reprod Dev 56:113 (2000).

Lawinger P et al, Lack of Enhancer Function in Mammals is Unique to Oocytes and Fertilized Eggs, J Bio Chem 274(12):8002 (Mar. 1999).

Leahy A et al, Use of Developmental Marker Genes to Define Temporal and Spatial Patterns of Differentiation During Embryoid Body Formation, J Exp Zoology 284:67 (1999).

Lebkowski JS et al, Human Embryonic Stem Cells: Culture, Differentiation, and Genetic Modification for Regenerative Medicine Applications, Cancer J 7 Suppl 2:S83 (2001).

Loring JF et al, A Gene Expression Profile of Embryonic Stem Cells and Embryonic Stem Cell-Derived Neurons, Restor Neurol Neurosci 18:81 (2001).

Monk M et al, Isolation of Novel Developmental Genes from Human Germ Cell, Oocyte and Embryo cDNA by Differential Display, Reprod Fertil Dev 13:51 (2001).

Monk M et al, Human Embryonic Genes Re-Expressed in Cancer Cells, Oncogene 20:8085 (2001).

Natale DR et al, Sensitivity of Bovine Blastocyst Gene Expression Patterns to Culture Environments Assessed by Differential Display RT-PCR, Reprod 122:687 (2001).

Nishiguchi S et al, A Catalogue of Genes in Mouse Embryonal Carcinoma F9 Cells Identified with Expressed Sequence Tags, J Biochem 119:749 (1996).

Pesce M et al, In Line with Our Ancestors: Oct.-4 and the Mammalian *Germ*, BioEssays 20:722 (1998).

Prelle K et al, Pluripotent Stem Cells—Model of Embryonic Development, Tool for Gene Targeting, and Basis of Cell Therapy, Anat Histol Embryol 31:169 (2002).

Ramalho-Santos M et al, "Stemness": Transcriptional Profiling of Embryonic and Adult Stem Cells, Science 298:597 (Oct. 2002).

Rossant J et al, Chimeras and Mosaics in Mouse Mutant Analysis, TIG 14(9) (Sep. 1998).

Saitou M et al, A Molecular Programme for the Specification of Germ Cell Fate in Mice, Nature 418:293 (Jul. 2002).

Sasaki N et al, Characterization of Gene Expression in Mouse Blastocyst Using Single-Pass Sequencing of 3995 Clones, Genomics 49:167 (1998).

Schopperle WM et al, Human Embryonal Carcinoma Tumor Antigen, Gp200/GCTM-2, is Podocalyxin, Biochem Biophys Res Commun 300:285 (2003).

Shamblott MJ et al, Derivation of Pluripotent Stem Cells from Cultured Human Primordial Germ Cells, PNAS 95:13726 (Nov. 1998).

Stanford WL et al, Expression Trapping: Identification of Novel Genes Expressed in Hematopoietic and Endothelial Lineages by Gene Trapping in ES Cells, Blood 92(12):4622 (Dec. 1998).

Tanaka TS et al, Gene Expression Profiling of Embryo-Derived Stem Cells Reveals Candidate Genes Associated with Pluripotency and Lineage Specificity, Genome Res 12:1921 (2002).

Thomson JA et al, Embryonic Stem Cell Lines Derived from Human Blastocysts, Science 282:1145 (Nov. 1998).

Woltjen K et al, Retro-Recombination Screening of a Mouse Embryonic Stem Cell Genomic Library, Nucleic Acids Res 28(9):E41 (2000).

Xiong JW et al, Large-Scale Screening for Developmental Genes in Embryonic Stem Cells and Embryoid Bodies Using Retroviral Entrapment Vectors, Dev Dyn 212:181 (1998).

Xu C et al, Feeder-Free Growth of Undifferentiated Human Embryonic Stem Cells, Nat Biotech 19:971 (Oct. 2001).

Zambrowicz BP et al, Disruption and Sequence Identification of 2,000 Genes in Mouse Embryonic Stem Cells, Nature 392:608 (Apr. 1998).

Zhang P et al, Towards Genetic Genome Projects: Genomic Library Screening and Gene-Targeting Vector Construction in a Single Step, Nat Genet 30:31 (Jan. 2002).

zur Nieden NI et al, Molecular Markers in Embryonic Stem Cells, Toxicol in Vitro 15:455 (2001).

ES Cell International Internet Listing, Printed Jan. 2, 2003.

Stem Cell Array Information, Printed from SuperArray Website Jun. 17, 2003.

* cited by examiner

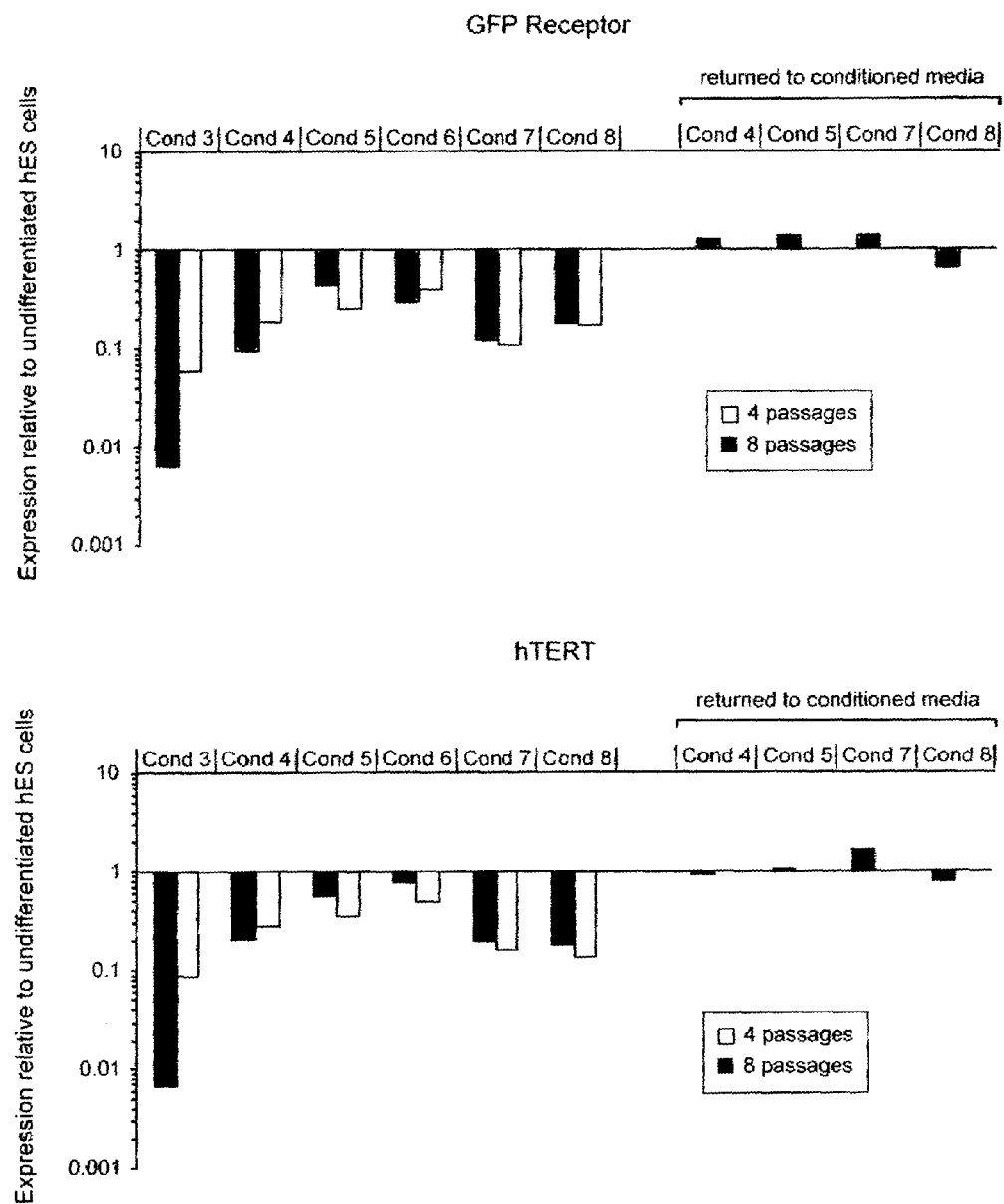

US 7,153,650 B2

MARKER SYSTEM FOR PREPARING AND CHARACTERIZING HIGH-QUALITY HUMAN EMBRYONIC STEM CELLS

TECHNICAL FIELD

This invention relates generally to the field of cell biology of stem cells. More specifically, it relates to phenotypic markers that can be used to characterize, qualify, and control differentiation of pluripotent cells, and to evaluate clinical conditions associated with marker expression.

BACKGROUND

A promising development in the field of regenerative medicine has been the isolation and propagation of human stem cells from the early embryo. These cells have two very special properties: First, unlike other normal mammalian cell types, they can be propagated in culture almost indefinitely, providing a virtually unlimited supply. Second, they can be used to generate a variety of tissue types of interest as a source of replacement cells and tissues for use in therapy.

Thomson et al. (Science 282:114, 1998; U.S. Pat. No. 6,200,806) were the first to successfully isolate and propagate embryonic stem cells from human blastocysts. Gearhart and coworkers derived human embryonic germ cell lines from fetal gonadal tissue (Shambloft et al., Proc. Natl. Acad. Sci. USA 95:13726, 1998; U.S. Pat. No. 6,090,622).

International Patent Publication WO 99/20741 (Geron Corp.) describes methods and materials for the growth of primate-derived primordial stem cells. International Patent Publication WO 01/51616 (Geron Corp.) provides techniques for growth and differentiation of human pluripotent stem cells. An article by Xu et al. (Nature Biotechnology 19:971, 2001) describes feeder-free growth of undifferentiated human embryonic stem cells. Lebkowski et al. (Cancer J. 7 Suppl. 2:S83, 2001) discuss the culture, differentiation, and genetic modification of human embryonic stem cell for regenerative medicine applications. These publications report exemplary culture methods for propagating human embryonic stem cells in an undifferentiated state, and their use in preparing cells for human therapy.

Markers for identifying undifferentiated pluripotent stem cells include SSEA-4, Tra-1-60, and Tra-1-81 (Thomson et al. and Gearhart et al., supra). They also express human telomerase reverse transcriptase, and the POU transcription factor Oct 3/4 (WO 01/51616; Amit et al., Dev. Biol. 227:271, 2000; Xu et al., supra).

Loring et al. (Restor. Neurol. Neurosci. 18:81, 2001) review gene expression profiles of embryonic stem cells and ES-derived neurons. Pesce et al. (Bioessays 20:722, 1998) comment on the potential role of transcription factor Oct-4 in the totipotent germ-line cycle of mice. Gajovic et al. (Exp. Cell Res. 242:138, 1998) report that genes expressed after retinoic acid-mediated differentiation of embryoid bodies are likely to be expressed during embryo development. Zur Nieden et al. (Toxicol. in Vitro 15:455, 2001) propose certain molecular markers for embryonic stem cells. Henderson et al. (Stem Cells 20:329, 2002) report that preimplantation human embryos and ES cells have comparable expression of SSEAs. Tanaka et al. (Genome Res. 12:1921, 2002) profile gene expression in mouse ES cells to identify candidate genes associated with pluripotency and lineage specificity. Draper et al. (J. Anat. 299:249, 2002) review change of surface antigens of human embryonic stem cells upon differentiation in culture.

Kelly et al. (Mol Reprod. Dev. 56:113, 2000) report DNA microarray analyses of genes regulated during the differentiation of embryonic stem cells. Woltjen et al. (Nucl. Acids Res. 28:E41, 2000) report retro-recombination screening of a mouse embryonic stem cell genomic library. Monk et al. (Oncogene 20:8085, 2001) list human embryonic genes re-expressed in cancer cells. Tanaka et al. (Genome Res. 12:1921, 2002) discuss gene expression profiling of embryo-derived stem cells, and candidate genes putatively associated with pluripotency and lineage specificity. Monk et al. report developmental genes identified by differential display (Reprod. Fertil. Dev. 13:51, 2001). Natale et al. (Reprod. 122:687, 2001) characterize bovine blastocyst gene expression patterns by differential display RT-PCR.

Fan et al. (Dev. Biol. 210:481, 1999) propose that forced expression of the homeobox-containing gene Pem blocks differentiation of embryonic stem cells. Abdel-Rahman et al. (Hum. Reprod. 10:2787, 1995) report the effect of expressing transcription regulating genes in human preimplantation embryos. Jackson et al. (J. Biol. Chem. 277:38683, 2002) describe the cloning and characterization of Ehox, a homeobox gene that reportedly plays a role in ES cell differentiation.

The following disclosure provides new markers and marker combinations that are effective means to identify, characterize, qualify, and control differentiation of pluripotent cells.

SUMMARY OF THE INVENTION

This invention identifies a number of genes that are up- or down-regulated during the course of differentiation of early-stage pluripotent stem cells obtained from primates, exemplified by human embryonic stem cells. As a consequence, the genes are differentially expressed in undifferentiated versus differentiated cells. This property confers special benefit on these genes for identification, characterization, culturing, differentiation, and manipulation of stem cells and their progeny, and other cells that express the same markers.

One aspect of this invention is a system for assessing a culture of undifferentiated primate pluripotent stem (pPS) cells or their progeny, in which expression of one or more of the identified markers listed in the disclosure is detected or measured. The level of expression can be measured in isolation or compared with any suitable standard, such as undifferentiated pPS cells maintained under specified conditions, progeny at a certain stage of differentiation, or stable end-stage differentiated cells, such as may be obtained from the ATCC. Depending on whether the marker(s) are up- or down-regulated during differentiation, presence of the markers is correlated with the presence or proportion of undifferentiated or differentiated cells in the population.

An exemplary (non-limiting) combination suitable for qualifying cultures of undifferentiated pPS cells is a marker selected from the list of Cripto, gastrin-releasing peptide (GRP) receptor, and podocalyxin-like protein, in combination with either hTERT and/or Oct 3/4 (POU domain, class 5 transcription factor), or a second marker from the list. Additional markers can also be measured as desired. Markers can be detected at the mRNA level by PCR amplification, at the protein or enzyme product level by antibody assay, or by any suitable technique.

The marker system of this invention can be used for quantifying the proportion of undifferentiated pPS cells or differentiated cells in the culture; for assessing the ability of a culture system or component thereof (such as a soluble factor, culture medium, or feeder cell) to maintain pPS cells in an undifferentiated state; for assessing the ability of a culture system or component thereof to cause differentiation of pPS cells into a culture of lineage-restricted precursor cells or terminally differentiated cells; or for any other worthwhile purpose. This invention includes kits and the use of specific reagents in order to measure the expression of the markers whenever appropriate.

This invention also provides a system assessing the growth characteristics of a cell population by detecting or measuring expression of one or more of the differentially expressed marker genes identified in this disclosure. This can be applied not only to various types of pPS cells and progenitor cells in various stages of differentiation, but also to clinical samples from a disease condition associated with abnormal cell growth. Renewed expression of markers of a relatively undifferentiated phenotype may be diagnostic of disease conditions such as cancer, and can serve as a means by which to target therapeutic agents to the disease site.

The marker system can also be used to regulate gene expression. Transcriptional control elements for the markers will cause an operatively linked encoding region to be expressed preferentially in undifferentiated or differentiated cells. For example, the encoding sequence can be a reporter gene (such as a gene that causes the cells to emit fluorescence), a positive selection marker (such as a drug resistance gene), or a negative selection marker. Vector constructs comprising recombinant elements linked in this fashion can be used to positively select or deplete undifferentiated, differentiated, or cancerous cells from a mixed population or in vivo, depending on the nature of the effector gene and whether transcription is up- or down-regulated during differentiation. They can also be used to monitor culture conditions of pPS cells, differentiation conditions, or for drug screening.

The marker system of this invention can also be used to sort differentiated cells from less differentiated cells. The marker can be used directly for cell separation by adsorption using an antibody or lectin, or by fluorescence activated cell sorting. Alternatively, these separation techniques can be effected using a transcription promoter from the marker gene in a promoter-reporter construct.

The marker system of this invention can be used to map differentiation pathways or influence differentiation. Markers suited for this purpose may act as transcription regulators, or encode products that enhance cell interaction in some fashion. pPS cells or their differentiated progeny are genetically altered to increase expression of one or more of the identified genes using a transgene, or to decrease expression, for example, using an antisense or siRNA construct. Alternatively, gene products involved in cell interaction or signaling can be added directly to the culture medium. The effect of this can be to help maintain the transfected cell in the undifferentiated state, promote differentiation in general, or direct differentiation down a particular pathway.

Another aspect of the invention are methods for identifying these and other genes that are up- or down-regulated upon differentiation of any cell type. The methods involve comparing expression libraries obtained from the cells before and after differentiation, by sequencing transcripts in each of the libraries, and identifying genes that have statistically significant differences in the relative number of transcripts (as a percentage of transcripts in each library) at a confidence level of 67%, 95%, or 98%. The method can be enhanced by creating assemblies in which different sequences are counted for the same transcript if they are known to correspond to a single transcript according to previously compiled data.

Amongst the differentially expressed markers identified in this disclosure are 39 nucleotide sequences which are not present in their entirety in the UniGene database. These are listed in this disclosure as SEQ. ID NOs:101 to 139. This invention includes novel nucleic acids consisting of or containing any of these sequences or the complementary sequences, and novel fragments thereof. This invention also includes novel polypeptides encoded in these sequences (made either by expressing the nucleic acid or by peptide synthesis), antibodies specific for the polypeptides (made by conventional techniques or through a commercial service), and use of these nucleic acids, peptides, and antibodies for any industrial application.

Also embodied in this invention are culture conditions and other cell manipulations identified using the marker system of this invention that are suitable for maintaining or proliferating pPS cells without allowing differentiation, or causing them to differentiate in a certain fashion. Culture conditions tested and validated according to this invention are illustrated in the example section.

Other embodiments of the invention will be apparent from the description that follows.

DRAWINGS

FIG. 1 shows the profile of genes preferentially expressed in undifferentiated pluripotent stem cells, upon preliminary differentiation of the cells by culturing in retinoic acid or DMSO. Level of gene expression at the mRNA level was measured by real-time PCR assay. Any of the genes showing substantial down-regulation upon differentiation can be used to characterize the undifferentiated cell population, and culture methods suitable for maintaining them in an undifferentiated state.

Figure 2:
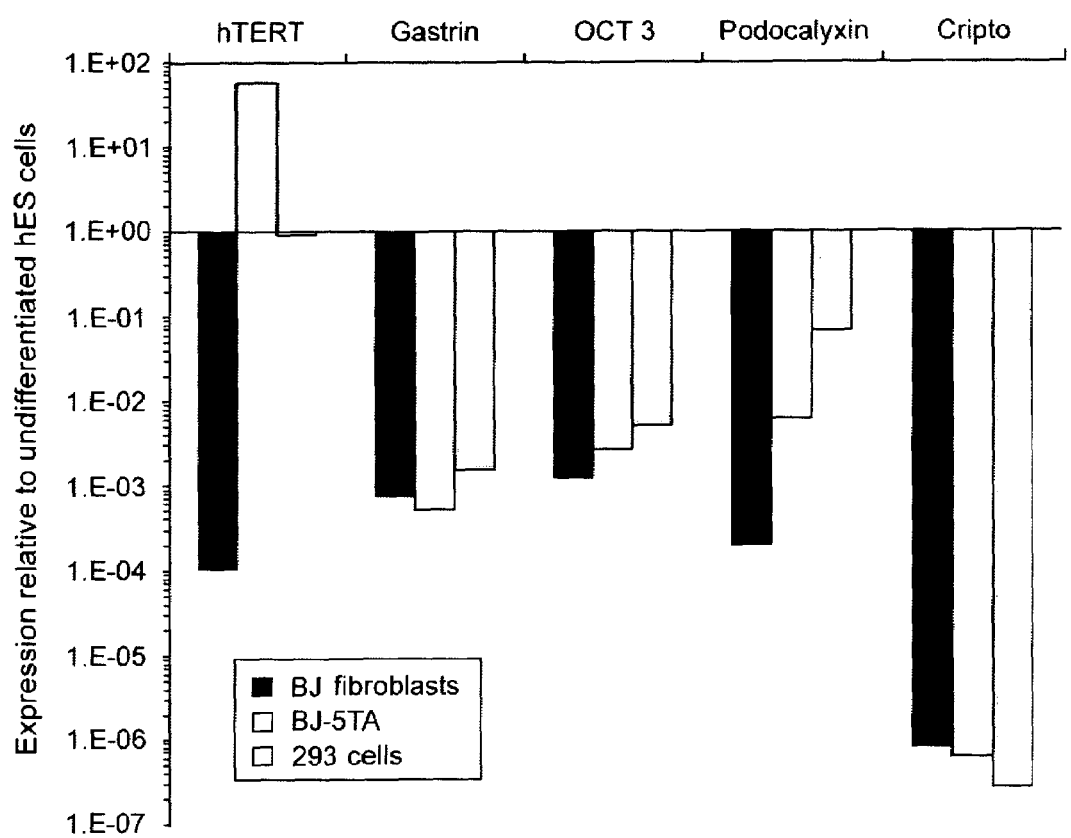

FIG. 2 shows the level of expression of five genes in hES cells, compared with fully differentiated cells. This five-marker panel provides robust qualification of the undifferentiated phenotype.

Figure 3:
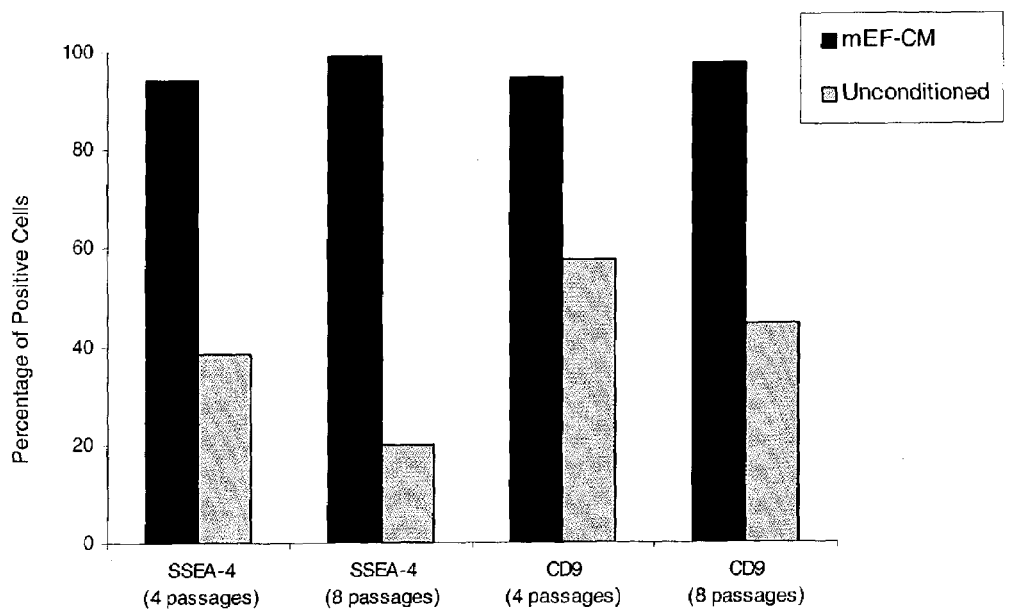

FIG. 3 show results of an experiment in which hES cells of the H1 line were maintained for multiple passages in different media. Medium conditioned with feeder cells provides factors effective to allow hES cells to proliferate in culture without differentiating. However, culturing in unconditioned medium leads to decreased percentage of cells expressing CD9, and the classic hES cell marker SSEA-4.

Figure 4:
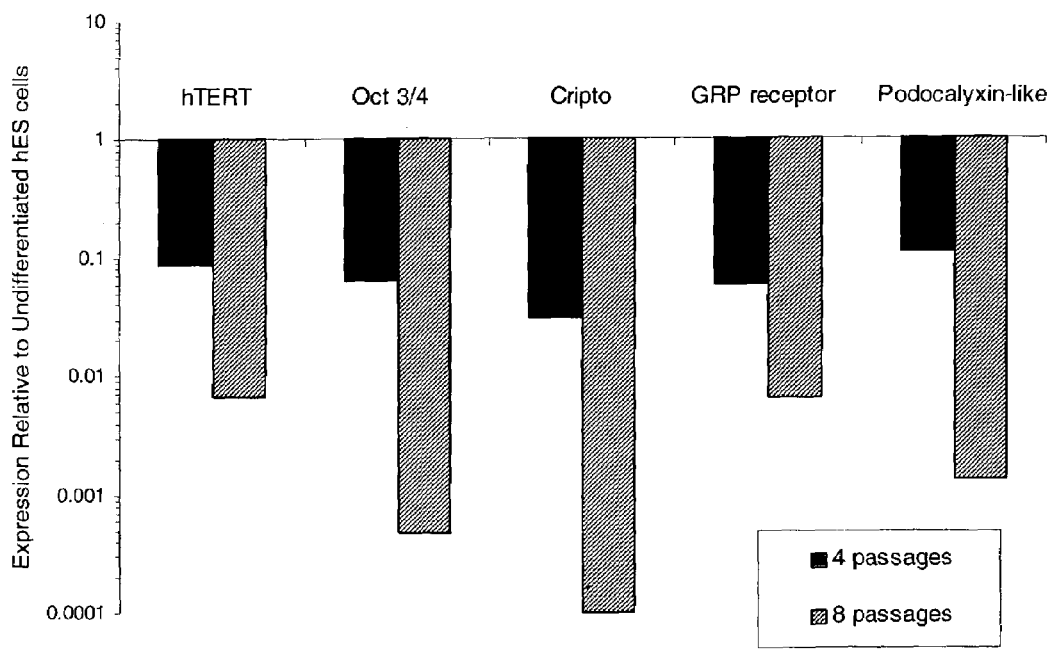

FIG. 4 illustrates the sensitivity of hTERT, Oct 3/4, Cripto, GRP receptor, and podocalyxin-like protein (measured by real-time PCR) as a means of determining the degree of differentiation of the cells. After multiple passages in unconditioned medium, all five markers show expression that has been downregulated by 10 to $10^4$-fold.

Figure 5:
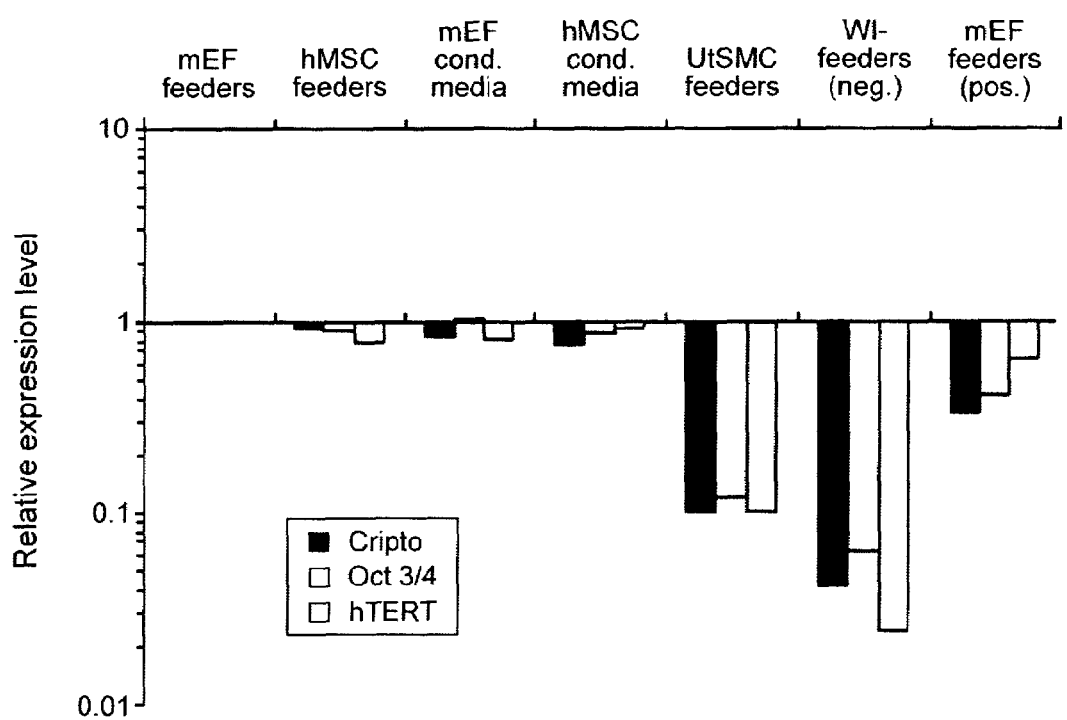

FIG. 5 shows results of an experiment in which the hES cell line H1 was grown on different feeder cell lines: mEF=mouse embryonic fibroblasts; hMSC=human mesenchymal stem cells; UtSMC=uterine smooth muscle cells; WI-38=human lung fibroblasts. As monitored using Cripto, the hMSC is suitable for use as feeder cells to promote hES cell proliferation without differentiation.

Figure 6A:
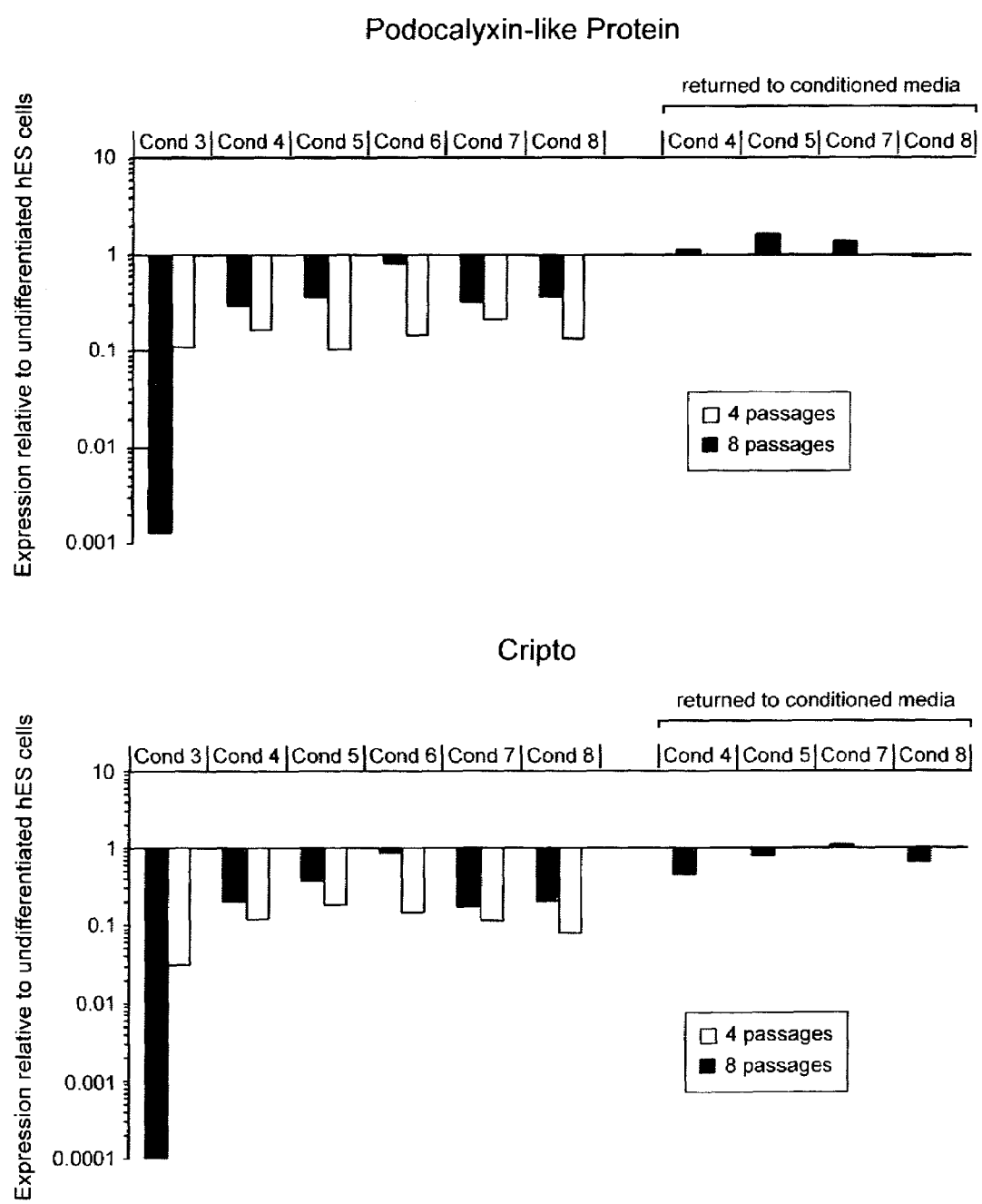

FIG. 6 shows results of an experiment in which different media were tested for their ability to promote growth of hES cells without proliferation. The test media were not preconditioned, but supplemented with 8–40 ng/mL bFGF, with or without stem cell factor, Flt3 ligand, or LIF. Effective combinations of factors (Conditions 4 to 8) were identified by following the undifferentiated phenotype using the markers of this invention. Alterations in expression profiles were temporary and reversible, showing that the cells are still undifferentiated.

DETAILED DESCRIPTION

The propensity of pluripotent stem cells to differentiate spontaneously has made it challenging for investigators to work with these cells. Consistent cultures of undifferentiated stem cells are required to compare results obtained from multiple experiments performed within or between laboratories. Unfortunately, morphological characterization is subjective and especially difficult for cultures that often contain 10–20% differentiated cells. Nevertheless, having a set of standardized criteria will be important in qualifying these cells for use in clinical therapy.

The marker system identified in this disclosure provides the basis for establishing these standards. 148,453 different transcripts were amplified and sequenced from undifferentiated human embryonic stem cells, and three types of progeny. As a result of this sequencing effort, 532 genes were identified having substantially higher EST counts in undifferentiated cells, and 142 genes were identified having substantially higher EST counts after differentiation. Other differentially expressed genes were identified by microarray analysis of undifferentiated cells, compared with cells at the beginning of the differentiation process.

The system provided by this invention can be used not only to qualify populations of undifferentiated cells, but in other powerful ways of maintaining and manipulating cells described later in this disclosure. Culture systems have been identified and protocols have been developed to expand cultures of undifferentiated cells and produce commercially viable quantities of cells for use in research, drug screening, and regenerative medicine.

Definitions

"Pluripotent Stem cells" (pPS cells) are pluripotent cells that have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8–12 week old SCID mice. The term includes both established lines of stem cells of various kinds, and cells obtained from primary tissue that are pluripotent in the manner described. For the purposes of this disclosure, the pPS cells are not embryonal carcinoma (EC) cells, and are not derived from a malignant source. It is desirable (but not always necessary) that the cells be euploid. Exemplary pPS cells are obtained from embryonic or fetal tissue at any time after fertilization.

"Human Embryonic Stem cells" (hES cells) are pluripotent stem cells derived from a human embryo in the blastocyst stage, or human pluripotent cells produced by artificial means (such as by nuclear transfer) that have equivalent characteristics. Exemplary derivation procedures and features are provided in a later section.

hES cell cultures are described as "undifferentiated" when a substantial proportion (at least 20%, and possibly over 50% or 80%) of stem cells and their derivatives in the population display morphological characteristics of undifferentiated cells, distinguishing them from differentiated cells of embryo or adult origin. It is understood that colonies of undifferentiated cells within the population will often be surrounded by neighboring cells that are differentiated. It is also understood that the proportion of cells displaying the undifferentiated phenotype will fluctuate as the cells proliferate and are passaged from one culture to another. Cells are recognized as proliferating in an undifferentiated state when they go through at least 4 passages and/or 8 population doublings while retaining at least about 50%, or the same proportion of cells bearing characteristic markers or morphological characteristics of undifferentiated cells.

A "differentiated cell" is a cell that has progressed down a developmental pathway, and includes lineage-committed progenitor cells and terminally differentiated cells.

"Feeder cells" or "feeders" are terms used to describe cells of one type that are co-cultured with cells of another type, to provide an environment in which the cells of the second type can grow. hES cell populations are said to be "essentially free" of feeder cells if the cells have been grown through at least one round after splitting in which fresh feeder cells are not added to support the growth of pPS cells.

The term "embryoid bodies" refers to aggregates of differentiated and undifferentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry.

A cell "marker" is any phenotypic feature of a cell that can be used to characterize it or discriminate it from other cell types. A marker of this invention may be a protein (including secreted, cell surface, or internal proteins; either synthesized or taken up by the cell); a nucleic acid (such as an mRNA, or enzymatically active nucleic acid molecule) or a polysaccharide. Included are determinants of any such cell components that are detectable by antibody, lectin, probe or nucleic acid amplification reaction that are specific for the cell type of interest. The markers can also be identified by a biochemical or enzyme assay that depend on the function of the gene product. Associated with each marker is the gene that encodes the transcript, and the events that lead to marker expression.

The terms "polynucleotide" and "nucleic acid" refer to a polymeric form of nucleotides of any length. Included are genes and gene fragments, mRNA, cDNA, plasmids, viral and non-viral vectors and particles, nucleic acid probes, amplification primers, and their chemical equivalents. As used in this disclosure, the term polynucleotide refers interchangeably to double- and single-stranded molecules. Unless otherwise specified, any embodiment of the invention that is a polynucleotide encompasses both a double-stranded form, and each of the two complementary single-stranded forms known or predicted to make up the double-stranded form.

A cell is said to be "genetically altered" or "transfected" when a polynucleotide has been transferred into the cell by any suitable means of artificial manipulation, or where the cell is a progeny of the originally altered cell that has inherited the polynucleotide.

A "control element" or "control sequence" is a nucleotide sequence involved in an interaction of molecules that contributes to the functional regulation of a polynucleotide, including replication, duplication, transcription, splicing, translation, or degradation of the polynucleotide. "Operatively linked" refers to an operative relationship between genetic elements, in which the function of one element influences the function of another element. For example, an expressible encoding sequence may be operatively linked to a promoter that drives gene transcription.

The term "antibody" as used in this disclosure refers to both polyclonal and monoclonal antibody. The ambit of the term deliberately encompasses not only intact immunoglobulin molecules, but also such fragments and derivatives of immunoglobulin molecules that retain a desired binding specificity.

General Techniques

Methods in molecular genetics and genetic engineering are described generally in the current editions of Molecular Cloning: A Laboratory Manual, (Sambrook et al.); Oligonucleotide Synthesis (M. J. Gait, ed.); Animal Cell Culture (R. I. Freshney, ed.); Gene Transfer Vectors for Mammalian Cells (Miller & Calos, eds.); Current Protocols in Molecular Biology and Short Protocols in Molecular Biology, $3^{rd}$ Edition (F. M. Ausubel et al., eds.); and Recombinant DNA Methodology (R. Wu ed., Academic Press). Antibody production is described in Basic Methods in Antibody Production and Characterization (Howard & Bethell eds., CRC Press, 2000).

A survey of relevant techniques is provided in such standard texts as DNA Sequencing (A. E. Barron, John Wiley, 2002), and DNA Microarrays and Gene Expression (P. Baldi et al., Cambridge U. Press, 2002). For a description of the molecular biology of cancer, the reader is referred to Principles of Molecular Oncology (M. H. Bronchud et al. eds., Humana Press, 2000); The Biological Basis of Cancer (R. G. McKinnel et al. eds., Cambridge University Press, 1998); and Molecular Genetics of Cancer (J. K. Cowell ed., Bios Scientific Publishers, 1999).

Sources of Stem Cells

This invention is based on observations made with established lines of hES cells. The markers are suitable for identifying, characterizing, and manipulating related types of undifferentiated pluripotent cells. They are also suitable for use with pluripotent cells obtained from primary embryonic tissue, without first establishing an undifferentiated cell line. It is contemplated that the markers described in this application will in general be useful for other types of pluripotent cells, including embryonic germ cells (U.S. Pat. Nos. 6,090,622 and 6,251,671), and ES and EG cells from other mammalian species, such as non-human primates.

Embryonic Stem Cells

Embryonic stem cells can be isolated from blastocysts of members of primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, outlined in WO 01/51610 (Bresagen).

hES cells can be obtained from human preimplantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1–2 weeks by brief trypsinization, exposure to Dulbecco's PBS (containing 2 mM EDTA), exposure to type IV collagenase (~200 U/mL; Gibco) or by selection of individual colonies by micropipette. Clump sizes of about 50 to 100 cells are optimal.

Propagation of pPS Cells in an Undifferentiated State pPS cells can be propagated continuously in culture, using culture conditions that promote proliferation without promoting differentiation. Exemplary serum-containing ES medium is made with 80% DMEM (such as Knock-Out DMEM, Gibco), 20% of either defined fetal bovine serum (FBS, Hyclone) or serum replacement (US 20020076747 A1, Life Technologies Inc.), 1% non-essential amino acids, 1 mM L-glutamine, and 0.1 mM β-mercaptoethanol. Just before use, human bFGF is added to 4 ng/mL (WO 99/20741, Geron Corp.).

Traditionally, ES cells are cultured on a layer of feeder cells, typically fibroblasts derived from embryonic or fetal tissue. Embryos are harvested from a CF1 mouse at 13 days of pregnancy, transferred to 2 mL trypsin/EDTA, finely minced, and incubated 5 min at 37° C. 10% FBS is added, debris is allowed to settle, and the cells are propagated in 90% DMEM, 10% FBS, and 2 mM glutamine. To prepare a feeder cell layer, cells are irradiated to inhibit proliferation but permit synthesis of factors that support ES cells (~4000 rads γ-irradiation). Culture plates are coated with 0.5% gelatin overnight, plated with 375,000 irradiated mEFs per well, and used 5 h to 4 days after plating. The medium is replaced with fresh hES medium just before seeding pPS cells.

Scientists at Geron have discovered that pPS cells can be maintained in an undifferentiated state even without feeder cells. The environment for feeder-free cultures includes a suitable culture substrate, particularly an extracellular matrix such as Matrigel® or laminin. The pPS cells are plated at >15,000 cells $cm^{-2}$ (optimally 90,000 $cm^{-2}$ to 170,000 $cm^{-2}$). Typically, enzymatic digestion is halted before cells become completely dispersed (say, ~5 min with collagenase IV). Clumps of ~10 to 2,000 cells are then plated directly onto the substrate without further dispersal. Alternatively, the cells can be harvested without enzymes before the plate reaches confluence by incubating ~5 min in a solution of 0.5 mM EDTA in PBS. After washing from the culture vessel, the cells are plated into a new culture without further dispersal. In a further illustration, confluent human embryonic stem cells cultured in the absence of feeders are removed from the plates by incubating with a solution of 0.05% (wt/vol) trypsin (Gibco) and 0.053 mM EDTA for 5–15 min at 37° C. The remaining cells in the plate are removed and the cells are triturated into a suspension comprising single cells and small clusters, and then plated at densities of 50,000–200,000 cells cm$^{-2}$ to promote survival and limit differentiation.

Feeder-free cultures are supported by a nutrient medium containing factors that support proliferation of the cells without differentiation. Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells. Medium can be conditioned by plating the feeders at a density of ~5–6×10$^4$ cm$^{-2}$ in a serum free medium such as KO DMEM supplemented with 20% serum replacement and 4 ng/mL bFGF. Medium that has been conditioned for 1–2 days is supplemented with further bFGF, and used to support pPS cell culture for 1–2 days. Alternatively or in addition, other factors can be added that help support proliferation without differentiation, such as ligands for the FGF-2 or FGF-4 receptor, ligands for c-kit (such as stem cell factor), ligands for receptors associated with gp130, insulin, transferrin, lipids, cholesterol, nucleosides, pyruvate, and a reducing agent such as p-mercaptoethanol. Aspects of the feeder-free culture method are further discussed in International Patent Publications WO 99/20741, WO 01/51616; Xu et al., Nat. Biotechnol. 19:971, 2001; and PCT application PCT/US02/28200. Exemplary culture conditions tested and validated using the marker system of this invention are provided below in Example 5.

Under the microscope, ES cells appear with high nuclear/cytoplasmic ratios, prominent nucleoli, and compact colony formation with poorly discernable cell junctions. Conventional markers for hES cells are stage-specific embryonic antigen (SSEA) 3 and 4, and markers detectable using antibodies Tra-1-60 and Tra-1-81 (Thomson et al., Science 282:1145, 1998). Differentiation of pPS cells in vitro results in the loss of SSEA-4, Tra-1-60, and Tra-1-81 expression, and increased expression of SSEA-1.

Markers of Undifferentiated PPS Cells and their Differentiated Progeny

The tables and description provided later in this disclosure provide markers that distinguish undifferentiated pPS cells from their differentiated progeny.

Expression libraries were made from ES cells (WO 01/51616), embryoid bodies (WO 01/51616), and cells differentiated towards the hepatocyte (WO 01/81549) or neural cell (WO 01/88104) lineage. mRNA was reverse transcribed and amplified, producing expressed sequence tags (ESTs) occurring in frequency proportional to the level of expression in the cell type being analyzed. The ESTs were subjected to automatic sequencing, and counted according to the corresponding unique (non-redundant) transcript. A total of 148,453 non-redundant transcripts were represented in each of the 4 libraries. Genes were then identified as having a differential expression pattern if the number of EST counts of the transcript was statistically different between the libraries being compared.

In a parallel set of experiments, mRNA from each of the cell types was analyzed for binding to a broad-specificity EST-based microarray, performed according to the method described in WO 01/51616. Genes were identified as having a differential expression pattern if they showed a comparatively different signal on the microarray.

Significant expression differences determined by EST sequencing, microarray analysis, or other observations were confirmed by real-time PCR analysis. The mRNA was amplified by PCR using specific forward and reverse primers designed from the GenBank sequence, and the amplification product was detected using labeled sequence-specific probes. The number of amplification cycles required to reach a threshold amount was then compared between different libraries.

Distinguishing markers fall into several categories. Those of particular interest include the following:

Markers characteristically expressed at a higher level in undifferentiated pPS cells than any of the differentiated cells, indicating down-regulation during differentiation. The gene products may be involved in maintaining the undifferentiated phenotype.

Markers characteristically expressed at a higher level in the three differentiated cell types than in the undifferentiated cells, indicating up-regulation during differentiation. The gene products may be involved in the general differentiation process.

Markers characteristically expressed at a higher level in one of the differentiated cell types. The encoded genes may be involved in differentiation down restricted lineages.

Markers can also be classified according to the function of the gene product or its location in the cell. Where not already indicated, protein gene products can be predicted by referencing public information according to the GenBank accession number, or by translating the open reading frame after the translation start signal though the genetic code. Features of the markers listed can be determined by the descriptors give in the tables below, or by using the accession number or sequence data to reference public information. Marker groups of particular interest include the following:

Secreted proteins—of interest, for example, because they can be detected by immunoassay of the culture supernatant, and may transmit signals to neighboring cells. Secreted proteins typically have an N-terminal signal peptides, and may have glycosylation sites.

Surface membrane proteins—of interest, for example, because they can be used for cell-surface labeling and affinity separation, or because they act as receptors for signal transduction. They may have glycosylation sites and a membrane spanning region. A Markov model for predicting transmembrane protein topology is described by Krogh et al., J. Mol Biol. 305:567, 2001.

Enzymes with relevant function. For example, enzymes involved in protein synthesis and cleavage or in apoptosis may influence differentiation. Glycosyltransferases decorate the cell membrane with distinguishing carbohydrate epitopes that may play a role in cellular adhesion or localization.

Transcription regulatory factors—of interest for their potential to influence differentiation, as explained later in this disclosure. These factors sometimes have zinc fingers or other identifiable topological features involved in the binding or metabolism of nucleic acids.

Through the course of this work, the key signaling pathways Wnt, Sonic hedgehog (Shh), and Notch emerged as regulators of growth of pPS cells. Interestingly, these pathways have also been shown to play a role in the growth of tumor cells of various kinds, and in embryonic development of lower species.

Now that genes have been identified that are up-regulated or down-regulated upon differentiation, a number of commercial applications of these markers will be apparent to the skilled reader. The sections that follow provide non-limiting illustrations of how some of these embodiments can be implemented.

Use of Cell Markers to Characterize pPS Cells and their Differentiated PROGENY

The markers provided in this disclosure can be used as a means to identify both undifferentiated and differentiated cells—either a population as a whole, or as individual cells within a population. This can be used to evaluate the expansion or maintenance of pre-existing cell populations, or to characterize the pluripotent nature (or lineage commitment) of newly obtained populations.

Expression of single markers in a test cell will provide evidence of undifferentiated or differentiated phenotype, according to the expression pattern listed later in this disclosure. A plurality of markers (such as any 2, 3, 4, 5, 6, 8, 10, 12, 15, or 20 markers from Tables 2–3 or 5–9) will provide a more detailed assessment of the characteristics of the cell. Expression of genes that are down-regulated and/or lack of expression of genes that are up-regulated upon differentiation correlates with a differentiated phenotype. Expression of genes that are up-regulated and/or lack of expression of genes that are down-regulated upon differentiation correlates with an undifferentiated phenotype. The markers newly identified in this disclosure may be analyzed together (with or without markers that were previously known) in any combination effective for characterizing the cell status or phenotype.

Tissue-specific markers can be detected using any suitable immunological technique—such as flow cytochemistry for cell-surface markers, or immunocytochemistry (for example, of fixed cells or tissue sections) for intracellular or cell-surface markers. Expression of a cell-surface antigen is defined as positive if a significantly detectable amount of antibody will bind to the antigen in a standard immunocytochemistry or flow cytometry assay, optionally after fixation of the cells, and optionally using a labeled secondary antibody or other conjugate to amplify labeling.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for particular markers listed in this disclosure can be obtained from public databases such as GenBank.

These and other suitable assay systems are described in standard reference texts, such as the following: PCR Cloning Protocols, $2^{nd}$ Ed (James & Chen eds., Humana Press, 2002); Rapid Cycle Real-Time PCR: Methods and Applications (C. Wittwer et al. eds., Springer-Verlag N.Y., 2002); Immunoassays: A Practical Approach (James Gosling ed., Oxford Univ Press, 2000); Cytometric Analysis of Cell Phenotype and Function (McCarthy et al. eds., Cambridge Univ Press, 2001). Reagents for conducting these assays, such as nucleotide probes or primers, or specific antibody, can be packaged in kit form, optionally with instructions for the use of the reagents in the characterization or monitoring of pPS cells, or their differentiated progeny.

Use of Cell Markers for Clinical Diagnosis

Stem cells regulate their own replenishment and serve as a source of cells that can differentiate into defined cell lineages. Cancer cells also have the ability to self-renew, but lack of regulation results in uncontrolled cellular proliferation. Three key signaling pathways, Wnt, Sonic hedgehog (Shh), and Notch, are known growth regulators of tumor cells. The genomics data provided in this disclosure indicate that all three of these pathways are active in hES cells.

It is a hypothesis of this invention that many of the markers discovered to be more highly expressed in undifferentiated pPS cells can also be up-regulated upon dedifferentiation of cells upon malignant transformation. Accordingly, this disclosure provides a system for evaluating clinical conditions associated with abnormal cell growth, such as hyperplasia or cancers of various kinds. Markers meeting the desired criteria include those contained in Tables 2, 5, 7 and 9.

Expression of each marker of interest is determined at the mRNA or protein level using a suitable assay system such as those described earlier; and then the expression is correlated with the clinical condition that the patient is suspected of having. As before, combinations of multiple markers may be more effective in doing the assessment. Presence of a particular marker may also provide a means by which a toxic agent or other therapeutic drug may be targeted to the disease site.

In a similar fashion, the markers of this invention can be used to evaluate a human or non-human subject who has been treated with a cell population or tissue generated by differentiating pPS cells. A histological sample taken at or near the site of administration, or a site to which the cells would be expected to migrate, could be harvested at a time subsequent to treatment, and then assayed to assess whether any of the administered cells had reverted to the undifferentiated phenotype. Reagents for conducting diagnostic tests, such as nucleotide probes or primers, or specific antibody, can be packaged in kit form, optionally with instructions for the use of the reagents in the determination of a disease condition.

Use of Cell Markers to Assess and Manipulate Culture Conditions

The markers and marker combinations of this invention provide a system for monitoring undifferentiated pPS cells and their differentiated progeny in culture. This system can be used as a quality control, to compare the characteristics of undifferentiated pPS cells between different passages or different batches. It can also be used to assess a change in culture conditions, to determine the effect of the change on the undifferentiated cell phenotype.

Where the object is to produce undifferentiated cells, a decrease in the level of expression of an undifferentiated marker because of the alteration by 3-, 10-, 25-, 100- and 1000-fold is progressively less preferred. Corresponding increases in marker expression may be more beneficial. Moderate decreases in marker expression may be quite acceptable within certain boundaries, if the cells retain their ability to form progeny of all three germ layers is retained, and/or the level of the undifferentiated marker is relatively restored when culture conditions are returned to normal.

In this manner, the markers of this invention can be used to evaluate different feeder cells, extracellular matrixes, base media, additives to the media, culture vessels, or other features of the culture as illustrated in WO 99/20741 and PCT application PCT/US02/28200. Illustrations of this technique are provided below in Example 5 (FIGS. 3 to 6).

In a similar fashion, the markers of this invention can also be used to monitor and optimize conditions for differentiating cells. Improved differentiation procedures will lead to higher or more rapid expression of markers for the differentiated phenotype, and/or lower or more rapid decrease in expression of markers for the undifferentiated phenotype.

Use of Cell Markers to Regulate Gene Expression

Differential expression of the markers listed in this disclosure indicates that each marker is controlled by a transcriptional regulatory element (such as a promoter) that is tissue specific, causing higher levels of expression in undifferentiated cells compared with differentiated cells, or vice versa. When the corresponding transcriptional regulatory element is combined with a heterologous encoding region to drive expression of the encoding region, then the expression pattern in different cell types will mimic that of the marker gene.

Minimum promoter sequences of many of the genes listed in this disclosure are known and further described elsewhere. Where a promoter has not been fully characterized, specific transcription can usually be driven by taking the 500 base pairs immediately upstream of the translation start signal for the marker in the corresponding genomic clone.

To express a heterologous encoding region according to this embodiment of the invention, a recombinant vector is constructed in which the specific promoter of interest is operatively linked to the encoding region in such a manner that it drives transcription of the encoding region upon transfection into a suitable host cell. Suitable vector systems for transient expression include those based on adenovirus and certain types of plasmids. Vectors for long-term expression include those based on plasmid lipofection or electroporation, episomal vectors, retrovirus, and lentivirus.

One application of tissue-specific promoters is expression of a reporter gene. Suitable reporters include fluorescence markers such as green fluorescent protein, luciferase, or enzymatic markers such as alkaline phosphatase and β-galactosidase. Other reporters such as a blood group glycosyltransferase (WO 02/074935), or Invitrogen's pDisplay™, create a cell surface epitope that can be counterstained with labeled specific antibody or lectin. pPS cells labeled with reporters can be used to follow the differentiation process directly, the presence or absence of the reporter correlating with the undifferentiated or differentiated phenotype, depending on the specificity of the promoter. This in turn can be used to follow or optimize culture conditions for undifferentiated pPS cells, or differentiation protocols. Alternatively, cells containing promoter-reporter constructs can be used for drug screening, in which a test compound is combined with the cell, and expression or suppression of the promoter is correlated with an effect attributable to the compound.

Another application of tissue-specific promoters is expression of a positive or negative drug selection marker. Antibiotic resistance genes such as neomycin phosphotransferase, expressed under control of a tissue-specific promoter, can be used to positively select for undifferentiated or differentiated cells in a medium containing the corresponding drug (geneticin), by choosing a promoter with the appropriate specificity. Toxin genes, genes that mediate apoptosis, or genes that convert a prodrug into a toxic compound (such as thymidine kinase) can be used to negatively select against contaminating undifferentiated or differentiated cells in a population of the opposite phenotype (WO 02/42445; GB 2374076).

Promoters specific for the undifferentiated cell phenotype can also be used as a means for targeting cancer cells—using the promoter to drive expression of a gene that is toxic to the cell (WO 98/14593, WO 02/42468), or to drive a replication gene in a viral vector (WO 00/46355). For example, an adenoviral vector in which the GRPR promoter (AY032865) drives the E1a gene should specifically lyse cancer cells in the manner described in Majumdar et al., Gene Ther. 8:568, 2001. Multiple promoters for the undifferentiated phenotype can be linked for improved cancer specificity (U.S. Ser. No. 10/206,447).

Other useful applications of tissue-specific promoters of this invention will come readily to the mind of the skilled reader.

Use of Markers for Cell Separation or Purification

Differentially expressed markers provided in this disclosure are also a means by which mixed cell populations can be separated into populations that are more homogeneous. This can be accomplished directly by selecting a marker of the undifferentiated or differentiated phenotype, which is itself expressed on the cell surface, or otherwise causes expression of a unique cell-surface epitope. The epitope is then used as a handle by which the marked cells can be physically separated from the unmarked cells. For example, marked cells can be aggregated or adsorbed to a solid support using an antibody or lectin that is specific for the epitope. Alternatively, the marker can be used to attach a fluorescently labeled antibody or lectin, and then the cell suspension can be subject to fluorescence-activated cell sorting.

An alternative approach is to take a tissue-specific promoter chosen based on its expression pattern (as described in the last section), and use it to drive transcription of a gene suitable for separating the cells. In this way, the marker from which the promoter is chosen need not itself be a cell surface protein. For example, the promoter can drive expression of a fluorescent gene, such as GFP, and then cells having the marked phenotype can be separated by FACS. In another example, the promoter drives expression of a heterologous gene that causes expression of a cell-surface epitope. The epitope is then used for adsorption-based separation, or to attach a fluorescent label, as already described.

Use of Cell Markers to Influence Differentiation

In another embodiment of this invention, the differentially expressed genes of this invention are caused to increase or decrease their expression level, in order to either inhibit or promote the differentiation process. Suitable genes are those that are believed in the normal case of ontogeny to be active in maintaining the undifferentiated state, active in the general process of differentiation, or active in differentiation into particular cell lineages. Markers of interest for this application are the following:

Transcription factors and other elements that directly affect transcription of other genes, such as Forkhead box O1A (FOXO1A); Zic family member 3 (ZIC3); Hypothetical protein FLJ20582; Forkhead box H1 (FOXH1); Zinc finger protein, Hsal2; KRAB-zinc finger protein SZF1-1; Zinc finger protein of cerebellum ZIC2; and Coup transcription factor 2 (COUP-TF2). Other candidates include those marked in Tables 5 and 6 with the symbol "", and other factors with zinc fingers or nucleic acid binding activity.

Genes that influence cell interaction, such as those that encode adhesion molecules, and enzymes that make substrates for adhesion molecules Genes encoding soluble factors that transmit signals within or between cells, and specific receptors that recognize them and are involved in signal transduction.

One way of manipulating gene expression is to induce a transient or stable genetic alteration in the cells using a suitable vector, such as those already listed. Scientists at Geron Corp. have determined that the following constitutive promoters are effective in undifferentiated hES cells: for transient expression CMV, SV40, EF1α, UbC, and PGK; for stable expression, SV40, EF1α, UbC, MND and PGK. Expressing a gene associated with the undifferentiated phenotype may assist the cells to stay undifferentiated in the absence of some of the elements usually required in the culture environment. Expressing a gene associated with the differentiated phenotype may promote early differentiation, and/or initiate a cascade of events beneficial for obtaining a desired cell population. Maintaining or causing expression of a gene of either type early in the differentiation process may in some instances help guide differentiation down a particular pathway.

Another way of manipulating gene expression is to alter transcription from the endogenous gene. One means of accomplishing this is to introduce factors that specifically influence transcription through the endogenous promoter. Another means suitable for down-regulating expression at the protein level is to genetically alter the cells with a nucleic acid that removes the mRNA or otherwise inhibits translation (for example, a hybridizing antisense molecule, ribozyme, or small interfering RNA). Dominant-negative mutants of the target factor can reduce the functional effect of the gene product. Targeting a particular factor associated with the undifferentiated phenotype in this fashion can be used to promote differentiation. In some instances, this can lead to de-repression of genes associated with a particular cell type.

Where the gene product is a soluble protein or peptide that influences cell interaction or signal transduction (for example, cytokines like osteopontin and Cripto), then it may be possible to affect differentiation simply by adding the product to the cells—in either recombinant or synthetic form, or purified from natural sources. Products that maintain the undifferentiated phenotype can then be withdrawn from the culture medium to initiate differentiation; and products that promote differentiation can be withdrawn once the process is complete.

Since differentiation is a multi-step process, changing the level of gene product on a permanent basis may cause multiple effects. In some instances, it may be advantageous to affect gene expression in a temporary fashion at each sequential step in the pathway, in case the same factor plays different effects at different steps of differentiation. For example, function of transcription factors can be evaluated by changing expression of individual genes, or by invoking a high throughput analysis, using cDNAs obtained from a suitable library such as exemplified in Example 1. Cells that undergo an alteration of interest can be cloned and pulled from multi-well plates, and the responsible gene identified by PCR amplification.

The effect of up- or down-regulating expression of a particular gene can be determined by evaluating the cell for morphological characteristics, and the expression of other characteristic markers. Besides the markers listed later in this disclosure, the reader may want to follow the effect on particular cell types, using markers for later-stage or terminally differentiated cells. Tissue-specific markers suitable for this purpose are listed in WO 01/81549 (hepatocytes), WO 01/88104 (neural cells), PCT/US02/20998 (osteoblasts and mesenchymal cells), PCT/US02/22245 (cardiomyocytes), PCT/US02/39091 (hematopoietic cells), PCT/US02/39089 (islet cells), and PCT/US02/39090 (chondrocytes). Such markers can be analyzed by PCR amplification, fluorescence labeling, or immunocytochemistry, as already described. Promoter-reporter constructs based on the same markers can facilitate analysis when expression is being altered in a high throughput protocol.

The Examples that Follow are Provided for Further Illustration, and are Not Meant to Limit the Claimed Invention

EXAMPLES

Example 1

An EST Database of Undifferentiated hES Cells and Their Differentiated Progeny cDNA libraries were prepared from human embryonic stem (hES) cells cultured in undifferentiated form. cDNA libraries were also prepared from progeny, subject to non-specific differentiation as embryoid bodies (EBs), or taken through the preliminary stages of established differentiation protocols for neurons (preNEU) or hepatocytes (preHEP).

The hES cell lines H1, H7, and H9 were maintained under feeder-free conditions. Cultures were passaged every 5-days by incubation in 1 mg/mL collagenase IV for 5–10 min at 37° C., dissociated and seeded in clumps at 2.5 to $10 \times 10^5$ cells/well onto Matrigel™-coated six well plates in conditioned medium supplemented with 8 mg/mL bFGF. cDNA libraries were made after culturing for 5 days after the last passage.

EBs were prepared as follows. Confluent plates of undifferentiated hES cells were treated briefly with collagenase IV, and scraped to obtain small clusters of cells. Cell clusters were resuspended in 4 mL/well differentiation medium (KO DMEM containing 20% fetal bovine serum in place of 20% SR, and not preconditioned) on low adhesion 6-well plates (Costar). After 4 days in suspension, the contents of each well was transferred to individual wells pre-coated with gelatin. Each well was re-fed with 3 mL fresh differentiation medium every two days after replating. Cells were used for the preparation of cytoplasmic RNA on the eighth day after plating.

PreHEP cells were prepared based on the hepatocyte differentiation protocol described in WO 01/81549. Confluent wells of undifferentiated cells were prepared, and medium was changed to KO DMEM plus 20% SR+1% DMSO. The medium was changed every 24 h, and cells were used for preparation of cytoplasmic RNA on day 5 of DMSO treatment.

PreNEU cells were prepared based on the neural differentiation protocol described in WO 01/88104. hES cells of the H7 line (p29) were used to generate EBs as described above except that 10 µM all-trans RA was included in the differentiation medium. After 4 days in suspension, EBs were transferred to culture plate precoated with poly-L-lysine and laminin. After plating, the medium was changed to EPFI medium. Cells were used for the preparation of cytoplasmic RNA after 3 days of growth in EPFI.

Partial 5' end sequences (an expressed sequence tag, or EST) were determined by conventional means for independent clones derived from each cDNA library. Overlapping ESTs were assembled into conjoined sequences.

TABLE 1

| Non-redundant EST sequences | |
|---|---|
| Library | Number of ESTs |
| hESC | 37,081 |
| EB | 37,555 |
| preHEP | 35,611 |
| preNEU | 38,206 |
| Total | 148,453 |

All of the stem cell lines used for preparation of the expression libraries were originally isolated and initially propagated on mouse feeder cells. Accordingly, the libraries were analyzed to determine whether they were contaminated with murine retroviruses that had shed from the feeder cells and subsequently infected the stem cells. Three complete viral genomes were used in a BLAST search: Moloney murine leukemia virus, Friend murine leukemia virus, and murine type C retrovirus. No matches with a high score were found against any of the ESTs.

The sequences were then compared to the Unigene database of human genes. ESTs that were at least 98% identical, over a stretch of at least 150 nucleotides each, to a common reference sequence in Unigene, were assumed to be transcribed from the same gene, and placed into a common assembly. The complete set of 148,453 ESTs collapsed to a non-redundant set of 32,764 assemblies.

Example 2

Selection of Marker Genes Specific for Undifferentiated and Differentiated Cells Candidate markers were selected from a database based on the imputed level of gene expression. The frequency of ESTs for any particular gene correlates with the abundance of that mRNA in the cells used to generate the cDNA library.

Thus, a comparison of frequencies of ESTs among the libraries indicates the relative abundance of the associated mRNA in the different cell types.

Candidate molecular markers were selected from the expressed gene (EST) database from their greater abundance in undifferentiated hES cells, relative to differentiated hES cells. Genes were identified as having a differential expression pattern (being up- or down-regulated) during the differentiation process, if the count of ESTs sequenced in the undifferentiated cells was substantially different from the sum of ESTs in the three differentiated libraries.

Oct 3/4 (a POU domain-containing transcription factor) and telomerase reverse transcriptase (hTERT) are known to be expressed preferentially in undifferentiated hES cells (WO 01/51616). Other genes suitable for characterizing or manipulating the undifferentiated phenotype are those that are down-regulated upon differentiation with a significance of $p \leq 0.05$, as determined by the Fisher Exact Test (explained below). 193 genes were found to have 4-fold more ESTs in hES cells, relative to each of the three cell types. 532 genes were found that were 2-fold greater hES cells, with a confidence of over 95% as determined by the Fisher Exact Test, relative to the sum of ESTs of the three cell types (minimum of 4 ESTs in hES cells). The following markers are of particular interest:

TABLE 2

EST Frequency of Genes that are Down-regulated upon Differentiation of hES cells

| | | | EST counts | | | |
|---|---|---|---|---|---|---|
| Geron ID | GenBank ID | Name | ES | EB | preHEP | preNEU |
| GA_10902 | NM_024504 | Pr domain containing 14 (PRDM 14) | 12 | 1 | 0 | 0 |
| GA_11893 | NM_032805 | Hypothetical protein FLJ14549 | 25 | 0 | 0 | 0 |
| GA_12318 | NM_032447 | Fibrillin3 | 6 | 0 | 0 | 0 |
| GA_1322 | NM_000142 | Fibroblast growth factor receptor 3 precursor (FGFR-3) | 9 | 1 | 5 | 1 |
| GA_34679 | NM_002015 | Forkhead box o1a (FOXO1a) | 4 | 0 | 1 | 1 |
| GA_1470 | NM_003740 | potassium channel, subfamily K, member 5 (KCNK5), mRNA | 4 | 0 | 0 | 1 |
| GA_1674 | NM_002701 | Octamer-Binding Transcription Factor 3a (OCT-3A) (OCT-4) | 24 | 1 | 2 | 0 |
| GA_2024 | NM_003212 | Teratocarcinoma-derived growth factor 1 (CRIPTO) | 20 | 1 | 0 | 0 |
| GA_2149 | NM_003413 | Zic family member 3 (ZIC3) | 7 | 0 | 1 | 0 |
| GA_2334 | NM_000216 | Kallmann syndrome 1 sequence (KAL1) | 5 | 0 | 1 | 0 |
| GA_23552 | NM_152742 | hypothetical protein DKFZp547M109 (DKFZp547M109), mRNA | 6 | 0 | 1 | 2 |
| GA_2356 | NM_002851 | Protein tyrosine phosphatase, receptor-type, z polypeptide 1 (PTPRZ1), | 10 | 0 | 0 | 0 |
| GA_2357 | NM_001670 | Armadillo repeat protein deleted in velo-cardio-facial syndrome (ARVCF) | 6 | 0 | 0 | 0 |
| GA_23578 | BM454360 | AGENCOURT_6402318 NIH_MGC_85 Homo sapiens cDNA clone IMAGE: 5497491 5', mRNA sequence | 6 | 0 | 0 | 0 |
| GA_2367 | NM_003923 | Forkhead box H1 (FOXH1) | 5 | 0 | 0 | 0 |
| GA_2436 | NM_004329 | Bone morphogenetic protein receptor, type Ia (BMPR1A) (ALK-3) | 7 | 3 | 1 | 1 |
| GA_2442 | NM_004335 | Bone marrow stromal antigen 2 (BST-2) | 13 | 0 | 2 | 3 |
| GA_2945 | NM_005232 | Ephrin type-a receptor 1 (EPHA1) | 5 | 1 | 1 | 1 |
| GA_2962 | NM_005314 | Gastrin-releasing peptide receptor (GRP-R) | 4 | 0 | 0 | 0 |
| GA_2988 | NM_005397 | Podocalyxin-like (PODXL) | 59 | 23 | 5 | 8 |
| GA_3337 | NM_006159 | NELL2 (nel-like protein 2) | 5 | 3 | 2 | 0 |
| GA_3559 | NM_005629 | Solute carrier family 6, member 8 (SLC6A8) | 5 | 1 | 0 | 1 |
| GA_3898 | NM_006892 | DNA (cytosine-5-)-methyltransferase 3 beta (DNMT3B) | 49 | 2 | 3 | 1 |
| GA_5391 | NM_002968 | Sal-like 1 (SALL1), | 7 | 1 | 1 | 0 |
| GA_33680 | NM_016089 | Krab-zinc finger protein SZF1-1 | 15 | 0 | 1 | 0 |
| GA_36977 | NM_020927 | KIAA1576 protein | 9 | 2 | 1 | 0 |

TABLE 2-continued

EST Frequency of Genes that are Down-regulated upon Differentiation of hES cells

| Geron ID | GenBank ID | Name | EST counts | | | |
|---|---|---|---|---|---|---|
| | | | ES | EB | preHEP | preNEU |
| GA_8723 | NM_152333 | Homo sapiens chromosome 14 open reading frame 69 (C14orf69), mRNA | 14 | 1 | 1 | 3 |
| GA_9167 | AF308602 | Notch 1 (N1) | 6 | 2 | 1 | 0 |
| GA_9183 | NM_007129 | Homo sapiens Zic family member 2 (odd-paired homolog, Drosophila) (ZIC2), mRNA | 8 | 1 | 1 | 0 |
| GA_35037 | NM_004426 | Homo sapiens polyhomeotic-like 1 (Drosophila) (PHC1), mRNA | 34 | 9 | 5 | 4 |

Only one EST for hTERT was identified in undifferentiated hES cells and none were detected from the differentiated cells, which was not statistically significant. Thus, potentially useful markers that are expressed at low levels could have been omitted in this analysis, which required a minimum of four ESTs. It would be possible to identify such genes by using other techniques described elsewhere in this disclosure.

Three genes were observed from EST frequency queries that were of particular interest as potentially useful markers of hES cells. They were Teratocarcinoma-derived growth factor (Cripto), Podocalyxin-like (PODXL), and gastrin-releasing peptide receptor (GRPR). These genes were not only more abundant in undifferentiated cells, relative to differentiated hES cells, but also encoded for proteins expressed on the surface of cells. Surface markers have the added advantage that they could be easily detected with immunological reagents. ESTs for Cripto and GRPR were quite restricted to hES cells, with one or zero ESTs, respectively, scored in any of the differentiated cells. PODXL ESTs were detected in all 4-cell types, but substantially fewer (2.5×–12×) in differentiated cells. All three markers retained a detectable level of expression in differentiated cultures of hES cells. There may be a low level of expression of these markers in differentiated cells, or the expression detected may be due to a small proportion of undifferentiated cells in the population. GABA(A) receptor, Lefty B, Osteopontin, Thy-1 co-transcribed, and Solute carrier 21 are other significant markers of the undifferentiated phenotype.

By similar reasoning, genes that show a higher frequency of ESTs in differentiated cells can be used as specific markers for differentiation. ESTs that are 2-fold more abundant in the sum of all three differentiated cell types (EBs, preHEP and preNEU cells) and with a p-value$\leq$0.05 as determined by the Fisher Exact Test, compared with undifferentiated hES cells are candidate markers for differentiation down multiple pathways. ESTs that are relatively abundant in only one of the differentiated cell types are candidate markers for tissue-specific differentiation. The following markers are of particular interest:

TABLE 3

EST Frequency of Genes that are Upregulated upon Differentiation

| Geron ID | GenBank ID | Name | EST counts | | | |
|---|---|---|---|---|---|---|
| | | | ES | EB | preHEP | preNEU |
| GA_35463 | NM_024298 | Homo sapiens leukocyte receptor cluster (LRC) member 4 (LENG4), mRNA | 0 | 4 | 9 | 8 |
| GA_10492 | NM_006903 | Inorganic pyrophosphatase (PPASE) | 0 | 5 | 5 | 6 |
| GA_38563 | NM_021005 | Homo sapiens nuclear receptor subfamily 2, group F, member 2 (NR2F2), mRNA | 0 | 9 | 8 | 9 |
| GA_38570 | NM_001844 | Collagen, type II, alpha 1 (COL2A1), transcript variant 1 | | 15 | 31 | 5 |
| GA_1476 | NM_002276 | Keratin type I cytoskeletal 19 (cytokeratin 19) | 1 | 26 | 14 | 38 |
| GA_34776 | NM_002273 | Keratin type II cytoskeletal 8 (cytokeratin 8) (CK 8) | 9 | 71 | 144 | 156 |
| GA_1735 | NM_002806 | Homo sapiens proteasome (prosome, macropain) 26S subunit, ATPase, 6 (PSMC6), mRNA | 1 | 7 | 7 | 8 |
| GA_1843 | NM_000982 | 60s ribosomal protein l21 | 1 | 7 | 48 | 42 |
| GA_35369 | NM_003374 | Voltage-dependent anion-selective channel (VDAC-1) | 1 | 5 | 6 | 10 |
| GA_23117 | NM_004772 | P311 protein [Homo sapiens] | 1 | 5 | 7 | 6 |
| GA_2597 | NM_138610 | Homo sapiens H2A histone family, member Y (H2AFY), transcript variant 3, mRNA | 1 | 5 | 5 | 14 |
| GA_3283 | NM_004484 | Homo sapiens glypican 3 (GPC3), mRNA | 1 | 6 | 7 | 12 |
| GA_3530 | NM_002539 | Homo sapiens ornithine decarboxylase 1 (ODC1), mRNA | 1 | 10 | 8 | 9 |
| GA_4145 | NM_002480 | Protein phosphatase 1, regulatory(inhibitor) subunit 12A (PPP1R12A) | 1 | 6 | 6 | 6 |
| GA_5992 | NM_014899 | Homo sapiens Rho-related BTB domain containing 3 (RHOBTB3), mRNA | 0 | 10 | 7 | 13 |
| GA_6136 | NM_016368 | Homo sapiens myo-inositol 1-phosphate synthase A1 (ISYNA1), mRNA | 1 | 7 | 5 | 16 |

TABLE 3-continued

EST Frequency of Genes that are Upregulated upon Differentiation

| Geron ID | GenBank ID | Name | EST counts | | | |
|---|---|---|---|---|---|---|
| | | | ES | EB | preHEP | preNEU |
| GA_6165 | NM_015853 | Orf (LOC51035) | 1 | 5 | 9 | 5 |
| GA_6219 | NM_016139 | 16.7 Kd protein (LOC51142), | 1 | 5 | 13 | 14 |
| GA_723 | NM_005801 | Homo sapiens putative translation initiation factor (SUI1), mRNA | 1 | 14 | 15 | 19 |
| GA_9196 | NM_000404 | Homo sapiens galactosidase, beta 1 (GLB1), transcript variant 179423, mRNA | 0 | 6 | 10 | 7 |
| GA_9649 | NM_014604 | Tax interaction protein 1 (TIP-1) | 0 | 8 | 5 | 5 |

Example 3

Specificity of Expression Confirmed by Real-time PCR

To verify the expression patterns of particular genes of interest at the mRNA level, extracts of undifferentiated hES cells and their differentiated progeny were assayed by real-time PCR. Cells were cultured for 1 week with 0.5% dimethyl sulfoxide (DMSO) or 500 nM retinoic acid (RA). The samples were amplified using sequence-specific primers, and the rate of amplification was correlated with the expression level of each gene in the cell population.

Taqman™ RT-PCR was performed under the following conditions: 1×RT Master Mix (ABI), 300 nM for each primer, and 80 nM of probe, and 10 pg to 100 ng of total RNA in nuclease-free water. The reaction was conducted under default RT-PCR conditions of 48° C. hold for 30 min, 95° C. hold for 10 min, and 40 cycles of 95° C. at 15 sec and 60° C. hold for 1 min. RNA was isolated by a guanidinium isothiocyanate method (RNAeasy™ kit, Qiagen) according to manufacturer's instructions, and subsequently DNAse treated (DNAfree™ kit, Ambion). Gene-specific primers and probes were designed by PrimerExpress™ software (Ver. 1.5, ABI). Probe oligonucleotides were synthesized with the fluorescent indicators 6-carboxyfluorescein (FAM) and 6-carboxy-tetramethylrhodamine (TAMRA) at the 5' and 3' ends, respectively. Relative quantitation of gene expression between multiple samples was achieved by normalization against endogenous 18S ribosomal RNA (primer and probe from ABI) using the $\Delta\Delta C_T$ method of quantitation (ABI). Fold change in expression level was calculated as $2^{-\Delta\Delta C_T}$.

The table below shows the results of this analysis. Since the cells have been cultured in RA and DMSO for a short period, they are at the early stages of differentiation, and the difference in expression level is less dramatic than it would be after further differentiation. Of particular interest for following or modulating the differentiation process are markers that show modified expression within the first week of differentiation by more than 2-fold (*), 5-fold (), 10-fold (*), or 100-fold (****).

TABLE 4

Quantitative RT-PCR analysis of gene expression in hESC differentiation

| | Geron ID | GenBank ID | Name | Fold Change | |
|---|---|---|---|---|---|
| | | | | RA | DMSO |
| A. | GA_10902 | NM_024504 | Pr domain containing 14 (PRDM14)** | −1.9 | −8.3 |
| | GA_11893 | NM_032805 | Hypothetical protein FLJ14549*** | −2.3 | −10.0 |
| | GA_12318 | NM_032447 | Fibrillin3 | | |
| | GA_1322 | NM_000142 | Fibroblast growth factor receptor 3 precursor (FGFR-3)* | 1.5 | 2.3 |
| | GA_1329 | NM_002015 | Forkhead box o1a (foxo1a)* | −1.6 | −2.9 |
| | GA_1470 | NM_003740 | Potassium channel subfamily k member 5 (TASK-2) | −1.6 | 1.0 |
| | GA_1674 | NM_002701 | Octamer-binding transcription factor 3a (OCT-3A) (OCT-4)** | −3.7 | −7.7 |
| | GA_2024 | NM_003212 | Teratocarcinoma-derived growth factor 1 (CRIPTO)*** | −4.0 | −12.5 |
| | GA_2149 | NM_003413 | Zic family member 3 (ZIC3)** | −1.7 | −5.3 |
| | GA_2334 | NM_000216 | Kallmann syndrome 1 sequence (KAL1)* | −1.1 | −2.5 |
| | GA_23552 | BC027972 | Glypican-2 (cerebroglycan) | −1.5 | −1.2 |
| | GA_2356 | NM_002851 | Protein tyrosine phosphatase, receptor-type, z polypeptide 1 (PTPRZ1)* | −1.7 | −3.3 |
| | GA_2367 | NM_003923 | Forkhead box h1 (FOXH1)** | −1.8 | −5.6 |
| | GA_2436 | NM_004329 | Bone morphogenetic protein receptor, type Ia (BMPR1A) (ALK-3)* | −2.4 | −2.4 |
| | GA_2442 | NM_004335 | Bone marrow stromal antigen 2 (BST-2) | 1.1 | −1.9 |
| | GA_2945 | NM_005232 | Ephrin type-a receptor 1 (EPHA1) | −1.3 | −1.9 |
| | GA_2962 | NM_005314 | Gastrin-releasing peptide receptor (GRP-R)** | −6.3 | −9.1 |
| | GA_2988 | NM_005397 | Podocalyxin-like (PODXL)* | −2.6 | −4.3 |
| | GA_3337 | NM_006159 | Nell2 (NEL-like protein 2) | −1.3 | −1.3 |
| | GA_3559 | NM_005629 | Solute carrier family 6, member 8 (SLC6A8) | −1.1 | −1.1 |
| | GA_420 | X98834 | Zinc finger protein, HSAL2* | −1.4 | −2.8 |

TABLE 4-continued

Quantitative RT-PCR analysis of gene expression in hESC differentiation

|   | Geron ID | GenBank ID | Name | Fold Change RA | Fold Change DMSO |
|---|----------|------------|------|----|------|
|   | GA_5391 | NM_002968 | Sal-like 1 (SALL1), | 1.4 | −1.3 |
|   | GA_6402 | NM_016089 | Krab-zinc finger protein SZF1-1* | −1.8 | −3.1 |
|   | GA_9167 | AF308602 | Notch 1 (N1) | 1.3 | 1.0 |
|   | GA_9183 | AF193855 | Zinc finger protein of cerebellum ZIC2* | 1.0 | −2.9 |
|   | GA_9443 | NM_004426 | Early development regulator 1 (polyhomeotic 1 homolog) (EDR1)** | −1.8 | −5.6 |
| B. | GA_9384 | NM_020997 | Left-right determination, factor b (LEFTB)** | −16.7 | −25.0 |
|   | GA_12173 | BC010641 | Gamma-aminobutyric acid (GABA) A receptor, beta 3** | −2.8 | −5.6 |
|   | GA_10513 | NM_033209 | Thy-1 co-transcribed*** | −12.5 | −11.1 |
|   | GA_1831 | NM_002941 | Roundabout, axon guidance receptor, homolog 1 (ROBO1), | 1.1 | 1.0 |
|   | GA_2753 | NM_000582 | Secreted phosphoprotein 1 (osteopontin)*** | −3.8 | −10.0 |
|   | GA_32919 | NM_133259 | 130 kDa leucine-rich protein (LRP 130) | −1.9 | −1.9 |
|   | GA_28290 | AK055829 | FLJ31267 (acetylglucosaminyltransferase-like protein)* | −2.3 | −4.5 |
| C. | GA_28053 | T24677 | EST**** | <−100* | <−100* |
|   | GA_26303 | NM_138815 | Hypothetical protein BC018070*** | −3.2 | −10.0 |
|   | GA_2028 | NM_003219 | Telomerase reverse transcriptase (TERT)* | −2.1 | −2.3 |

Example 4

Selection of Markers for Monitoring ES Cell Differentiation

Genes that undergo up- or down-regulation in expression levels during differentiation are of interest for a variety of different commercial applications, as described earlier. This experiment provides an example in which certain genes were selected as a means to monitor the ability of culture conditions to maintain the undifferentiated cell phenotype—and hence, the pluripotent differentiation capability of the cells.

Particular genes were chosen from those identified as having differential expression patterns, because they are known or suspected of producing a protein gene product that is expressed at the cell surface, or is secreted. These attributes are helpful, because they allow the condition of the cells to be monitored easily either by antibody staining of the cell surface, or by immunoassay of the culture supernatant. Genes were chosen from the EST database (Groups 1), microarray analysis (Group 2), and other sources (Group 3).

TABLE 5

Additional Genes analyzed by real-time PCR

| Name | GenBank or ID No. |
|------|-------------------|
| Group 1 Bone marrow stromal antigen | NM_004335 |
| Podocalyxin-like | NM_005397 |
| Rat GPC/glypican-2 (cerebroglycan) | TA_5416486 |
| Potassium channel subfamily k member 5 (TASK-2) | NM_003740 |
| Notch 1 protein | AF308602 |
| Teratocarcinoma-derived growth factor 1 (Cripto) | NM_003212 |
| Nel 1 like/NELL2 (Nel-like protein 2) | NM_006159 |
| Gastrin releasing peptide receptor | NM_005314 |
| Bone morphogenetic protein receptor | NM_004329 |
| ABCG2- ABC transporter | AY017168 |
| Solute carrier family 6, member 8 (SLC6A8) | NM_005629 |
| hTERT | NM_003219 |
| Oct 3/4 octamer-binding transcription factor 3a (oct-3a) (oct-4) | NM_002701 |

TABLE 5-continued

Additional Genes analyzed by real-time PCR

| Name | GenBank or ID No. |
|------|-------------------|
| Group 2 Left-right determination factor b (LEFTB) | NM_020997 |
| Secreted phosphoprotein 1 (osteopontin) | NM_000582 |
| Gamma-aminobutyric acid (GABA) A receptor, beta 3 | NM_021912 |
| Roundabout, axon guidance receptor, homologue 1 (ROBO1), | NM_002941 |
| Glucagon receptor | NM_00160 |
| Leucine-rich PPR-motif hum 130 kDa hum130leu 130 kd Leu | M92439 |
| Thy-1 co-transcribed | NM_033209 |
| Solute carrier family 21 | NM_016354 |
| LY6H lymphocyte antigen 6 complex locus H | NM_002347 |
| Plexin (PLXNB3) | NM_005393 |
| ICAM | NM_000201 |
| Group 3 Rhodopsin | NM_000539 |
| Kallmann syndrome 1 sequence (KAL1) | NM_000216 |
| Armadillo repeat protein deleted in velo-cardio-facial syndrome (ARVCF) | NM_001670 |
| Ephrin type-a receptor 1 (EPHA1) | NM_005232 |

FIG. 1 shows the decrease in expression of the genes in Group I (Upper Panel) and Group II (Lower Panel) in H9 hES cells after culturing for 7 days with RA or DM. Gene expression of rhodopsin and ICAM was below the limit of detection in differentiated cells. KALL and EPHAL were not tested.

Besides hTERT and Oct 3/4, three other genes were selected as characteristic of the undifferentiated hES cell phenotype. They were Teratocarcinoma-derived growth factor (Cripto), Podocalyxin-like (PODXL), and gastrin-releasing peptide receptor (GRPR).

FIG. 2 compares the level of expression of these five genes in hES cells with fully differentiated cells: BJ fibroblasts, BJ fibroblasts transfected to express hTERT (BJ-5TA), and 293 (human embryonic kidney) cells. The level of all markers shown was at least 10-fold higher, and potentially more than $10^2$, $10^3$, $10^4$, $10^5$, or $10^6$-fold higher in pluripotent stem cells than fully differentiated cells. All five markers retained a detectable level of expression in differentiated cultures of hESC. It is not clear if there is lower level of expression of these markers in differentiated cells, or if the detectable expression derived from the undifferentiated cells in the population. The one exception observed in this experiment was the hTERT transgene, expressed at an elevated level as expected in the BJ-5TA cells.

High-level expression of Cripto, GRPR and PODXL in undifferentiated hES cells reveals interesting aspects of the biology of these cells. Cripto has been implicated in normal mammalian development and tumor growth. Cripto encodes a glycosylphosphoinositol anchored protein that contains an EGF repeat and a cysteine rich motif, which makes it a member of the EGF-CFC family. It has been demonstrated that Cripto serves as a co receptor for Nodal, which is essential for mesoderm and endoderm formation in vertebrate development (Yeo et al., Molecular Cell 7:949, 2001). The finding that Cripto is expressed preferentially on undifferentiated hESC suggests that Nodal is an important signaling molecule for stem cells, perhaps to promote survival and/or proliferation.

PODXL encodes for transmembrane sialoprotein that is physically linked to the cytoskeleton. PODXL is suspected to act as an inhibitor of cell-cell adhesion and has been implicated in the embryonic development of the kidney podocyte. The anti-adhesion properties of PODXL when expressed on undifferentiated hESC may be an important feature related to stem cell migration.

The receptor for gastrin releasing peptide (GRP) is a G-protein coupled receptor that mediates numerous biological effects of Bombesin-like peptides, including regulation of gut acid secretion and satiety. A critical role has also been established for GRP and GRPR in control growth of cultured cells and normal mammalian development. GRP and GRPR may be oncofetal antigens that act as morphogens in normal development and cancer.

Example 5

Use of Cell Markers to Modify ES Cell Culture Conditions

This example illustrates the utility of the differentially expressed genes identified according to this invention in the evaluation of culture environments suitable for maintaining pluripotent stem cells.

FIG. 3 show results of an experiment in which hES cells of the H1 line were maintained for multiple passages in different media. Medium conditioned with feeder cells provides factors effective to allow hES cells to proliferate in culture without differentiating. However, culturing in unconditioned medium leads to loss of the undifferentiated phenotype, with an increasing percentage of the cells showing decreased expression of CD9 (a marker for endothelial cells, fibroblasts, and certain progenitor cells), and the classic hES cell marker SSEA-4.

FIG. 4 illustrates the sensitivity of hTERT, Oct 3/4, Cripto, GRP receptor, and podocalyxin-like protein (measured by real-time PCR assay) as a means of determining the degree of differentiation of the cells. After 4 passages in unconditioned X-VIVO™ 10 medium containing 8 ng/mL bFGF, all 5 markers show expression that has been down-regulated by about 10-fold. After 8 passages, expression has decreased by $10^2$, $10^3$, or $10^4$-fold.

FIG. 5 shows results of an experiment in which the hES cell line H1 was grown on different feeder cell lines: mEF=mouse embryonic fibroblasts; hMSC=human mesenchymal stem cells; UtSMC=human uterine smooth muscle cells; WI-38=an established line of human lung fibroblasts. As monitored by RT-PCR assay of Cripto, Oct 3/4, and hTERT, at least under the conditions used in this experiment, the hMSC are better substitutes for mEF feeders than the other cell lines tested.

FIG. 6 shows results of an experiment in which different media were tested for their ability to promote growth of hES cells without differentiation. Expression of Podocalyxin-like protein, Cripto, GFP Receptor, and hTERT were measured by RT-PCR. The test media were not preconditioned, but supplemented with the growth factors as follows:

TABLE 6

Growth Conditions Tested for Marker Expression

| | |
|---|---|
| Standard conditions: | DMEM preconditioned with mEF + bFGF (8 ng/mL) |
| Condition 3 | X-VIVO ™ 10 + bFGF (8 ng/mL) |
| Condition 4 | X-VIVO ™ 10 + bFGF (40 ng/mL) |
| Condition 5 | X-VIVO ™ 10 + bFGF (40 ng/mL) + stem cell factor (SCF, 15 ng/mL) |
| Condition 6 | X-VIVO ™ 10 + bFGF (40 ng/mL) + Flt3 ligand (75 ng/mL) |
| Condition 7 | X-VIVO ™ 10 + bFGF (40 ng/mL) + LIF (100 ng/mL) |
| Condition 8 | QBSF ™-60 + bFGF (40 ng/mL) |

The results show that the markers selected to monitor the undifferentiated phenotype showed similar changes in each of these culture conditions. By all criteria, XVIVO 10™ supplemented according to Condition 6 was found to be suitable for culturing hES cells without having to be preconditioned. As shown on the right side, when cells were put back into standard conditioned medium after 8 passages in the test conditions, expression of all four markers returned essentially to original levels. This shows that alterations in expression profiles in media Conditions 4 to 8 are temporary and reversible—consistent with the cells retaining full pluripotency.

TABLE 7

SEQUENCE DATA
Sequences Listed in this Disclosure

| SEQ. ID NO: | Designation | Reference |
|---|---|---|
| 1 | hTERT mRNA sequence | GenBank Accession NM_003129 |
| 2 | hTERT protein sequence | GenBank Accession NM_003129 |
| 3 | Oct 3/4 mRNA sequence | GenBank Accession NM_002701 |
| 4 | Oct 3/4 protein sequence | GenBank Accession NM_002701 |
| 5 | Cripto mRNA sequence | GenBank Accession NM_003212 |
| 6 | Cripto protein sequence | GenBank Accession NM_003212 |
| 7 | podocalyxin-like protein mRNA sequence | GenBank Accession NM_005397 |
| 8 | podocalyxin-like protein amino acid sequence | GenBank Accession NM_005397 |
| 9 | GRP receptor mRNA sequence | GenBank Accession NM_005314 |
| 10 | GRP receptor proteins sequence | GenBank Accession NM_005314 |
| 11 to 81 | Primers & probes for real-time PCR assay | This disclosure |
| 82–100 | Human telomeric repeats | U.S. Pat. No. 5,583,016 |

```
SEQ. ID NO: 1
LOCUS         TERT                    4015 bp    mRNA    linear    PRI 31-OCT-2000
DEFINITION    Homo sapiens telomerase reverse transcriptase (TERT), mRNA.
ACCESSION     NM_003219
AUTHORS       Nakamura, T. M., Morin, G. B., Chapman, K. B., Weinrich, S. L.,
              Andrews, W. H., Lingner, J., Harley, C. B. and Cech, T. R.
TITLE         Telomerase catalytic subunit homologs from fission yeast and human
JOURNAL       Science 277 (5328), 955-959 (1997)
CDS           56 . . . 3454

SEQ. ID NO: 3
LOCUS         POU5F1                  1158 bp    mRNA    linear    PRI 31-OCT-2000
DEFINITION    Homo sapiens POU domain, class 5, transcription factor 1 (POU5F1),
              mRNA.
ACCESSION     NM_002701
AUTHORS       Takeda, J., Seino, S. and Bell ,G. I.
TITLE         Human Oct3 gene family: cDNA sequences, alternative splicing, gene
              organization, chromosomal location, and expression at low levels in
              adult tissues
JOURNAL       Nucleic Acids Res. 20 (17), 4613-4620 (1992)
CDS           102 . . . 899

SEQ. ID NO: 5
LOCUS         TDGF1                   2033 bp    mRNA    linear    PRI 05-NOV-2002
DEFINITION    Homo sapiens teratocarcinoma-derived growth factor 1 (TOGF1), mRNA.
ACCESSION     NM_003212
AUTHORS       Dono, R., Montuori, N., Rocchi, M., De Ponti-Zilli, L., Ciccodicola,
              A.
              and Persico, M. G.
TITLE         Isolation and characterization of the CRIPTO autosomal gene and its
              X-linked related sequence
JOURNAL       Am. J. Hum. Genet. 49 (3), 555-565 (1991)
CDS           248 . . . 814

SEQ. ID NO: 7
LOCUS         PODXL                   5869 bp    mRNA    linear    PRI 01-NOV-2000
DEFINITION    Homo sapiens podocalyxin-like (PODXL), mRNA.
ACCESSION     NM_005397
AUTHORS       Kershaw, D. B., Beck, S. G., Wharram, B. L., Wiggins, J. E., Goyal,
              M.,
              Thomas, P. E. and Wiggins, R. C.
TITLE         Molecular cloning and characterization of human podocalyxin-like
              protein. Orthologous relationship to rabbit PCLP1 and rat
              podocalyxin
JOURNAL       J. Biol. Chem. 272 (25), 15708-15714 (1997)
CDS           251 . . . 1837
```

-continued

SEQ. ID NO: 9
LOCUS      GRPR                    1726 bp    mRNA    linear   PRI 05-NOV-2002

DEFINITION  Homo sapiens gastrin-releasing peptide receptor (GRPR), mRNA.

ACCESSION   NM_005314

AUTHORS     Xiao, D., Wang, J., Hampton, L. L. and Weber, H. C.

TITLE       The human gastrin-releasing peptide receptor gene structure, its
            tissue expression and promoter JOURNAL     Gene 264 (1), 95-103 (2001)

CDS                  399 . . . 1553

| | |
|---|---|
| Bone Marrow Stromal antigen | |
| Forward primer: ACCTGCAACCACACTGTGATG | SEQ. ID NO: 11 |
| Probe: 6fam-CCCTAATGGCTTCCCTGGATGCAGA-tam | SEQ. ID NO: 12 |
| Reverse Primer: TTTCTTTTGTCCTTGGGCCTT | SEQ. ID NO: 13 |
| Podocalyxin-like | |
| Forward primer: GCTCGGCATATCAGTGAGATCA | SEQ. ID NO: 14 |
| Probe: 6fam-TCTCATCCGAAGCGCCCCCTG-tam | SEQ. ID NO: 15 |
| Reverse Primer: AGCTCGTCCTGAACCTCACAG | SEQ. ID NO: 16 |
| Rat GPC/glpican-2 (cerebroglycan) | |
| Forward primer: CTGGAAGAAATGTGGTCAGCG | SEQ. ID NO: 17 |
| Probe: 6fam-AGCGCTTAAGGTGCCGGTGTCTGAAG-tam | SEQ. ID NO: 18 |
| Reverse Primer: CATCAGAGCCTGGCTGCAG | SEQ. ID NO: 19 |
| Potassium channel subfamily k member 5 (TASK-2) | |
| Forward primer: ACCATCGGCTTCGGTGAC | SEQ. ID NO: 20 |
| Probe: 6fam-TGTGGCCGGTGTGAACCCCA-tam | SEQ. ID NO: 21 |
| Reverse Primer: TACAGGGCGTGGTAGTTGGC | SEQ. ID NO: 22 |
| Notch 1 protein | |
| Forward primer: TGAGAGCTTCTCCTGTGTCTGC | SEQ. ID NO: 23 |
| Probe: 6fam-CAAGGGCAGACCTGTGAGGTCGACA-tam | SEQ. ID NO: 24 |
| Reverse Primer: GGGCTCAGAACGCAGTCGT | SEQ. ID NO: 25 |
| Teratocarcinoma-derived growth factor 1 (Cripto) | |
| Forward primer: TGAGCACGATGTGGGCA | SEQ. ID NO: 26 |
| Probe: 6fam-AGAGAACTGTGGGTCTGTGCCCCATG-tam | SEQ. ID NO: 27 |
| Reverse Primer: TTCTTGGGCAGCCAGGTG | SEQ. ID NO: 28 |
| Nel 1 like/NELL2 (Nel-like protein 2) | |
| Forward primer: CTTAAGTCGGCTCTTGCGTATGT | SEQ. ID NO: 29 |
| Probe: 6fam-ATGGCAAATGCTGTAAGGAATGCAAATCG-tam | SEQ. ID NO: 30 |
| Reverse Primer: AAGTAGGTTCGTCCTTGAAATTGG | SEQ. ID NO: 31 |
| Gastrin releasing peptide receptor | |
| Forward primer: CCGTGGAAGGGAATATACATGTC | SEQ. ID NO: 32 |
| Probe: 6fam-AGAAGCAGATTGAATCCCGGAAGCGA-TAM | SEQ. ID NO: 33 |
| Reverse Primer: CACCAGCACTGTCTTGGCAA | SEQ. ID NO: 34 |
| Bone morphogenetic protein receptor | |
| Forward primer: CAGATTATTGGGAGCCTATTTGTTC | SEQ. ID NO: 35 |
| Probe: 6fam-TCATTTCTCGTGTTCAAGGACAGAATCTGGAT-tam | SEQ. ID NO: 36 |
| Reverse Primer: CATCCCAGTGCCATGAAGC | SEQ. ID NO: 31 |

-continued

ABC G2-ABC transporter
Forward primer: GGCCTCAGGAAGACTTATGT                            SEQ. ID NO: 38

Probe: SYBR Green Detection Method

Reverse Primer: AAGGAGGTGGTGTAGCTGAT                           SEQ. ID NO: 39

Solute carrier family 6, member B (SLC6A8)
Forward primer: CCGGCAGCAT CAATGTCTG                           SEQ. ID NO: 40

Probe: 6fam-TCAAAGGCCTGGGCTACGCCTCC-tam                        SEQ. ID NO: 41

Reverse Primer: GTGTTGCAGTAGAAGACGATCACC                       SEQ. ID NO: 42

Oct 3/4 octamer-binding trasncription factor 3a (oct3a) (oct-4)
Forward primer: GAAACCCACACTGCAGCAGA                           SEQ. ID NO: 43

Probe: 6fam-CAGCCACATCGCCCAGCAGC-TAM                           SEQ. ID NO: 44

Reverse Primer: CACATCCTTCTCGAGCCCA                            SEQ. ID NO: 45

Left-right determination factor b (LEFTB)
Forward primer: TGCCGCCAGGAGATGTACA                            SEQ. ID NO: 46

Probe: 6fam-TGGGCCGAGAACTGGGTGCTG-tam                          SEQ. ID NO: 47

Reverse Primer: TCATAAGCCAGGAAGCCCG                            SEQ. ID NO: 48

Secreted phosphoprotein 1 (osteopontin)
Forward primer: TTGCAGCCTTCTCAGCCAA                            SEQ. ID NO: 49

Probe: 6fam-CGCCGACCAAGGAAAACTCACTACCA-tam                     SEQ. ID NO: 50

Reverse Primer: GGAGGCAAAAGCAAATCACTG                          SEQ. ID NO: 51

Gamma-aminobutyric aci (GABA) A receptor, beta 3
Forward primer: CCGTCTGGTCTCGAGGAATG                           SEQ. ID NO: 52

Probe: 6fam-TCTTCGCCACAGGTGCCTATCCTCG-tam                      SEQ. ID NO: 53

Reverse Primer: TCAACCGAAAGCTCAGTGACA                          SEQ. ID NO: 54

Roundabout, axon guidance receptor, homologue 1 (ROBO1)
Forward primer: GAGAGGAGGCGAAGCTGTCA                           SEQ. ID NO: 55

Probe: 6fam-CAGTGGAGGGAGGCCTGGACTTCTC-tam                      SEQ. ID NO: 56

Reverse Primer: GCGGCAGGTTCACTGATGT                            SEQ. ID NO: 57

Glucagon receptor
Forward primer: CCACACAGACTACAAGTTCCGG                         SEQ. ID NO: 58

Probe: 6fam-TGGCCAAGTCCACGCTGACCCT-tam                         SEQ. ID NO: 59

Reverse Primer: CTTCGTGGACGCCCAGC                              SEQ. ID NO: 60

Leucine-rich PPR-motif hum 130kda hum 130kd leu
Forward primer: GCAGCAGACCCCTTCTAGGTTAG                        SEQ. ID NO: 61

Probe: 6fam-ACCCGTGTCATCCAGGCATTGGC-tam                        SEQ. ID NO: 62

Reverse Primer: TGAACTACTTCTATGTTTTCAACATCACC                  SEQ. ID NO: 63

Thy-1 co-transcribed
Forward primer: AGCCTCCAAGTCAGGTGGG                            SEQ. ID NO: 64

Probe: 6fam-CAGAGCTGCACAGGGTTTGGCCC-TAM                        SEQ. ID NO: 65

Reverse Primer: GGAGGAAGTGCCTCCCTTAGA                          SEQ. ID NO: 66

Solute carrier family 21
Forward primer: GCGTCACCTACCTGGATGAGA                          SEQ. ID NO: 67

Probe: 6fam-CCAGCTGCTCGCCCGTCTACATTG-tam                       SEQ. ID NO: 68

Reverse Primer: TGGCCGCTGTGTAGAAGATG                           SEQ. ID NO: 69

LY6H lymphocyte antigen 6 complex locus H
Forward primer: CGAATCACCGATCCCAGC                             SEQ. ID NO: 70

-continued

```
Probe: 6fam-CAGCAGGAAGGATCACTCGGTGAACAA-tam              SEQ. ID NO: 71

Reverse Primer: CGAAGTCACAGGAGGAGGCA                     SEQ. ID NO: 72

Plexin (PLXNB3)
Forward primer: GAGAAGGTGTTGGACCAAGTCTACA               SEQ. ID NO: 73

Probe: 6fam-CCTCAGTGCATGCCCTAGACCTTGAGTG-tam            SEQ. ID NO: 74

Reverse Primer: CTTCGTCCGATAGGGTCAGG                    SEQ. ID NO: 75

ICAM
Forward primer: ACTCCAGAACGGGTGGAACTG                   SEQ. ID NO: 76

Probe: 6fam-ACCCCTCCCCTCTTGGCAGCC-tam                   SEQ. ID NO: 77

Reverse Primer: CGTAGGGTAAGGTTCTTGCCC                   SEQ. ID NO: 78

Rhodopsin
Forward primer: CCGGCTGGTCCAGGTACAT                     SEQ. ID NO: 79

Probe: 6fam-CCGAGGGCCTGCAGTGCTCG-tam                    SEQ. ID NO: 80

Reverse Primer: TTGAGCGTGTAGTAGTCGATTCCA                SEQ. ID NO: 81
```

\* \* \* \* \* \* \* \* \* \*

The Subject Matter Provided in this Disclosure can be Modified as a Matter of Routine Optimization, Without Departing from the Spirit of the Invention, or the Scope of the Appended Claims.

The claimed invention is:

1. A method for assessing the differentiation of a population of human embryonic stem cells in vitro, comprising measuring the gastrin-releasing peptide (GRP) receptor expression level in the population of human embryonic stem cells; wherein a decrease in the GRP receptor expression level relative to the GRP receptor expression level measured in the population at an earlier time point indicates that the population is differentiating.

2. The method of claim 1, wherein the GRP receptor expression level is measured at the mRNA level.

3. The method of claim 2, wherein the GRP receptor expression level is measured at the mRNA level by PCR amplification.

4. The method of claim 1, wherein the GRP receptor expression level is measured at the protein level.

5. The method of claim 4, wherein the GRP receptor expression level is measured at the protein level by antibody assay.

6. The method of claim 1, wherein the GRP receptor expression level is measured using flow cytometry.

* * * * *

SEQUENCE LISTING

```
<160> NUMBER OF SEQ ID NOS: 100

<210> SEQ ID NO 1
<211> LENGTH: 4015
<212> TYPE: DNA
<213> ORGANISM: Homo sapiens
<220> FEATURE:
<221> NAME/KEY: CDS
<222> LOCATION: (56)..(3454)
<223> OTHER INFORMATION:

<400> SEQUENCE: 1
gcagcgctgc gtcctgctgc gcacgtggga agccctggcc ccggccaccc ccgcg atg       58
                                                              Met
                                                              1 ccg cgc gct ccc cgc tgc cga gcc gtg cgc tcc ctg ctg cgc agc cac      106
Pro Arg Ala Pro Arg Cys Arg Ala Val Arg Ser Leu Leu Arg Ser His
            5                  10                  15 tac cgc gag gtg ctg ccg ctg gcc acg ttc gtg cgg cgc ctg ggg ccc      154
Tyr Arg Glu Val Leu Pro Leu Ala Thr Phe Val Arg Arg Leu Gly Pro
        20                  25                  30 cag ggc tgg cgg ctg gtg cag cgc ggg gac ccg gcg gct ttc cgc gcg      202
Gln Gly Trp Arg Leu Val Gln Arg Gly Asp Pro Ala Ala Phe Arg Ala
    35                  40                  45 ctg gtg gcc cag tgc ctg gtg tgc gtg ccc tgg gac gca cgg ccg ccc      250
Leu Val Ala Gln Cys Leu Val Cys Val Pro Trp Asp Ala Arg Pro Pro
50                  55                  60                  65 ccc gcc gcc ccc tcc ttc cgc cag gtg tcc tgc ctg aag gag ctg gtg      298
Pro Ala Ala Pro Ser Phe Arg Gln Val Ser Cys Leu Lys Glu Leu Val
                70                  75                  80 gcc cga gtg ctg cag agg ctg tgc gag cgc ggc gcg aag aac gtg ctg      346
Ala Arg Val Leu Gln Arg Leu Cys Glu Arg Gly Ala Lys Asn Val Leu
            85                  90                  95
```

-continued

| | |
|---|---|
| gcc ttc ggc ttc gcg ctg ctg gac ggg gcc cgc ggg ggc ccc ccc gag<br>Ala Phe Gly Phe Ala Leu Leu Asp Gly Ala Arg Gly Gly Pro Pro Glu<br>100                            105                     110 | 394 |
| gcc ttc acc acc agc gtg cgc agc tac ctg ccc aac acg gtg acc gac<br>Ala Phe Thr Thr Ser Val Arg Ser Tyr Leu Pro Asn Thr Val Thr Asp<br>115                         120                         125 | 442 |
| gca ctg cgg ggg agc ggg gcg tgg ggg ctg ctg cgc cgc gtg ggc<br>Ala Leu Arg Gly Ser Gly Ala Trp Gly Leu Leu Arg Arg Val Gly<br>130                         135                     140                145 | 490 |
| gac gac gtg ctg gtt cac ctg ctg gca cgc tgc gcg ctc ttt gtg ctg<br>Asp Asp Val Leu Val His Leu Leu Ala Arg Cys Ala Leu Phe Val Leu<br>                150                     155                     160 | 538 |
| gtg gct ccc agc tgc gcc tac cag gtg tgc ggg ccg ccg ctg tac cag<br>Val Ala Pro Ser Cys Ala Tyr Gln Val Cys Gly Pro Pro Leu Tyr Gln<br>                165                     170                   175 | 586 |
| ctc ggc gct gcc act cag gcc cgg ccc cgc cac gct agt gga ccc<br>Leu Gly Ala Ala Thr Gln Ala Arg Pro Pro Pro His Ala Ser Gly Pro<br>180                         185                     190 | 634 |
| cga agg cgt ctg gga tgc gaa cgg gcc tgg aac cat agc gtc agg gag<br>Arg Arg Arg Leu Gly Cys Glu Arg Ala Trp Asn His Ser Val Arg Glu<br>195                         200                     205 | 682 |
| gcc ggg gtc ccc ctg ggc ctg cca gcc ccg ggt gcg agg agg cgc ggg<br>Ala Gly Val Pro Leu Gly Leu Pro Ala Pro Gly Ala Arg Arg Arg Gly<br>210                         215                     220                225 | 730 |
| ggc agt gcc agc cga agt ctg ccg ttg ccc aag agg ccc agg cgt ggc<br>Gly Ser Ala Ser Arg Ser Leu Pro Leu Pro Lys Arg Pro Arg Arg Gly<br>                230                     235                     240 | 778 |
| gct gcc cct gag ccg gag cgg acg ccc gtt ggg cag ggg tcc tgg gcc<br>Ala Ala Pro Glu Pro Glu Arg Thr Pro Val Gly Gln Gly Ser Trp Ala<br>245                         250                     255 | 826 |
| cac ccg ggc agg acg cgt gga ccg agt gac cgt ggt ttc tgt gtg gtg<br>His Pro Gly Arg Thr Arg Gly Pro Ser Asp Arg Gly Phe Cys Val Val<br>260                         265                     270 | 874 |
| tca cct gcc aga ccc gcc gaa gaa gcc acc tct ttg gag ggt gcg ctc<br>Ser Pro Ala Arg Pro Ala Glu Glu Ala Thr Ser Leu Glu Gly Ala Leu<br>275                         280                     285 | 922 |
| tct ggc acg cgc cac tcc cac cca tcc gtg ggc cgc cag cac cac gcg<br>Ser Gly Thr Arg His Ser His Pro Ser Val Gly Arg Gln His His Ala<br>290                         295                     300                305 | 970 |
| ggc ccc cca tcc aca tcg cgg cca cca cgt ccc tgg gac acg cct tgt<br>Gly Pro Pro Ser Thr Ser Arg Pro Pro Arg Pro Trp Asp Thr Pro Cys<br>                310                     315                     320 | 1018 |
| ccc ccg gtg tac gcc gag acc aag cac ttc ctc tac tcc tca ggc gac<br>Pro Pro Val Tyr Ala Glu Thr Lys His Phe Leu Tyr Ser Ser Gly Asp<br>                325                     330                   335 | 1066 |
| aag gag cag ctg cgg ccc tcc ttc cta ctc agc tct ctg agg ccc agc<br>Lys Glu Gln Leu Arg Pro Ser Phe Leu Leu Ser Ser Leu Arg Pro Ser<br>                340                     345                   350 | 1114 |
| ctg act ggc gct cgg agg ctc gtg gag acc atc ttt ctg ggt tcc agg<br>Leu Thr Gly Ala Arg Arg Leu Val Glu Thr Ile Phe Leu Gly Ser Arg<br>355                         360                     365 | 1162 |
| ccc tgg atg cca ggg act ccc cgc agg ttg ccc cgc ctg ccc cag cgc<br>Pro Trp Met Pro Gly Thr Pro Arg Arg Leu Pro Arg Leu Pro Gln Arg<br>370                         375                     380                385 | 1210 |
| tac tgg caa atg cgg ccc ctg ttt ctg gag ctg ctt ggg aac cac gcg<br>Tyr Trp Gln Met Arg Pro Leu Phe Leu Glu Leu Leu Gly Asn His Ala<br>                390                     395                   400 | 1258 |
| cag tgc ccc tac ggg gtg ctc ctc aag acg cac tgc ccg ctg cga gct<br>Gln Cys Pro Tyr Gly Val Leu Leu Lys Thr His Cys Pro Leu Arg Ala | 1306 |

-continued

```
            405                 410                 415
gcg gtc acc cca gca gcc ggt gtc tgt gcc cgg gag aag ccc cag ggc    1354
Ala Val Thr Pro Ala Ala Gly Val Cys Ala Arg Glu Lys Pro Gln Gly
            420                 425                 430 tct gtg gcg gcc ccc gag gag gag gac aca gac ccc cgt cgc ctg gtg    1402
Ser Val Ala Ala Pro Glu Glu Glu Asp Thr Asp Pro Arg Arg Leu Val
            435                 440                 445 cag ctg ctc cgc cag cac agc agc ccc tgg cag gtg tac ggc ttc gtg    1450
Gln Leu Leu Arg Gln His Ser Ser Pro Trp Gln Val Tyr Gly Phe Val
450                 455                 460                 465 cgg gcc tgc ctg cgc cgg ctg gtg ccc cca ggc ctc tgg ggc tcc agg    1498
Arg Ala Cys Leu Arg Arg Leu Val Pro Pro Gly Leu Trp Gly Ser Arg
                    470                 475                 480 cac aac gaa cgc cgc ttc ctc agg aac acc aag aag ttc atc tcc ctg    1546
His Asn Glu Arg Arg Phe Leu Arg Asn Thr Lys Lys Phe Ile Ser Leu
                        485                 490                 495 ggg aag cat gcc aag ctc tcg ctg cag gag ctg acg tgg aag atg agc    1594
Gly Lys His Ala Lys Leu Ser Leu Gln Glu Leu Thr Trp Lys Met Ser
                500                 505                 510 gtg cgg gac tgc gct tgg ctg cgc agg agc cca ggg gtt ggc tgt gtt    1642
Val Arg Asp Cys Ala Trp Leu Arg Arg Ser Pro Gly Val Gly Cys Val
515                 520                 525 ccg gcc gca gag cac cgt ctg cgt gag gag atc ctg gcc aag ttc ctg    1690
Pro Ala Ala Glu His Arg Leu Arg Glu Glu Ile Leu Ala Lys Phe Leu
530                 535                 540                 545 cac tgg ctg atg agt gtg tac gtc gtc gag ctg ctc agg tct ttc ttt    1738
His Trp Leu Met Ser Val Tyr Val Val Glu Leu Leu Arg Ser Phe Phe
                    550                 555                 560 tat gtc acg gag acc acg ttt caa aag aac agg ctc ttt ttc tac cgg    1786
Tyr Val Thr Glu Thr Thr Phe Gln Lys Asn Arg Leu Phe Phe Tyr Arg
                        565                 570                 575 aag agt gtc tgg agc aag ttg caa agc att gga atc aga cag cac ttg    1834
Lys Ser Val Trp Ser Lys Leu Gln Ser Ile Gly Ile Arg Gln His Leu
                580                 585                 590 aag agg gtg cag ctg cgg gag ctg tcg gaa gca gag gtc agg cag cat    1882
Lys Arg Val Gln Leu Arg Glu Leu Ser Glu Ala Glu Val Arg Gln His
595                 600                 605 cgg gaa gcc agg ccc gcc ctg ctg acg tcc aga ctc cgc ttc atc ccc    1930
Arg Glu Ala Arg Pro Ala Leu Leu Thr Ser Arg Leu Arg Phe Ile Pro
610                 615                 620                 625 aag cct gac ggg ctg cgg ccg att gtg aac atg gac tac gtc gtg gga    1978
Lys Pro Asp Gly Leu Arg Pro Ile Val Asn Met Asp Tyr Val Val Gly
                    630                 635                 640 gcc aga acg ttc cgc aga gaa aag agg gcc gag cgt ctc acc tcg agg    2026
Ala Arg Thr Phe Arg Arg Glu Lys Arg Ala Glu Arg Leu Thr Ser Arg
                        645                 650                 655 gtg aag gca ctg ttc agc gtg ctc aac tac gag cgg gcg cgg cgc ccc    2074
Val Lys Ala Leu Phe Ser Val Leu Asn Tyr Glu Arg Ala Arg Arg Pro
                660                 665                 670 ggc ctc ctg ggc gcc tct gtg ctg ggc ctg gac gat atc cac agg gcc    2122
Gly Leu Leu Gly Ala Ser Val Leu Gly Leu Asp Asp Ile His Arg Ala
675                 680                 685 tgg cgc acc ttc gtg ctg cgt gtg cgg gcc cag gac ccg ccg cct gag    2170
Trp Arg Thr Phe Val Leu Arg Val Arg Ala Gln Asp Pro Pro Pro Glu
690                 695                 700                 705 ctg tac ttt gtc aag gtg gat gtg acg ggc gcg tac gac acc atc ccc    2218
Leu Tyr Phe Val Lys Val Asp Val Thr Gly Ala Tyr Asp Thr Ile Pro
                    710                 715                 720 cag gac agg ctc acg gag gtc atc gcc agc atc atc aaa ccc cag aac    2266
```

-continued

```
                Gln Asp Arg Leu Thr Glu Val Ile Ala Ser Ile Ile Lys Pro Gln Asn
                            725                 730                 735 acg tac tgc gtg cgt cgg tat gcc gtg gtc cag aag gcc gcc cat ggg         2314
Thr Tyr Cys Val Arg Arg Tyr Ala Val Val Gln Lys Ala Ala His Gly
            740                 745                 750 cac gtc cgc aag gcc ttc aag agc cac gtc tct acc ttg aca gac ctc         2362
His Val Arg Lys Ala Phe Lys Ser His Val Ser Thr Leu Thr Asp Leu
        755                 760                 765 cag ccg tac atg cga cag ttc gtg gct cac ctg cag gag acc agc ccg         2410
Gln Pro Tyr Met Arg Gln Phe Val Ala His Leu Gln Glu Thr Ser Pro
770                 775                 780                 785 ctg agg gat gcc gtc gtc atc gag cag agc tcc tcc ctg aat gag gcc         2458
Leu Arg Asp Ala Val Val Ile Glu Gln Ser Ser Ser Leu Asn Glu Ala
                790                 795                 800 agc agt ggc ctc ttc gac gtc ttc cta cgc ttc atg tgc cac cac gcc         2506
Ser Ser Gly Leu Phe Asp Val Phe Leu Arg Phe Met Cys His His Ala
            805                 810                 815 gtg cgc atc agg ggc aag tcc tac gtc cag tgc cag ggg atc ccg cag         2554
Val Arg Ile Arg Gly Lys Ser Tyr Val Gln Cys Gln Gly Ile Pro Gln
        820                 825                 830 ggc tcc atc ctc tcc acg ctg ctc tgc agc ctg tgc tac ggc gac atg         2602
Gly Ser Ile Leu Ser Thr Leu Leu Cys Ser Leu Cys Tyr Gly Asp Met
835                 840                 845 gag aac aag ctg ttt gcg ggg att cgg cgg gac ggg ctg ctc ctg cgt         2650
Glu Asn Lys Leu Phe Ala Gly Ile Arg Arg Asp Gly Leu Leu Leu Arg
850                 855                 860                 865 ttg gtg gat gat ttc ttg ttg gtg aca cct cac ctc acc cac gcg aaa         2698
Leu Val Asp Asp Phe Leu Leu Val Thr Pro His Leu Thr His Ala Lys
                870                 875                 880 acc ttc ctc agg acc ctg gtc cga ggt gtc cct gag tat ggc tgc gtg         2746
Thr Phe Leu Arg Thr Leu Val Arg Gly Val Pro Glu Tyr Gly Cys Val
            885                 890                 895 gtg aac ttg cgg aag aca gtg gtg aac ttc cct gta gaa gac gag gcc         2794
Val Asn Leu Arg Lys Thr Val Val Asn Phe Pro Val Glu Asp Glu Ala
        900                 905                 910 ctg ggt ggc acg gct ttt gtt cag atg ccg gcc cac ggc cta ttc ccc         2842
Leu Gly Gly Thr Ala Phe Val Gln Met Pro Ala His Gly Leu Phe Pro
    915                 920                 925 tgg tgc ggc ctg ctg ctg gat acc cgg acc ctg gag gtg cag agc gac         2890
Trp Cys Gly Leu Leu Leu Asp Thr Arg Thr Leu Glu Val Gln Ser Asp
930                 935                 940                 945 tac tcc agc tat gcc cgg acc tcc atc aga gcc agt ctc acc ttc aac         2938
Tyr Ser Ser Tyr Ala Arg Thr Ser Ile Arg Ala Ser Leu Thr Phe Asn
                950                 955                 960 cgc ggc ttc aag gct ggg agg aac atg cgt cgc aaa ctc ttt ggg gtc         2986
Arg Gly Phe Lys Ala Gly Arg Asn Met Arg Arg Lys Leu Phe Gly Val
            965                 970                 975 ttg cgg ctg aag tgt cac agc ctg ttt ctg gat ttg cag gtg aac agc         3034
Leu Arg Leu Lys Cys His Ser Leu Phe Leu Asp Leu Gln Val Asn Ser
        980                 985                 990 ctc cag acg gtg tgc acc aac  atc tac aag atc ctc  ctg ctg cag gcg      3082
Leu Gln Thr Val Cys Thr Asn Ile Tyr Lys Ile Leu  Leu Leu Gln Ala
    995                 1000                1005 tac  agg ttt cac gca tgt  gtg ctg cag ctc cca  ttt cat cag caa         3127
Tyr Arg Phe His Ala Cys Val Leu Gln Leu Pro Phe His Gln Gln
1010                1015                1020 gtt  tgg aag aac ccc aca  ttt ttc ctg cgc gtc  atc tct gac acg         3172
Val Trp Lys Asn Pro Thr Phe Phe Leu Arg Val Ile Ser Asp Thr
1025                1030                1035
```

```
gcc tcc ctc tgc tac tcc atc ctg aaa gcc aag aac gca ggg atg      3217
Ala Ser Leu Cys Tyr Ser Ile Leu Lys Ala Lys Asn Ala Gly Met
1040                1045                1050 tcg ctg ggg gcc aag ggc gcc gcc ggc cct ctg ccc tcc gag gcc      3262
Ser Leu Gly Ala Lys Gly Ala Ala Gly Pro Leu Pro Ser Glu Ala
1055                1060                1065 gtg cag tgg ctg tgc cac caa gca ttc ctg ctc aag ctg act cga      3307
Val Gln Trp Leu Cys His Gln Ala Phe Leu Leu Lys Leu Thr Arg
1070                1075                1080 cac cgt gtc acc tac gtg cca ctc ctg ggg tca ctc agg aca gcc      3352
His Arg Val Thr Tyr Val Pro Leu Leu Gly Ser Leu Arg Thr Ala
1085                1090                1095 cag acg cag ctg agt cgg aag ctc ccg ggg acg acg ctg act gcc      3397
Gln Thr Gln Leu Ser Arg Lys Leu Pro Gly Thr Thr Leu Thr Ala
1100                1105                1110 ctg gag gcc gca gcc aac ccg gca ctg ccc tca gac ttc aag acc      3442
Leu Glu Ala Ala Ala Asn Pro Ala Leu Pro Ser Asp Phe Lys Thr
1115                1120                1125 atc ctg gac tga tggccaccg cccacagcca ggccgagagc agacaccagc       3494
Ile Leu Asp
1130 agccctgtca cgccgggctc tacgtcccag ggagggaggg gcggcccaca cccaggcccg  3554 caccgctggg agtctgaggc ctgagtgagt gtttggccga ggcctgcatg tccggctgaa  3614 ggctgagtgt ccggctgagg cctgagcgag tgtccagcca agggctgagt gtccagcaca  3674 cctgccgtct tcacttcccc acaggctggg gctcggctcc accccagggc cagcttttcc  3734 tcaccaggag cccggcttcc actccccaca taggaatagt ccatcccag attcgccatt   3794 gttcaccct cgccctgccc tcctttgcct tccaccccca ccatccaggt ggagaccctg   3854 agaaggaccc tgggagctct gggaatttgg agtgaccaaa ggtgtgccct gtacacaggc  3914 gaggaccctg cacctggatg ggggtccctg tgggtcaaat tgggggagg tgctgtggga   3974 gtaaaatact gaatatatga gttttcagt tttgaaaaaa a                      4015

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
```

-continued

|     |     |     |     |     |     |     |     |     |     |     |     |     |     |     |     |
|---|---|---|---|---|---|---|---|---|---|---|---|---|---|---|---|
|     |     |     | 130 |     |     |     | 135 |     |     |     | 140 |     |     |     |     |
| Gly | Asp | Asp | Val | Leu | Val | His | Leu | Leu | Ala | Arg | Cys | Ala | Leu | Phe | Val |
| 145 |     |     |     |     | 150 |     |     |     |     | 155 |     |     |     |     | 160 |
| Leu | Val | Ala | Pro | Ser | Cys | Ala | Tyr | Gln | Val | Cys | Gly | Pro | Pro | Leu | Tyr |
|     |     |     |     | 165 |     |     |     |     | 170 |     |     |     |     | 175 |     |
| Gln | Leu | Gly | Ala | Ala | Thr | Gln | Ala | Arg | Pro | Pro | His | Ala | Ser | Gly |     |
|     |     |     | 180 |     |     |     |     | 185 |     |     |     | 190 |     |     |     |
| Pro | Arg | Arg | Arg | Leu | Gly | Cys | Glu | Arg | Ala | Trp | Asn | His | Ser | Val | Arg |
|     |     | 195 |     |     |     |     | 200 |     |     |     |     | 205 |     |     |     |
| Glu | Ala | Gly | Val | Pro | Leu | Gly | Leu | Pro | Ala | Pro | Gly | Ala | Arg | Arg | Arg |
|     | 210 |     |     |     |     | 215 |     |     |     |     | 220 |     |     |     |     |
| Gly | Gly | Ser | Ala | Ser | Arg | Ser | Leu | Pro | Leu | Pro | Lys | Arg | Pro | Arg | Arg |
| 225 |     |     |     |     | 230 |     |     |     |     | 235 |     |     |     |     | 240 |
| Gly | Ala | Ala | Pro | Glu | Pro | Glu | Arg | Thr | Pro | Val | Gly | Gln | Gly | Ser | Trp |
|     |     |     |     | 245 |     |     |     |     | 250 |     |     |     |     | 255 |     |
| Ala | His | Pro | Gly | Arg | Thr | Arg | Gly | Pro | Ser | Asp | Arg | Gly | Phe | Cys | Val |
|     |     |     | 260 |     |     |     |     | 265 |     |     |     | 270 |     |     |     |
| Val | Ser | Pro | Ala | Arg | Pro | Ala | Glu | Glu | Ala | Thr | Ser | Leu | Glu | Gly | Ala |
|     | 275 |     |     |     |     | 280 |     |     |     |     | 285 |     |     |     |     |
| Leu | Ser | Gly | Thr | Arg | His | Ser | His | Pro | Ser | Val | Gly | Arg | Gln | His | His |
|     | 290 |     |     |     |     | 295 |     |     |     |     | 300 |     |     |     |     |
| Ala | Gly | Pro | Pro | Ser | Thr | Ser | Arg | Pro | Pro | Arg | Pro | Trp | Asp | Thr | Pro |
| 305 |     |     |     |     | 310 |     |     |     |     | 315 |     |     |     |     | 320 |
| Cys | Pro | Pro | Val | Tyr | Ala | Glu | Thr | Lys | His | Phe | Leu | Tyr | Ser | Ser | Gly |
|     |     |     |     | 325 |     |     |     |     | 330 |     |     |     |     | 335 |     |
| Asp | Lys | Glu | Gln | Leu | Arg | Pro | Ser | Phe | Leu | Leu | Ser | Ser | Leu | Arg | Pro |
|     |     |     | 340 |     |     |     |     | 345 |     |     |     | 350 |     |     |     |
| Ser | Leu | Thr | Gly | Ala | Arg | Arg | Leu | Val | Glu | Thr | Ile | Phe | Leu | Gly | Ser |
|     |     | 355 |     |     |     |     | 360 |     |     |     |     | 365 |     |     |     |
| Arg | Pro | Trp | Met | Pro | Gly | Thr | Pro | Arg | Arg | Leu | Pro | Arg | Leu | Pro | Gln |
|     | 370 |     |     |     |     | 375 |     |     |     |     | 380 |     |     |     |     |
| Arg | Tyr | Trp | Gln | Met | Arg | Pro | Leu | Phe | Leu | Glu | Leu | Leu | Gly | Asn | His |
| 385 |     |     |     |     | 390 |     |     |     |     | 395 |     |     |     |     | 400 |
| Ala | Gln | Cys | Pro | Tyr | Gly | Val | Leu | Leu | Lys | Thr | His | Cys | Pro | Leu | Arg |
|     |     |     |     | 405 |     |     |     |     | 410 |     |     |     |     | 415 |     |
| Ala | Ala | Val | Thr | Pro | Ala | Ala | Gly | Val | Cys | Ala | Arg | Glu | Lys | Pro | Gln |
|     |     |     | 420 |     |     |     |     | 425 |     |     |     | 430 |     |     |     |
| Gly | Ser | Val | Ala | Ala | Pro | Glu | Glu | Glu | Asp | Thr | Asp | Pro | Arg | Arg | Leu |
|     |     | 435 |     |     |     |     | 440 |     |     |     |     | 445 |     |     |     |
| Val | Gln | Leu | Leu | Arg | Gln | His | Ser | Ser | Pro | Trp | Gln | Val | Tyr | Gly | Phe |
|     | 450 |     |     |     |     | 455 |     |     |     |     | 460 |     |     |     |     |
| Val | Arg | Ala | Cys | Leu | Arg | Arg | Leu | Val | Pro | Pro | Gly | Leu | Trp | Gly | Ser |
| 465 |     |     |     |     | 470 |     |     |     |     | 475 |     |     |     |     | 480 |
| Arg | His | Asn | Glu | Arg | Arg | Phe | Leu | Arg | Asn | Thr | Lys | Lys | Phe | Ile | Ser |
|     |     |     |     | 485 |     |     |     |     | 490 |     |     |     |     | 495 |     |
| Leu | Gly | Lys | His | Ala | Lys | Leu | Ser | Leu | Gln | Glu | Leu | Thr | Trp | Lys | Met |
|     |     |     | 500 |     |     |     |     | 505 |     |     |     | 510 |     |     |     |
| Ser | Val | Arg | Asp | Cys | Ala | Trp | Leu | Arg | Arg | Ser | Pro | Gly | Val | Gly | Cys |
|     |     | 515 |     |     |     |     | 520 |     |     |     |     | 525 |     |     |     |
| Val | Pro | Ala | Ala | Glu | His | Arg | Leu | Arg | Glu | Glu | Ile | Leu | Ala | Lys | Phe |
|     | 530 |     |     |     |     | 535 |     |     |     |     | 540 |     |     |     |     |
| Leu | His | Trp | Leu | Met | Ser | Val | Tyr | Val | Val | Glu | Leu | Leu | Arg | Ser | Phe |
| 545 |     |     |     |     | 550 |     |     |     |     | 555 |     |     |     |     | 560 |

```
Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
        580                 585                 590

Leu Lys Arg Val Gln Leu Arg Glu Leu Ser Glu Ala Glu Val Arg Gln
    595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975
```

-continued

```
Val Leu Arg Leu Lys Cys His Ser Leu Phe Leu Asp Leu Gln Val Asn
            980                 985                 990

Ser Leu Gln Thr Val Cys Thr Asn  Ile Tyr Lys Ile Leu  Leu Leu Gln
        995                 1000                1005

Ala Tyr  Arg Phe His Ala Cys  Val Leu Gln Leu Pro  Phe His Gln
    1010                1015                1020

Gln Val  Trp Lys Asn Pro Thr  Phe Phe Leu Arg Val  Ile Ser Asp
    1025                1030                1035

Thr Ala  Ser Leu Cys Tyr Ser  Ile Leu Lys Ala Lys  Asn Ala Gly
    1040                1045                1050

Met Ser  Leu Gly Ala Lys Gly  Ala Ala Gly Pro Leu  Pro Ser Glu
    1055                1060                1065

Ala Val  Gln Trp Leu Cys His  Gln Ala Phe Leu Leu  Lys Leu Thr
    1070                1075                1080

Arg His  Arg Val Thr Tyr Val  Pro Leu Leu Gly Ser  Leu Arg Thr
    1085                1090                1095

Ala Gln  Thr Gln Leu Ser Arg  Lys Leu Pro Gly Thr  Thr Leu Thr
    1100                1105                1110

Ala Leu  Glu Ala Ala Ala Asn  Pro Ala Leu Pro Ser  Asp Phe Lys
    1115                1120                1125

Thr Ile  Leu Asp
    1130

<210> SEQ ID NO 3
<211> LENGTH: 1158
<212> TYPE: DNA
<213> ORGANISM: Homo sapiens
<220> FEATURE:
<221> NAME/KEY: CDS
<222> LOCATION: (102)..(899)
<223> OTHER INFORMATION:

<400> SEQUENCE: 3
gtagtccttt gttacatgca tgagtcagtg aacagggaat gggtgaatga catttgtggg      60
taggttattt ctagaagtta ggtgggcagc tcggaaggca g atg cac ttc tac aga    116
                                              Met His Phe Tyr Arg
                                                1               5 cta ttc ctt ggg gcc aca cgt agg ttc ttg aat ccc gaa tgg aaa ggg      164
Leu Phe Leu Gly Ala Thr Arg Arg Phe Leu Asn Pro Glu Trp Lys Gly
            10                  15                  20 gag att gat aac tgg tgt gtt tat gtt ctt aca agt ctt ctg cct ttt      212
Glu Ile Asp Asn Trp Cys Val Tyr Val Leu Thr Ser Leu Leu Pro Phe
        25                  30                  35 aaa atc cag tcc cag gac atc aaa gct ctg cag aaa gaa ctc gag caa      260
Lys Ile Gln Ser Gln Asp Ile Lys Ala Leu Gln Lys Glu Leu Glu Gln
    40                  45                  50 ttt gcc aag ctc ctg aag cag aag agg atc acc ctg gga tat aca cag      308
Phe Ala Lys Leu Leu Lys Gln Lys Arg Ile Thr Leu Gly Tyr Thr Gln
55                  60                  65 gcc gat gtg ggg ctc acc ctg ggg gtt cta ttt ggg aag gta ttc agc      356
Ala Asp Val Gly Leu Thr Leu Gly Val Leu Phe Gly Lys Val Phe Ser
70                  75                  80                  85 caa acg acc atc tgc cgc ttt gag gct ctg cag ctt agc ttc aag aac      404
Gln Thr Thr Ile Cys Arg Phe Glu Ala Leu Gln Leu Ser Phe Lys Asn
                90                  95                  100 atg tgt aag ctg cgg ccc ttg ctg cag aag tgg gtg gag gaa gct gac      452
Met Cys Lys Leu Arg Pro Leu Leu Gln Lys Trp Val Glu Glu Ala Asp
            105                 110                 115
```

-continued

```
aac aat gaa aat ctt cag gag ata tgc aaa gca gaa acc ctc gtg cag      500
Asn Asn Glu Asn Leu Gln Glu Ile Cys Lys Ala Glu Thr Leu Val Gln
            120                 125                 130 gcc cga aag aga aag cga acc agt atc gag aac cga gtg aga ggc aac      548
Ala Arg Lys Arg Lys Arg Thr Ser Ile Glu Asn Arg Val Arg Gly Asn
135                 140                 145 ctg gag aat ttg ttc ctg cag tgc ccg aaa ccc aca ctg cag cag atc      596
Leu Glu Asn Leu Phe Leu Gln Cys Pro Lys Pro Thr Leu Gln Gln Ile
150                 155                 160                 165 agc cac atc gcc cag cag ctt ggg ctc gag aag gat gtg gtc cga gtg      644
Ser His Ile Ala Gln Gln Leu Gly Leu Glu Lys Asp Val Val Arg Val
                170                 175                 180 tgg ttc tgt aac cgg cgc cag aag ggc aag cga tca agc agc gac tat      692
Trp Phe Cys Asn Arg Arg Gln Lys Gly Lys Arg Ser Ser Ser Asp Tyr
            185                 190                 195 gca caa cga gag gat ttt gag gct gct ggg tct cct ttc tca ggg gga      740
Ala Gln Arg Glu Asp Phe Glu Ala Ala Gly Ser Pro Phe Ser Gly Gly
        200                 205                 210 cca gtg tcc ttt cct ctg gcc cca ggg ccc att ttt ggt gcc cca ggc      788
Pro Val Ser Phe Pro Leu Ala Pro Gly Pro His Phe Gly Ala Pro Gly
215                 220                 225 tat ggg agc cct cac ttc act gca ctg tac tcc tcg gtc cct ttc cct      836
Tyr Gly Ser Pro His Phe Thr Ala Leu Tyr Ser Ser Val Pro Phe Pro
230                 235                 240                 245 gag ggg gaa gcc ttt ccc cct gtc tct gtc acc act ctg ggc tct ccc      884
Glu Gly Glu Ala Phe Pro Pro Val Ser Val Thr Thr Leu Gly Ser Pro
                250                 255                 260 ttg cat tca aac tga ggtgcctgcc tgcccttcta ggaatggggg acaggggag       939
Leu His Ser Asn
            265 gggaggagct agggaaagaa aacctggagt ttgtgccagg gttttggat taagttcttc     999 attcactaag gaaggaattg ggaacacaaa gggtggggc agggagttt ggggcaactg     1059 gttggaggga aggtgaagtt caatgatgct cttgatttta atcccacatc atgtatcact   1119 tttttcttaa ataaagaagc ttgggacaca gtagataga                          1158
```

<210> SEQ ID NO 4
<211> LENGTH: 265
<212> TYPE: PRT
<213> ORGANISM: Homo sapiens

<400> SEQUENCE: 4

```
Met His Phe Tyr Arg Leu Phe Leu Gly Ala Thr Arg Arg Phe Leu Asn
1               5                   10                  15

Pro Glu Trp Lys Gly Glu Ile Asp Asn Trp Cys Val Tyr Val Leu Thr
            20                  25                  30

Ser Leu Leu Pro Phe Lys Ile Gln Ser Gln Asp Ile Lys Ala Leu Gln
        35                  40                  45

Lys Glu Leu Glu Gln Phe Ala Lys Leu Leu Lys Gln Lys Arg Ile Thr
    50                  55                  60

Leu Gly Tyr Thr Gln Ala Asp Val Gly Leu Thr Leu Gly Val Leu Phe
65                  70                  75                  80

Gly Lys Val Phe Ser Gln Thr Thr Ile Cys Arg Phe Glu Ala Leu Gln
                85                  90                  95

Leu Ser Phe Lys Asn Met Cys Lys Leu Arg Pro Leu Leu Gln Lys Trp
            100                 105                 110

Val Glu Glu Ala Asp Asn Asn Glu Asn Leu Gln Glu Ile Cys Lys Ala
        115                 120                 125
```

-continued

```
Glu Thr Leu Val Gln Ala Arg Lys Arg Lys Arg Thr Ser Ile Glu Asn
            130                 135                 140

Arg Val Arg Gly Asn Leu Glu Asn Leu Phe Leu Gln Cys Pro Lys Pro
145                 150                 155                 160

Thr Leu Gln Gln Ile Ser His Ile Ala Gln Gln Leu Gly Leu Glu Lys
                165                 170                 175

Asp Val Val Arg Val Trp Phe Cys Asn Arg Arg Gln Lys Gly Lys Arg
            180                 185                 190

Ser Ser Ser Asp Tyr Ala Gln Arg Glu Asp Phe Glu Ala Ala Gly Ser
        195                 200                 205

Pro Phe Ser Gly Gly Pro Val Ser Phe Pro Leu Ala Pro Gly Pro His
    210                 215                 220

Phe Gly Ala Pro Gly Tyr Gly Ser Pro His Phe Thr Ala Leu Tyr Ser
225                 230                 235                 240

Ser Val Pro Phe Pro Glu Gly Glu Ala Phe Pro Pro Val Ser Val Thr
                245                 250                 255

Thr Leu Gly Ser Pro Leu His Ser Asn
            260                 265

<210> SEQ ID NO 5
<211> LENGTH: 2033
<212> TYPE: DNA
<213> ORGANISM: Homo sapiens
<220> FEATURE:
<221> NAME/KEY: CDS
<222> LOCATION: (248)..(814)
<223> OTHER INFORMATION:

<400> SEQUENCE: 5
ggagaatccc cggaaaggct gagtctccag ctcaaggtca aaacgtccaa ggccgaaagc      60
cctccagttt ccctggacg ccttgctcct gcttctgcta cgaccttctg gggaaaacga    120
atttctcatt ttcttcttaa attgccattt tcgctttagg agatgaatgt tttcctttgg    180
ctgttttggc aatgactctg aattaaagcg atgctaacgc ctcttttccc cctaattgtt    240 aaaagct atg gac tgc agg aag atg gcc cgc ttc tct tac agt gtg att       289
        Met Asp Cys Arg Lys Met Ala Arg Phe Ser Tyr Ser Val Ile
        1               5                   10 tgg atc atg gcc att tct aaa gtc ttt gaa ctg gga tta gtt gcc ggg       337
Trp Ile Met Ala Ile Ser Lys Val Phe Glu Leu Gly Leu Val Ala Gly
15                  20                  25                  30 ctg ggc cat cag gaa ttt gct cgt cca tct cgg gga tac ctg gcc ttc       385
Leu Gly His Gln Glu Phe Ala Arg Pro Ser Arg Gly Tyr Leu Ala Phe
                35                  40                  45 aga gat gac agc att tgg ccc cag gag gag cct gca att cgg cct cgg       433
Arg Asp Asp Ser Ile Trp Pro Gln Glu Glu Pro Ala Ile Arg Pro Arg
            50                  55                  60 tct tcc cag cgt gtg ccg ccc atg ggg ata cag cac agt aag gag cta       481
Ser Ser Gln Arg Val Pro Pro Met Gly Ile Gln His Ser Lys Glu Leu
        65                  70                  75 aac aga acc tgc tgc ctg aat ggg gga acc tgc atg ctg ggg tcc ttt       529
Asn Arg Thr Cys Cys Leu Asn Gly Gly Thr Cys Met Leu Gly Ser Phe
    80                  85                  90 tgt gcc tgc cct ccc tcc ttc tac gga cgg aac tgt gag cac gat gtg       577
Cys Ala Cys Pro Pro Ser Phe Tyr Gly Arg Asn Cys Glu His Asp Val
95                  100                 105                 110 cgc aaa gag aac tgt ggg tct gtg ccc cat gac acc tgg ctg ccc aag       625
Arg Lys Glu Asn Cys Gly Ser Val Pro His Asp Thr Trp Leu Pro Lys
                115                 120                 125
```

-continued

```
aag tgt tcc ctg tgt aaa tgc tgg cac ggt cag ctc cgc tgc ttt cct    673
Lys Cys Ser Leu Cys Lys Cys Trp His Gly Gln Leu Arg Cys Phe Pro
        130                 135                 140 cag gca ttt cta ccc ggc tgt gat ggc ctt gtg atg gat gag cac ctc    721
Gln Ala Phe Leu Pro Gly Cys Asp Gly Leu Val Met Asp Glu His Leu
    145                 150                 155 gtg gct tcc agg act cca gaa cta cca ccg tct gca cgt act acc act    769
Val Ala Ser Arg Thr Pro Glu Leu Pro Pro Ser Ala Arg Thr Thr Thr
160                 165                 170 ttt atg cta gtt ggc atc tgc ctt tct ata caa agc tac tat taa        814
Phe Met Leu Val Gly Ile Cys Leu Ser Ile Gln Ser Tyr Tyr
175                 180                 185 tcgacattga cctatttcca gaaatacaat tttagatatc atgcaaattt catgaccagt    874
aaaggctgct gctacaatgt cctaactgaa agatgatcat tgtagttgc cttaaaataa    934
tgaatacaat ttccaaaatg gtctctaaca tttccttaca gaactacttc ttacttcttt    994
gccctgccct ctcccaaaaa actacttctt ttttcaaaag aaagtcagcc atatctccat   1054
tgtgcctaag tccagtgttt cttttttttt tttttttga cggagtct cactctgtca    1114
cccaggctgg actgcaatga cgcgatcttg gttcactgca acctccgcat ccggggttca   1174
agccattctc ctgcctaagc ctcccaagta actgggatta caggcatgtg tcaccatgcc   1234
cagctaattt ttttgtattt tagtagagat ggggtttca ccatattggc cagtctggtc    1294
tcgaactctg accttgtgat ccatcgatca gcctctcgag tgctgagatt acacacgtga   1354
gcaactgtgc aaggcctggt gtttcttgat acatgtaatt ctaccaaggt cttcttaata   1414
tgttctttta aatgattgaa ttatatgttc agattattgg agactaattc taatgtggac   1474
cttagaatac agttttgagt agagttgatc aaaatcaatt aaaatagtct ctttaaaagg   1534
aaagaaaaca tctttaaggg gaggaaccag agtgctgaag gaatggaagt ccatctgcgt   1594
gtgtgcaggg agactgggta ggaaagagga agcaaataga agagagaggt tgaaaaacaa   1654
aatgggttac ttgattggtg attaggtggt ggtagagaag caagtaaaaa ggctaaatgg   1714
aagggcaagt ttccatcatc tatagaaagc tatataagac aagaactccc cttttttttcc   1774
caaaggcatt ataaaagaa tgaagcctcc ttagaaaaaa aattataccct caatgtcccc    1834
aacaagattg cttaataaat tgtgtttcct ccaagctatt caattctttt aactgttgta   1894
gaagacaaaa tgttcacaat atatttagtt gtaaaccaag tgatcaaact acatattgta    1954
aagcccattt ttaaaataca ttgtatatat gtgtatgcac agtaaaaatg gaaactatat   2014
tgacctaaaa aaaaaaaaa                                                2033
```

<210> SEQ ID NO 6
<211> LENGTH: 188
<212> TYPE: PRT
<213> ORGANISM: Homo sapiens

<400> SEQUENCE: 6

```
Met Asp Cys Arg Lys Met Ala Arg Phe Ser Tyr Ser Val Ile Trp Ile
1               5                   10                  15

Met Ala Ile Ser Lys Val Phe Glu Leu Gly Leu Val Ala Gly Leu Gly
            20                  25                  30

His Gln Glu Phe Ala Arg Pro Ser Arg Gly Tyr Leu Ala Phe Arg Asp
        35                  40                  45

Asp Ser Ile Trp Pro Gln Glu Glu Pro Ala Ile Arg Pro Arg Ser Ser
    50                  55                  60
```

-continued

```
Gln Arg Val Pro Pro Met Gly Ile Gln His Ser Lys Glu Leu Asn Arg
 65                  70                  75                  80

Thr Cys Cys Leu Asn Gly Gly Thr Cys Met Leu Gly Ser Phe Cys Ala
                 85                  90                  95

Cys Pro Pro Ser Phe Tyr Gly Arg Asn Cys Glu His Asp Val Arg Lys
            100                 105                 110

Glu Asn Cys Gly Ser Val Pro His Asp Thr Trp Leu Pro Lys Lys Cys
        115                 120                 125

Ser Leu Cys Lys Cys Trp His Gly Gln Leu Arg Cys Phe Pro Gln Ala
    130                 135                 140

Phe Leu Pro Gly Cys Asp Gly Leu Val Met Asp Glu His Leu Val Ala
145                 150                 155                 160

Ser Arg Thr Pro Glu Leu Pro Pro Ser Ala Arg Thr Thr Thr Phe Met
                165                 170                 175

Leu Val Gly Ile Cys Leu Ser Ile Gln Ser Tyr Tyr
            180                 185
```

<210> SEQ ID NO 7
<211> LENGTH: 5869
<212> TYPE: DNA
<213> ORGANISM: Homo sapiens
<220> FEATURE:
<221> NAME/KEY: CDS
<222> LOCATION: (251)..(1837)
<223> OTHER INFORMATION:

<400> SEQUENCE: 7

```
aaacgccgcc caggacgcag ccgccgccgc cgccgctcct ctgccactgg ctctgcgccc      60
cagcccggct ctgctgcagc ggcagggagg aagagccgcc gcagcgcgac tcgggagccc     120
cgggccacag cctggcctcc ggagccaccc acaggcctcc ccgggcggcg cccacgctcc     180
taccgcccgg acgcgcggat cctccgccgg caccgcagcc acctgctccc ggcccagagg     240
cgacgacacg atg cgc tgc gcg ctg gcg ctc tcg gcg ctg ctg cta ctg      289
            Met Arg Cys Ala Leu Ala Leu Ser Ala Leu Leu Leu Leu
             1               5                  10 ttg tca acg ccg ccg ctg ctg ccg tcg tcg ccg tcg ccg tcg ccg tcg      337
Leu Ser Thr Pro Pro Leu Leu Pro Ser Ser Pro Ser Pro Ser Pro Ser
     15                  20                  25 ccg tcg ccc tcc cag aat gca acc cag act act acg gac tca tct aac      385
Pro Ser Pro Ser Gln Asn Ala Thr Gln Thr Thr Thr Asp Ser Ser Asn
 30                  35                  40                  45 aaa aca gca ccg act cca gca tcc agt gtc acc atc atg gct aca gat      433
Lys Thr Ala Pro Thr Pro Ala Ser Ser Val Thr Ile Met Ala Thr Asp
                 50                  55                  60 aca gcc cag cag agc aca gtc ccc act tcc aag gcc aac gaa atc ttg      481
Thr Ala Gln Gln Ser Thr Val Pro Thr Ser Lys Ala Asn Glu Ile Leu
             65                  70                  75 gcc tcg gtc aag gcg acc acc ctt ggt gta tcc agt gac tca ccg ggg      529
Ala Ser Val Lys Ala Thr Thr Leu Gly Val Ser Ser Asp Ser Pro Gly
         80                  85                  90 act aca acc ctg gct cag caa gtc tca ggc cca gtc aac act acc gtg      577
Thr Thr Thr Leu Ala Gln Gln Val Ser Gly Pro Val Asn Thr Thr Val
     95                 100                 105 gct aga gga ggc ggc tca ggc aac cct act acc acc atc gag agc ccc      625
Ala Arg Gly Gly Gly Ser Gly Asn Pro Thr Thr Thr Ile Glu Ser Pro
110                 115                 120                 125 aag agc aca aaa agt gca gac acc act aca gtt gca acc tcc aca gcc      673
Lys Ser Thr Lys Ser Ala Asp Thr Thr Thr Val Ala Thr Ser Thr Ala
                130                 135                 140
```

-continued

```
aca gct aaa cct aac acc aca agc agc cag aat gga gca gaa gat aca       721
Thr Ala Lys Pro Asn Thr Thr Ser Ser Gln Asn Gly Ala Glu Asp Thr
            145                 150                 155 aca aac tct ggg ggg aaa agc agc cac agt gtg acc aca gac ctc aca       769
Thr Asn Ser Gly Gly Lys Ser Ser His Ser Val Thr Thr Asp Leu Thr
        160                 165                 170 tcc act aag gca gaa cat ctg acg acc cct cac cct aca agt cca ctt       817
Ser Thr Lys Ala Glu His Leu Thr Thr Pro His Pro Thr Ser Pro Leu
    175                 180                 185 agc ccc cga caa ccc act ttg acg cat cct gtg gcc acc cca aca agc       865
Ser Pro Arg Gln Pro Thr Leu Thr His Pro Val Ala Thr Pro Thr Ser
190                 195                 200                 205 tcg gga cat gac cat ctt atg aaa att tca agc agt tca agc act gtg       913
Ser Gly His Asp His Leu Met Lys Ile Ser Ser Ser Ser Thr Val
                210                 215                 220 gct atc cct ggc tac acc ttc aca agc ccg ggg atg acc acc acc cta       961
Ala Ile Pro Gly Tyr Thr Phe Thr Ser Pro Gly Met Thr Thr Thr Leu
            225                 230                 235 ccg tca tcg gtt atc tcg caa aga act caa cag acc tcc agt cag atg      1009
Pro Ser Ser Val Ile Ser Gln Arg Thr Gln Gln Thr Ser Ser Gln Met
        240                 245                 250 cca gcc agc tct acg gcc cct tcc tcc cag gag aca gtg cag ccc acg      1057
Pro Ala Ser Ser Thr Ala Pro Ser Ser Gln Glu Thr Val Gln Pro Thr
    255                 260                 265 agc ccg gca acg gca ttg aga aca cct acc ctg cca gag acc atg agc      1105
Ser Pro Ala Thr Ala Leu Arg Thr Pro Thr Leu Pro Glu Thr Met Ser
270                 275                 280                 285 tcc agc ccc aca gca gca tca act acc cac cga tac ccc aaa aca cct      1153
Ser Ser Pro Thr Ala Ala Ser Thr Thr His Arg Tyr Pro Lys Thr Pro
                290                 295                 300 tct ccc act gtg gct cat gag agt aac tgg gca aag tgt gag gat ctt      1201
Ser Pro Thr Val Ala His Glu Ser Asn Trp Ala Lys Cys Glu Asp Leu
            305                 310                 315 gag aca cag aca cag agt gag aag cag ctc gtc ctg aac ctc aca gga      1249
Glu Thr Gln Thr Gln Ser Glu Lys Gln Leu Val Leu Asn Leu Thr Gly
        320                 325                 330 aac acc ctc tgt gca ggg ggc gct tcg gat gag aaa ttg atc tca ctg      1297
Asn Thr Leu Cys Ala Gly Gly Ala Ser Asp Glu Lys Leu Ile Ser Leu
    335                 340                 345 ata tgc cga gca gtc aaa gcc acc ttc aac ccg gcc caa gat aag tgc      1345
Ile Cys Arg Ala Val Lys Ala Thr Phe Asn Pro Ala Gln Asp Lys Cys
350                 355                 360                 365 ggc ata cgg ctg gca tct gtt cca gga agt cag acc gtg gtc gtc aaa      1393
Gly Ile Arg Leu Ala Ser Val Pro Gly Ser Gln Thr Val Val Val Lys
                370                 375                 380 gaa atc act att cac act aag ctc cct gcc aag gat gtg tac gag cgg      1441
Glu Ile Thr Ile His Thr Lys Leu Pro Ala Lys Asp Val Tyr Glu Arg
            385                 390                 395 ctg aag gac aaa tgg gat gaa cta aag gag gca ggg gtc agt gac atg      1489
Leu Lys Asp Lys Trp Asp Glu Leu Lys Glu Ala Gly Val Ser Asp Met
        400                 405                 410 aag cta ggg gac cag ggg cca ccg gag gag gcc gag gac cgc ttc agc      1537
Lys Leu Gly Asp Gln Gly Pro Pro Glu Glu Ala Glu Asp Arg Phe Ser
    415                 420                 425 atg ccc ctc atc atc acc atc gtc tgc atg gcg tca ttc ctg ctc ctc      1585
Met Pro Leu Ile Ile Thr Ile Val Cys Met Ala Ser Phe Leu Leu Leu
430                 435                 440                 445 gtg gcg gcc ctc tat ggc tgc tgc cac cag cgc ctc tcc cag agg aag      1633
Val Ala Ala Leu Tyr Gly Cys Cys His Gln Arg Leu Ser Gln Arg Lys
```

-continued

|     |     |     | 450 |     |     |     | 455 |     |     |     | 460 |     |     |     |     |      |
|-----|-----|-----|-----|-----|-----|-----|-----|-----|-----|-----|-----|-----|-----|-----|-----|------|
| gac | cag | cag | cgg | cta | aca | gag | gag | ctg | cag | aca | gtg | gag | aat | ggt | tac | 1681 |
| Asp | Gln | Gln | Arg | Leu | Thr | Glu | Glu | Leu | Gln | Thr | Val | Glu | Asn | Gly | Tyr |      |
|     |     |     | 465 |     |     |     | 470 |     |     |     | 475 |     |     |     |     |      |

| cat | gac | aac | cca | aca | ctg | gaa | gtg | atg | gag | acc | tct | tct | gag | atg | cag | 1729 |
|-----|-----|-----|-----|-----|-----|-----|-----|-----|-----|-----|-----|-----|-----|-----|-----|------|
| His | Asp | Asn | Pro | Thr | Leu | Glu | Val | Met | Glu | Thr | Ser | Ser | Glu | Met | Gln |      |
|     |     |     | 480 |     |     |     | 485 |     |     |     | 490 |     |     |     |     |      |

| gag | aag | aag | gtg | gtc | agc | ctc | aac | ggg | gag | ctg | ggg | gac | agc | tgg | atc | 1777 |
|-----|-----|-----|-----|-----|-----|-----|-----|-----|-----|-----|-----|-----|-----|-----|-----|------|
| Glu | Lys | Lys | Val | Val | Ser | Leu | Asn | Gly | Glu | Leu | Gly | Asp | Ser | Trp | Ile |      |
|     | 495 |     |     |     |     | 500 |     |     |     |     | 505 |     |     |     |     |      |

| gtc | cct | ctg | gac | aac | ctg | acc | aag | gac | gac | ctg | gat | gag | gag | gaa | gac | 1825 |
|-----|-----|-----|-----|-----|-----|-----|-----|-----|-----|-----|-----|-----|-----|-----|-----|------|
| Val | Pro | Leu | Asp | Asn | Leu | Thr | Lys | Asp | Asp | Leu | Asp | Glu | Glu | Glu | Asp |      |
| 510 |     |     |     |     | 515 |     |     |     |     | 520 |     |     |     |     | 525 |      |

| aca his leu | cac | ctc | tag | tccggtctgc | cggtggcctc | cagcagcacc | acagagctcc | 1877 |
|------|------|------|------|------|------|------|------|------|
| Thr | His | Leu |     |     |     |     |     |     |

| agaccaacca | cccaagtgc | cgtttggatg | gggaagggaa | agactgggga | gggagagtga | 1937 |
| actccgaggg | gtgtcccctc | ccaatccccc | cagggcctta | attttccct | tttcaacctg | 1997 |
| aacaaatcac | attctgtcca | gattcctctt | gtaaaataac | ccactagtgc | ctgagctcag | 2057 |
| tgctgctgga | tgatgaggga | gatcaagaaa | agccacgta | agggacttta | tagatgaact | 2117 |
| agtggaatcc | cttcattctg | cagtgagatt | gccgagacct | gaagagggta | agtgacttgc | 2177 |
| ccaaggtcag | agccacttgg | tgacagagcc | aggatgagaa | caaagattcc | atttgcacca | 2237 |
| tgccacactg | ctgtgttcac | atgtgccttc | cgtccagagc | agtcccgggc | agggtgaaa | 2297 |
| ctccagcagg | tggctgggct | ggaaggagg | gcagggctac | atcctggctc | ggtgggatct | 2357 |
| gacgacctga | agtccagct | cccaagtttt | ccttctccta | ccccagcctc | gtgtacccat | 2417 |
| cttcccaccc | tctatgttct | tacccctccc | tacactcagt | gtttgttccc | acttactctg | 2477 |
| tcctggggcc | tctgggatta | gcacaggtta | ttcataacct | tgaaccccctt | gttctggatt | 2537 |
| cggattttct | cacatttgct | tcgtgagatg | ggggcttaac | ccacacaggt | ctccgtgcgt | 2597 |
| gaaccaggtc | tgcttagggg | acctgcgtgc | agtgaggag | agaagggac | actcgagtcc | 2657 |
| aggctggtat | ctcagggcag | ctgatgaggg | gtcagcagga | acactggccc | attgcccctg | 2717 |
| gcactccttg | cagaggccac | ccacgatctt | cttgggctt | ccatttccac | cagggactaa | 2777 |
| aatctgctgt | agctagtgag | agcagcgtgt | tccttttgtt | gttcactgct | cagctgatgg | 2837 |
| gagtgattcc | ctgagaccca | gtatgaaaga | gcagtggctg | caggagaggc | cttcccgggg | 2897 |
| cccccccatca | gcgatgtgtc | ttcagagaca | atccattaaa | gcagccagga | aggacaggct | 2957 |
| ttcccctgta | tatcatagga | aactcaggga | catttcaagt | tgctgagagt | tttgttatag | 3017 |
| ttgttttcta | acccagccct | ccactgccaa | aggccaaaag | ctcagacagt | tggcagacgt | 3077 |
| ccagttagct | catctcactc | actctgattc | tcctgtgcca | caggaaaaga | gggcctggaa | 3137 |
| agcgcagtgc | atgctgggtg | catgaagggc | agcctggggg | acagactgtt | gtgggaacgt | 3197 |
| cccactgtcc | tggcctggag | ctaggccttg | ctgttcctct | tctctgtgag | cctagtgggg | 3257 |
| ctgctgcggt | tctcttgcag | tttctggtgg | catctcaggg | gaacacaaaa | gctatgtcta | 3317 |
| ttccccaata | taggactttt | atgggctcgg | cagttagctg | ccatgtagaa | ggctcctaag | 3377 |
| cagtgggcat | ggtgaggttt | catctgattg | agaaggggga | atcctgtgtg | gaatgttgaa | 3437 |
| cttttcgccat | ggtctccatc | gttctgggcg | taaattcct | gggatcaagt | aggaaaatgg | 3497 |
| gcagaactgc | ttaggggaat | gaaattgcca | tttttcgggt | gaaacgccac | acctccaggg | 3557 |
| tcttaagagt | caggctccgg | ctgtagtagc | tctgatgaaa | taggctatcc | actcgggatg | 3617 |

-continued

```
gcttactttt taaaagggta gggggagggg ctggggaaga tctgtcctgc accatctgcc    3677
taattccttc ctcacagtct gtagccatct gatatcctag ggggaaaagg aaggccaggg    3737
gttcacatag gccccagcg agtttcccag gagttagagg gatgcgaggc taacaagttc    3797
caaaaacatc tgccccgatg ctctagtgtt tggaggtggg caggatggag aacagtgcct    3857
gtttggggga aaacaggaaa tcttgttagg cttgagtgag gtgtttgctt ccttcttgcc    3917
cagcgctggg ttctctccac ccagtaggtt ttctgttgtg gtcccgtggg agaggccaga    3977
ctggattatt cctcctttgc tgatcctggg tcacacttca ccagccaggg cttttgacgg    4037
agacagcaaa taggcctctg caaatcaatc aaaggctgca accctatggc ctcttggaga    4097
cagatgatga ctggcaagga ctagagagca ggagtgcctg gccaggtcgg tcctgactct    4157
cctgactctc catcgctctg tccaaggaga acccggagag gctctgggct gattcagagg    4217
ttactgcttt atattcgtcc aaactgtgtt agtctaggct taggacagct tcagaatctg    4277
acaccttgcc ttgctcttgc caccaggaca cctatgtcaa caggccaaac agccatgcat    4337
ctataaaggt catcatcttc tgccaccttt actgggttct aaatgctctc tgataattca    4397
gagagcattg gtctgggaa gaggtaagag gaacactaga agctcagcat gacttaaaca    4457
ggttgtagca aagacagttt atcatcaact ctttcagtgg taaactgtgg tttccccaag    4517
ctgcacagga ggccagaaac cacaagtatg atgactagga agcctactgt catgagagtg    4577
gggagacagg cagcaaagct tatgaaggag gtacagaata ttctttgcgt tgtaagacag    4637
aatacgggtt taatctagtc taggcrccag atttttttcc cgcttgataa ggaaagctag    4697
cagaaagttt atttaaacca cttcttgagc tttatctttt ttgacaatat actggagaaa    4757
ctttgaagaa caagttcaaa ctgatacata tacacatatt ttttgataa tgtaaataca    4817
gtgaccatgt taacctaccc tgcactgctt taagtgaaca tactttgaaa aagcattatg    4877
ttagctgagt gatggccaag tttttctct ggacaggaat gtaaatgtct tactggaaat    4937
gacaagtttt tgcttgattt tttttttaa acaaaaatg aaatataaca agacaaactt    4997
atgataaagt atttgtcttg tagatcaggt gttttgtttt gttttttaa ttttaaaatg    5057
caaccctgcc ccctccccag caaagtcaca gctccatttc agtaaaggtt ggagtcaata    5117
tgctctggtt ggcaggcaac cctgtagtca tggagaaagg tatttcaaga tctagtccaa    5177
tcttttttcta gagaaaaaga taatctgaag ctcacaaaga tgaagtgact tcctcaaaat    5237
cacatggttc aggacagaaa caagattaaa acctggatcc acagactgtg cgcctcagaa    5297
ggaataatcg gtaaattaag aattgctact cgaaggtgcc agaatgacac aaaggacaga    5357
attccttttcc cagttgttac cctagcaagg ctagggaggg catgaacaca aacataagaa    5417
ctggtcttct cacactttct ctgaatcatt taggtttaag atgtaagtga acaattcttt    5477
ctttctgcca agaaacaaag ttttggatga gctttatat atggaactta ctccaacagg    5537
actgagggac caaggaaaca tgatggggga ggcaagagag ggcaaagagt aaaactgtag    5597
catagctttt gtcacggtca ctagctgatc cctcaggtct gctgcaaaca cagcatggag    5657
gacacagatg actctttggt gttggtcttt ttgtctgcag tgaatgttca acagtttgcc    5717
caggaactgg gggatcatat atgtcttagt ggacagggt ctgaagtaca ctggaattta    5777
ctgagaaact tgtttgtaaa aactatagtt aataattatt gcattttctt acaaaaatat    5837
attttggaaa attgtatact gtcaattaaa gt                                 5869
```

<210> SEQ ID NO 8
<211> LENGTH: 528

```
<212> TYPE: PRT
<213> ORGANISM: Homo sapiens

<400> SEQUENCE: 8

Met Arg Cys Ala Leu Ala Leu Ser Ala Leu Leu Leu Leu Ser Thr
1               5                   10                  15

Pro Pro Leu Leu Pro Ser Ser Pro Ser Pro Ser Pro Ser Pro
            20                  25                  30

Ser Gln Asn Ala Thr Gln Thr Thr Asp Ser Ser Asn Lys Thr Ala
                35                  40                  45

Pro Thr Pro Ala Ser Ser Val Thr Ile Met Ala Thr Asp Thr Ala Gln
50                          55                  60

Gln Ser Thr Val Pro Thr Ser Lys Ala Asn Glu Ile Leu Ala Ser Val
65                      70                  75                  80

Lys Ala Thr Thr Leu Gly Val Ser Ser Asp Ser Pro Gly Thr Thr Thr
                85                  90                  95

Leu Ala Gln Gln Val Ser Gly Pro Val Asn Thr Thr Val Ala Arg Gly
                100                 105                 110

Gly Gly Ser Gly Asn Pro Thr Thr Thr Ile Glu Ser Pro Lys Ser Thr
            115                 120                 125

Lys Ser Ala Asp Thr Thr Thr Val Ala Thr Ser Thr Ala Thr Ala Lys
130                 135                 140

Pro Asn Thr Thr Ser Ser Gln Asn Gly Ala Glu Asp Thr Thr Asn Ser
145                 150                 155                 160

Gly Gly Lys Ser Ser His Ser Val Thr Thr Asp Leu Thr Ser Thr Lys
                165                 170                 175

Ala Glu His Leu Thr Thr Pro His Pro Thr Ser Pro Leu Ser Pro Arg
                180                 185                 190

Gln Pro Thr Leu Thr His Pro Val Ala Thr Pro Thr Ser Ser Gly His
                195                 200                 205

Asp His Leu Met Lys Ile Ser Ser Ser Ser Thr Val Ala Ile Pro
            210                 215                 220

Gly Tyr Thr Phe Thr Ser Pro Gly Met Thr Thr Thr Leu Pro Ser Ser
225                 230                 235                 240

Val Ile Ser Gln Arg Thr Gln Gln Thr Ser Ser Gln Met Pro Ala Ser
                245                 250                 255

Ser Thr Ala Pro Ser Ser Gln Glu Thr Val Gln Pro Thr Ser Pro Ala
            260                 265                 270

Thr Ala Leu Arg Thr Pro Thr Leu Pro Glu Thr Met Ser Ser Ser Pro
            275                 280                 285

Thr Ala Ala Ser Thr Thr His Arg Tyr Pro Lys Thr Pro Ser Pro Thr
            290                 295                 300

Val Ala His Glu Ser Asn Trp Ala Lys Cys Glu Asp Leu Glu Thr Gln
305                 310                 315                 320

Thr Gln Ser Glu Lys Gln Leu Val Leu Asn Leu Thr Gly Asn Thr Leu
                325                 330                 335

Cys Ala Gly Gly Ala Ser Asp Glu Lys Leu Ile Ser Leu Ile Cys Arg
                340                 345                 350

Ala Val Lys Ala Thr Phe Asn Pro Ala Gln Asp Lys Cys Gly Ile Arg
                355                 360                 365

Leu Ala Ser Val Pro Gly Ser Gln Thr Val Val Lys Glu Ile Thr
            370                 375                 380

Ile His Thr Lys Leu Pro Ala Lys Asp Val Tyr Glu Arg Leu Lys Asp
385                 390                 395                 400
```

```
Lys Trp Asp Glu Leu Lys Glu Ala Gly Val Ser Asp Met Lys Leu Gly
            405                 410                 415

Asp Gln Gly Pro Pro Glu Glu Ala Glu Asp Arg Phe Ser Met Pro Leu
            420                 425                 430

Ile Ile Thr Ile Val Cys Met Ala Ser Phe Leu Leu Leu Val Ala Ala
            435                 440                 445

Leu Tyr Gly Cys Cys His Gln Arg Leu Ser Gln Arg Lys Asp Gln Gln
        450                 455                 460

Arg Leu Thr Glu Glu Leu Gln Thr Val Glu Asn Gly Tyr His Asp Asn
465                 470                 475                 480

Pro Thr Leu Glu Val Met Glu Thr Ser Ser Glu Met Gln Glu Lys Lys
            485                 490                 495

Val Val Ser Leu Asn Gly Glu Leu Gly Asp Ser Trp Ile Val Pro Leu
            500                 505                 510

Asp Asn Leu Thr Lys Asp Asp Leu Asp Glu Glu Glu Asp Thr His Leu
            515                 520                 525

<210> SEQ ID NO 9
<211> LENGTH: 1726
<212> TYPE: DNA
<213> ORGANISM: Homo sapiens
<220> FEATURE:
<221> NAME/KEY: CDS
<222> LOCATION: (399)..(1553)
<223> OTHER INFORMATION:

<400> SEQUENCE: 9
ccagattcta aatatcagga aagacgctgt gggaaaatag caggccaaaa gttcttagta      60
aactgcagcc agggagactc agactagaat ggaggtagaa agaactgatg cagagtgggt     120
ttaattctaa gccttttgt ggctaagttt tgttgttgtt aacttattga atttagagtt      180
gtattgcact ggtcatgtga aagccagagc agcaccagtg tcaaaatagt gacagagagt     240
tttgaatacc atagttagta tatatgtact cagagtattt ttattaaaga aggcaaagag     300
cccggcatag atcttatctt catcttcact cggttgcaaa atcaatagtt aagaaatagc     360
atctaaggga acttttaggt gggaaaaaaa atctagag atg gct cta aat gac tgt    416
                                          Met Ala Leu Asn Asp Cys
                                           1               5 ttc ctt ctg aac ttg gag gtg gac cat ttc atg cac tgc aac atc tcc      464
Phe Leu Leu Asn Leu Glu Val Asp His Phe Met His Cys Asn Ile Ser
             10                  15                  20 agt cac agt gcg gat ctc ccc gtg aac gat gac tgg tcc cac ccg ggg      512
Ser His Ser Ala Asp Leu Pro Val Asn Asp Asp Trp Ser His Pro Gly
         25                  30                  35 atc ctc tat gtc atc cct gca gtt tat ggg gtt atc att ctg ata ggc      560
Ile Leu Tyr Val Ile Pro Ala Val Tyr Gly Val Ile Ile Leu Ile Gly
     40                  45                  50 ctc att ggc aac atc act ttg atc aag atc ttc tgt aca gtc aag tcc      608
Leu Ile Gly Asn Ile Thr Leu Ile Lys Ile Phe Cys Thr Val Lys Ser
55                  60                  65                  70 atg cga aac gtt cca aac ctg ttc att tcc agt ctg gct ttg gga gac      656
Met Arg Asn Val Pro Asn Leu Phe Ile Ser Ser Leu Ala Leu Gly Asp
                 75                  80                  85 ctg ctc ctc cta ata acg tgt gct cca gtg gat gcc agc agg tac ctg      704
Leu Leu Leu Leu Ile Thr Cys Ala Pro Val Asp Ala Ser Arg Tyr Leu
             90                  95                 100 gct gac aga tgg cta ttt ggc agg att ggc tgc aaa ctg atc ccc ttt      752
Ala Asp Arg Trp Leu Phe Gly Arg Ile Gly Cys Lys Leu Ile Pro Phe
```

-continued

```
                   105                 110                 115
ata cag ctt acc tct gtt ggg gtg tct gtc ttc aca ctc acg gcg ctc      800
Ile Gln Leu Thr Ser Val Gly Val Ser Val Phe Thr Leu Thr Ala Leu
    120                 125                 130 tcg gca gac aga tac aaa gcc att gtc cgg cca atg gat atc cag gcc      848
Ser Ala Asp Arg Tyr Lys Ala Ile Val Arg Pro Met Asp Ile Gln Ala
135                 140                 145                 150 tcc cat gcc ctg atg aag atc tgc ctc aaa gcc gcc ttt atc tgg atc      896
Ser His Ala Leu Met Lys Ile Cys Leu Lys Ala Ala Phe Ile Trp Ile
                155                 160                 165 atc tcc atg ctg ctg gcc att cca gag gcc gtg ttt tct gac ctc cat      944
Ile Ser Met Leu Leu Ala Ile Pro Glu Ala Val Phe Ser Asp Leu His
            170                 175                 180 ccc ttc cat gag gaa agc acc aac cag acc ttc att agc tgt gcc cca      992
Pro Phe His Glu Glu Ser Thr Asn Gln Thr Phe Ile Ser Cys Ala Pro
        185                 190                 195 tac cca cac tct aat gag ctt cac ccc aaa atc cat tct atg gct tcc     1040
Tyr Pro His Ser Asn Glu Leu His Pro Lys Ile His Ser Met Ala Ser
    200                 205                 210 ttt ctg gtc ttc tac gtc atc cca ctg tcg atc atc tct gtt tac tac     1088
Phe Leu Val Phe Tyr Val Ile Pro Leu Ser Ile Ile Ser Val Tyr Tyr
215                 220                 225                 230 tac ttc att gct aaa aat ctg atc cag agt gct tac aat ctt ccc gtg     1136
Tyr Phe Ile Ala Lys Asn Leu Ile Gln Ser Ala Tyr Asn Leu Pro Val
                235                 240                 245 gaa ggg aat ata cat gtc aag aag cag att gaa tcc cgg aag cga ctt     1184
Glu Gly Asn Ile His Val Lys Lys Gln Ile Glu Ser Arg Lys Arg Leu
            250                 255                 260 gcc aag aca gtg ctg gtg ttt gtg ggc ctg ttc gcc ttc tgc tgg ctc     1232
Ala Lys Thr Val Leu Val Phe Val Gly Leu Phe Ala Phe Cys Trp Leu
        265                 270                 275 ccc aat cat gtc atc tac ctg tac cgc tcc tac cac tac tct gag gtg     1280
Pro Asn His Val Ile Tyr Leu Tyr Arg Ser Tyr His Tyr Ser Glu Val
    280                 285                 290 gac acc tcc atg ctc cac ttt gtc acc agc atc tgt gcc cgc ctc ctg     1328
Asp Thr Ser Met Leu His Phe Val Thr Ser Ile Cys Ala Arg Leu Leu
295                 300                 305                 310 gcc ttc acc aac tcc tgc gtg aac ccc ttt gcc ctc tac ctg ctg agc     1376
Ala Phe Thr Asn Ser Cys Val Asn Pro Phe Ala Leu Tyr Leu Leu Ser
                315                 320                 325 aag agt ttc agg aaa cag ttc aac act cag ctg ctc tgt tgc cag cct     1424
Lys Ser Phe Arg Lys Gln Phe Asn Thr Gln Leu Leu Cys Cys Gln Pro
            330                 335                 340 ggc ctg atc atc cgg tct cac agc act gga agg agt aca acc tgc atg     1472
Gly Leu Ile Ile Arg Ser His Ser Thr Gly Arg Ser Thr Thr Cys Met
        345                 350                 355 acc tcc ctc aag agt acc aac ccc tcc gtg gcc acc ttt agc ctc atc     1520
Thr Ser Leu Lys Ser Thr Asn Pro Ser Val Ala Thr Phe Ser Leu Ile
    360                 365                 370 aat gga aac atc tgt cac gag cgg tat gtc tag attgacccct gattttgccc   1573
Asn Gly Asn Ile Cys His Glu Arg Tyr Val
375                 380 cctgagggac ggttttgctt tatggctaga caggaaccct tgcatccatt gttgtgtctg   1633
tgccctccaa agagccttca gaatgctcct gagtggtgta ggtgggggtg gggaggccca   1693
aatgatggat caccattata ttttgaaaga agc                                1726
```

<210> SEQ ID NO 10
<211> LENGTH: 384

<212> TYPE: PRT
<213> ORGANISM: Homo sapiens

<400> SEQUENCE: 10

```
Met Ala Leu Asn Asp Cys Phe Leu Leu Asn Leu Glu Val Asp His Phe
1               5                   10                  15

Met His Cys Asn Ile Ser Ser His Ser Ala Asp Leu Pro Val Asn Asp
            20                  25                  30

Asp Trp Ser His Pro Gly Ile Leu Tyr Val Ile Pro Ala Val Tyr Gly
        35                  40                  45

Val Ile Ile Leu Ile Gly Leu Ile Gly Asn Ile Thr Leu Ile Lys Ile
50                  55                  60

Phe Cys Thr Val Lys Ser Met Arg Asn Val Pro Asn Leu Phe Ile Ser
65                  70                  75                  80

Ser Leu Ala Leu Gly Asp Leu Leu Leu Ile Thr Cys Ala Pro Val
                85                  90                  95

Asp Ala Ser Arg Tyr Leu Ala Asp Arg Trp Leu Phe Gly Arg Ile Gly
                100                 105                 110

Cys Lys Leu Ile Pro Phe Ile Gln Leu Thr Ser Val Gly Val Ser Val
            115                 120                 125

Phe Thr Leu Thr Ala Leu Ser Ala Asp Arg Tyr Lys Ala Ile Val Arg
130                 135                 140

Pro Met Asp Ile Gln Ala Ser His Ala Leu Met Lys Ile Cys Leu Lys
145                 150                 155                 160

Ala Ala Phe Ile Trp Ile Ile Ser Met Leu Leu Ala Ile Pro Glu Ala
                165                 170                 175

Val Phe Ser Asp Leu His Pro Phe His Glu Glu Ser Thr Asn Gln Thr
            180                 185                 190

Phe Ile Ser Cys Ala Pro Tyr Pro His Ser Asn Glu Leu His Pro Lys
        195                 200                 205

Ile His Ser Met Ala Ser Phe Leu Val Phe Tyr Val Ile Pro Leu Ser
        210                 215                 220

Ile Ile Ser Val Tyr Tyr Tyr Phe Ile Ala Lys Asn Leu Ile Gln Ser
225                 230                 235                 240

Ala Tyr Asn Leu Pro Val Glu Gly Asn Ile His Val Lys Lys Gln Ile
                245                 250                 255

Glu Ser Arg Lys Arg Leu Ala Lys Thr Val Leu Val Phe Val Gly Leu
            260                 265                 270

Phe Ala Phe Cys Trp Leu Pro Asn His Val Ile Tyr Leu Tyr Arg Ser
        275                 280                 285

Tyr His Tyr Ser Glu Val Asp Thr Ser Met Leu His Phe Val Thr Ser
290                 295                 300

Ile Cys Ala Arg Leu Leu Ala Phe Thr Asn Ser Cys Val Asn Pro Phe
305                 310                 315                 320

Ala Leu Tyr Leu Leu Ser Lys Ser Phe Arg Lys Gln Phe Asn Thr Gln
                325                 330                 335

Leu Leu Cys Cys Gln Pro Gly Leu Ile Ile Arg Ser His Ser Thr Gly
            340                 345                 350

Arg Ser Thr Thr Cys Met Thr Ser Leu Lys Ser Thr Asn Pro Ser Val
        355                 360                 365

Ala Thr Phe Ser Leu Ile Asn Gly Asn Ile Cys His Glu Arg Tyr Val
        370                 375                 380
```

<210> SEQ ID NO 11

-continued

```
<211> LENGTH: 21
<212> TYPE: DNA
<213> ORGANISM: Homo sapiens

<400> SEQUENCE: 11
acctgcaacc acactgtgat g                                              21

<210> SEQ ID NO 12
<211> LENGTH: 25
<212> TYPE: DNA
<213> ORGANISM: Homo sapiens

<400> SEQUENCE: 12
ccctaatggc ttccctggat gcaga                                          25

<210> SEQ ID NO 13
<211> LENGTH: 21
<212> TYPE: DNA
<213> ORGANISM: Homo sapiens

<400> SEQUENCE: 13
tttcttttgt ccttgggcct t                                              21

<210> SEQ ID NO 14
<211> LENGTH: 22
<212> TYPE: DNA
<213> ORGANISM: Homo sapiens

<400> SEQUENCE: 14
gctcggcata tcagtgagat ca                                             22

<210> SEQ ID NO 15
<211> LENGTH: 21
<212> TYPE: DNA
<213> ORGANISM: Homo sapiens

<400> SEQUENCE: 15
tctcatccga agcgcccct g                                               21

<210> SEQ ID NO 16
<211> LENGTH: 21
<212> TYPE: DNA
<213> ORGANISM: Homo sapiens

<400> SEQUENCE: 16
agctcgtcct gaacctcaca g                                              21

<210> SEQ ID NO 17
<211> LENGTH: 21
<212> TYPE: DNA
<213> ORGANISM: Homo sapiens

<400> SEQUENCE: 17
ctggaagaaa tgtggtcagc g                                              21

<210> SEQ ID NO 18
<211> LENGTH: 26
<212> TYPE: DNA
<213> ORGANISM: Homo sapiens

<400> SEQUENCE: 18
agcgcttaag gtgccggtgt ctgaag                                         26
```

```
<210> SEQ ID NO 19
<211> LENGTH: 19
<212> TYPE: DNA
<213> ORGANISM: Homo sapiens

<400> SEQUENCE: 19
catcagagcc tggctgcag                                              19

<210> SEQ ID NO 20
<211> LENGTH: 18
<212> TYPE: DNA
<213> ORGANISM: Homo sapiens

<400> SEQUENCE: 20
accatcggct tcggtgac                                               18

<210> SEQ ID NO 21
<211> LENGTH: 20
<212> TYPE: DNA
<213> ORGANISM: Homo sapiens

<400> SEQUENCE: 21
tgtggccggt gtgaacccca                                             20

<210> SEQ ID NO 22
<211> LENGTH: 20
<212> TYPE: DNA
<213> ORGANISM: Homo sapiens

<400> SEQUENCE: 22
tacagggcgt ggtagttggc                                             20

<210> SEQ ID NO 23
<211> LENGTH: 22
<212> TYPE: DNA
<213> ORGANISM: Homo sapiens

<400> SEQUENCE: 23
tgagagcttc tcctgtgtct gc                                          22

<210> SEQ ID NO 24
<211> LENGTH: 25
<212> TYPE: DNA
<213> ORGANISM: Homo sapiens

<400> SEQUENCE: 24
caagggcaga cctgtgaggt cgaca                                       25

<210> SEQ ID NO 25
<211> LENGTH: 19
<212> TYPE: DNA
<213> ORGANISM: Homo sapiens

<400> SEQUENCE: 25
gggctcagaa cgcactcgt                                              19

<210> SEQ ID NO 26
<211> LENGTH: 17
<212> TYPE: DNA
<213> ORGANISM: Homo sapiens

<400> SEQUENCE: 26
tgagcacgat gtgcgca                                                17
```

```
<210> SEQ ID NO 27
<211> LENGTH: 26
<212> TYPE: DNA
<213> ORGANISM: Homo sapiens

<400> SEQUENCE: 27
agagaactgt gggtctgtgc cccatg                                          26

<210> SEQ ID NO 28
<211> LENGTH: 18
<212> TYPE: DNA
<213> ORGANISM: Homo sapiens

<400> SEQUENCE: 28
ttcttgggca gccaggtg                                                   18

<210> SEQ ID NO 29
<211> LENGTH: 23
<212> TYPE: DNA
<213> ORGANISM: Homo sapiens

<400> SEQUENCE: 29
cttaagtcgg ctcttgcgta tgt                                             23

<210> SEQ ID NO 30
<211> LENGTH: 29
<212> TYPE: DNA
<213> ORGANISM: Homo sapiens

<400> SEQUENCE: 30
atggcaaatg ctgtaaggaa tgcaaatcg                                       29

<210> SEQ ID NO 31
<211> LENGTH: 24
<212> TYPE: DNA
<213> ORGANISM: Homo sapiens

<400> SEQUENCE: 31
aagtaggttc gtccttgaaa ttgg                                            24

<210> SEQ ID NO 32
<211> LENGTH: 23
<212> TYPE: DNA
<213> ORGANISM: Homo sapiens

<400> SEQUENCE: 32
ccgtggaagg gaatatacat gtc                                             23

<210> SEQ ID NO 33
<211> LENGTH: 26
<212> TYPE: DNA
<213> ORGANISM: Homo sapiens

<400> SEQUENCE: 33
agaagcagat tgaatcccgg aagcga                                          26

<210> SEQ ID NO 34
<211> LENGTH: 20
<212> TYPE: DNA
<213> ORGANISM: Homo sapiens

<400> SEQUENCE: 34
caccagcact gtcttggcaa                                                 20
```

```
<210> SEQ ID NO 35
<211> LENGTH: 25
<212> TYPE: DNA
<213> ORGANISM: Homo sapiens

<400> SEQUENCE: 35
cagattattg ggagcctatt tgttc                                  25

<210> SEQ ID NO 36
<211> LENGTH: 32
<212> TYPE: DNA
<213> ORGANISM: Homo sapiens

<400> SEQUENCE: 36
tcatttctcg tgttcaagga cagaatctgg at                          32

<210> SEQ ID NO 37
<211> LENGTH: 19
<212> TYPE: DNA
<213> ORGANISM: Homo sapiens

<400> SEQUENCE: 37
catcccagtg ccatgaagc                                         19

<210> SEQ ID NO 38
<211> LENGTH: 20
<212> TYPE: DNA
<213> ORGANISM: Homo sapiens

<400> SEQUENCE: 38
ggcctcagga agacttatgt                                        20

<210> SEQ ID NO 39
<211> LENGTH: 20
<212> TYPE: DNA
<213> ORGANISM: Homo sapiens

<400> SEQUENCE: 39
aaggaggtgg tgtagctgat                                        20

<210> SEQ ID NO 40
<211> LENGTH: 19
<212> TYPE: DNA
<213> ORGANISM: Homo sapiens

<400> SEQUENCE: 40
ccggcagcat caatgtctg                                         19

<210> SEQ ID NO 41
<211> LENGTH: 23
<212> TYPE: DNA
<213> ORGANISM: Homo sapiens

<400> SEQUENCE: 41
tcaaaggcct gggctacgcc tcc                                    23

<210> SEQ ID NO 42
<211> LENGTH: 24
<212> TYPE: DNA
<213> ORGANISM: Homo sapiens

<400> SEQUENCE: 42
```

```
gtgttgcagt agaagacgat cacc                                    24
```

<210> SEQ ID NO 43
<211> LENGTH: 20
<212> TYPE: DNA
<213> ORGANISM: Homo sapiens

<400> SEQUENCE: 43

```
gaaacccaca ctgcagcaga                                         20
```

<210> SEQ ID NO 44
<211> LENGTH: 20
<212> TYPE: DNA
<213> ORGANISM: Homo sapiens

<400> SEQUENCE: 44

```
cagccacatc gcccagcagc                                         20
```

<210> SEQ ID NO 45
<211> LENGTH: 19
<212> TYPE: DNA
<213> ORGANISM: Homo sapiens

<400> SEQUENCE: 45

```
cacatccttc tcgagccca                                          19
```

<210> SEQ ID NO 46
<211> LENGTH: 19
<212> TYPE: DNA
<213> ORGANISM: Homo sapiens

<400> SEQUENCE: 46

```
tgccgccagg agatgtaca                                          19
```

<210> SEQ ID NO 47
<211> LENGTH: 21
<212> TYPE: DNA
<213> ORGANISM: Homo sapiens

<400> SEQUENCE: 47

```
tgggccgaga actgggtgct g                                       21
```

<210> SEQ ID NO 48
<211> LENGTH: 19
<212> TYPE: DNA
<213> ORGANISM: Homo sapiens

<400> SEQUENCE: 48

```
tcataagcca ggaagcccg                                          19
```

<210> SEQ ID NO 49
<211> LENGTH: 19
<212> TYPE: DNA
<213> ORGANISM: Homo sapiens

<400> SEQUENCE: 49

```
ttgcagcctt ctcagccaa                                          19
```

<210> SEQ ID NO 50
<211> LENGTH: 26
<212> TYPE: DNA
<213> ORGANISM: Homo sapiens

<400> SEQUENCE: 50

-continued

```
cgccgaccaa ggaaaactca ctacca                                          26

<210> SEQ ID NO 51
<211> LENGTH: 21
<212> TYPE: DNA
<213> ORGANISM: Homo sapiens

<400> SEQUENCE: 51
ggaggcaaaa gcaaatcact g                                               21

<210> SEQ ID NO 52
<211> LENGTH: 20
<212> TYPE: DNA
<213> ORGANISM: Homo sapiens

<400> SEQUENCE: 52
ccgtctggtc tcgaggaatg                                                 20

<210> SEQ ID NO 53
<211> LENGTH: 25
<212> TYPE: DNA
<213> ORGANISM: Homo sapiens

<400> SEQUENCE: 53
tcttcgccac aggtgcctat cctcg                                           25

<210> SEQ ID NO 54
<211> LENGTH: 21
<212> TYPE: DNA
<213> ORGANISM: Homo sapiens

<400> SEQUENCE: 54
tcaaccgaaa gctcagtgac a                                               21

<210> SEQ ID NO 55
<211> LENGTH: 20
<212> TYPE: DNA
<213> ORGANISM: Homo sapiens

<400> SEQUENCE: 55
gagaggaggc gaagctgtca                                                 20

<210> SEQ ID NO 56
<211> LENGTH: 25
<212> TYPE: DNA
<213> ORGANISM: Homo sapiens

<400> SEQUENCE: 56
cagtggaggg aggcctggac ttctc                                           25

<210> SEQ ID NO 57
<211> LENGTH: 19
<212> TYPE: DNA
<213> ORGANISM: Homo sapiens

<400> SEQUENCE: 57
gcggcaggtt cactgatgt                                                  19

<210> SEQ ID NO 58
<211> LENGTH: 22
<212> TYPE: DNA
<213> ORGANISM: Homo sapiens
```

-continued

```
<400> SEQUENCE: 58
ccacacagac tacaagttcc gg                                              22

<210> SEQ ID NO 59
<211> LENGTH: 22
<212> TYPE: DNA
<213> ORGANISM: Homo sapiens

<400> SEQUENCE: 59
tggccaagtc cacgctgacc ct                                              22

<210> SEQ ID NO 60
<211> LENGTH: 17
<212> TYPE: DNA
<213> ORGANISM: Homo sapiens

<400> SEQUENCE: 60
cttcgtggac gcccagc                                                    17

<210> SEQ ID NO 61
<211> LENGTH: 23
<212> TYPE: DNA
<213> ORGANISM: Homo sapiens

<400> SEQUENCE: 61
gcagcagacc ccttctaggt tag                                             23

<210> SEQ ID NO 62
<211> LENGTH: 23
<212> TYPE: DNA
<213> ORGANISM: Homo sapiens

<400> SEQUENCE: 62
acccgtgtca tccaggcatt ggc                                             23

<210> SEQ ID NO 63
<211> LENGTH: 29
<212> TYPE: DNA
<213> ORGANISM: Homo sapiens

<400> SEQUENCE: 63
tgaactactt ctatgttttc aacatcacc                                       29

<210> SEQ ID NO 64
<211> LENGTH: 19
<212> TYPE: DNA
<213> ORGANISM: Homo sapiens

<400> SEQUENCE: 64
agcctccaag tcaggtggg                                                  19

<210> SEQ ID NO 65
<211> LENGTH: 23
<212> TYPE: DNA
<213> ORGANISM: Homo sapiens

<400> SEQUENCE: 65
cagagctgca cagggtttgg ccc                                             23

<210> SEQ ID NO 66
<211> LENGTH: 21
<212> TYPE: DNA
<213> ORGANISM: Homo sapiens
```

```
<400> SEQUENCE: 66
ggaggaagtg cctcccttag a                                         21

<210> SEQ ID NO 67
<211> LENGTH: 21
<212> TYPE: DNA
<213> ORGANISM: Homo sapiens

<400> SEQUENCE: 67
gcgtcaccta cctggatgag a                                         21

<210> SEQ ID NO 68
<211> LENGTH: 24
<212> TYPE: DNA
<213> ORGANISM: Homo sapiens

<400> SEQUENCE: 68
ccagctgctc gcccgtctac attg                                      24

<210> SEQ ID NO 69
<211> LENGTH: 20
<212> TYPE: DNA
<213> ORGANISM: Homo sapiens

<400> SEQUENCE: 69
tggccgctgt gtagaagatg                                           20

<210> SEQ ID NO 70
<211> LENGTH: 18
<212> TYPE: DNA
<213> ORGANISM: Homo sapiens

<400> SEQUENCE: 70
cgaatcaccg atcccagc                                             18

<210> SEQ ID NO 71
<211> LENGTH: 27
<212> TYPE: DNA
<213> ORGANISM: Homo sapiens

<400> SEQUENCE: 71
cagcaggaag gatcactcgg tgaacaa                                   27

<210> SEQ ID NO 72
<211> LENGTH: 20
<212> TYPE: DNA
<213> ORGANISM: Homo sapiens

<400> SEQUENCE: 72
cgaagtcaca ggaggaggca                                           20

<210> SEQ ID NO 73
<211> LENGTH: 25
<212> TYPE: DNA
<213> ORGANISM: Homo sapiens

<400> SEQUENCE: 73
gagaaggtgt tggaccaagt ctaca                                     25

<210> SEQ ID NO 74
<211> LENGTH: 28
<212> TYPE: DNA
```

<213> ORGANISM: Homo sapiens

<400> SEQUENCE: 74
cctcagtgca tgccctagac cttgagtg                28

<210> SEQ ID NO 75
<211> LENGTH: 20
<212> TYPE: DNA
<213> ORGANISM: Homo sapiens

<400> SEQUENCE: 75
cttcgtccga tagggtcagg                20

<210> SEQ ID NO 76
<211> LENGTH: 21
<212> TYPE: DNA
<213> ORGANISM: Homo sapiens

<400> SEQUENCE: 76
actccagaac gggtggaact g                21

<210> SEQ ID NO 77
<211> LENGTH: 21
<212> TYPE: DNA
<213> ORGANISM: Homo sapiens

<400> SEQUENCE: 77
acccctcccc tcttggcagc c                21

<210> SEQ ID NO 78
<211> LENGTH: 21
<212> TYPE: DNA
<213> ORGANISM: Homo sapiens

<400> SEQUENCE: 78
cgtagggtaa ggttcttgcc c                21

<210> SEQ ID NO 79
<211> LENGTH: 19
<212> TYPE: DNA
<213> ORGANISM: Homo sapiens

<400> SEQUENCE: 79
ccggctggtc caggtacat                19

<210> SEQ ID NO 80
<211> LENGTH: 20
<212> TYPE: DNA
<213> ORGANISM: Homo sapiens

<400> SEQUENCE: 80
ccgagggcct gcagtgctcg                20

<210> SEQ ID NO 81
<211> LENGTH: 24
<212> TYPE: DNA
<213> ORGANISM: Homo sapiens

<400> SEQUENCE: 81
ttgagcgtgt agtagtcgat tcca                24

<210> SEQ ID NO 82
<211> LENGTH: 24

```
<212> TYPE: DNA
<213> ORGANISM: Homo sapiens

<400> SEQUENCE: 82
ttagggttag ggttagggtt aggg                                             24

<210> SEQ ID NO 83
<211> LENGTH: 24
<212> TYPE: DNA
<213> ORGANISM: Homo sapiens

<400> SEQUENCE: 83
ttagggttag ggttagggtt aggg                                             24

<210> SEQ ID NO 84
<211> LENGTH: 24
<212> TYPE: DNA
<213> ORGANISM: Homo sapiens

<400> SEQUENCE: 84
ttagggttag ggttagggtt aggg                                             24

<210> SEQ ID NO 85
<211> LENGTH: 24
<212> TYPE: DNA
<213> ORGANISM: Homo sapiens

<400> SEQUENCE: 85
ttagggttag ggttagggtt aggg                                             24

<210> SEQ ID NO 86
<211> LENGTH: 24
<212> TYPE: DNA
<213> ORGANISM: Homo sapiens

<400> SEQUENCE: 86
ttagggttag ggttagggtt aggg                                             24

<210> SEQ ID NO 87
<211> LENGTH: 24
<212> TYPE: DNA
<213> ORGANISM: Homo sapiens

<400> SEQUENCE: 87
ttagggttag ggttagggtt aggg                                             24

<210> SEQ ID NO 88
<211> LENGTH: 24
<212> TYPE: DNA
<213> ORGANISM: Homo sapiens

<400> SEQUENCE: 88
ttagggttag ggttagggtt aggg                                             24

<210> SEQ ID NO 89
<211> LENGTH: 24
<212> TYPE: DNA
<213> ORGANISM: Homo sapiens

<400> SEQUENCE: 89
ttagggttag ggttagggtt aggg                                             24

<210> SEQ ID NO 90
```

```
<211> LENGTH: 24
<212> TYPE: DNA
<213> ORGANISM: Homo sapiens

<400> SEQUENCE: 90
ttagggttag ggttagggtt aggg                                              24

<210> SEQ ID NO 91
<211> LENGTH: 24
<212> TYPE: DNA
<213> ORGANISM: Homo sapiens

<400> SEQUENCE: 91
ttagggttag ggttagggtt aggg                                              24

<210> SEQ ID NO 92
<211> LENGTH: 24
<212> TYPE: DNA
<213> ORGANISM: Homo sapiens

<400> SEQUENCE: 92
ttagggttag ggttagggtt aggg                                              24

<210> SEQ ID NO 93
<211> LENGTH: 24
<212> TYPE: DNA
<213> ORGANISM: Homo sapiens

<400> SEQUENCE: 93
ttagggttag ggttagggtt aggg                                              24

<210> SEQ ID NO 94
<211> LENGTH: 24
<212> TYPE: DNA
<213> ORGANISM: Homo sapiens

<400> SEQUENCE: 94
ttagggttag ggttagggtt aggg                                              24

<210> SEQ ID NO 95
<211> LENGTH: 24
<212> TYPE: DNA
<213> ORGANISM: Homo sapiens

<400> SEQUENCE: 95
ttagggttag ggttagggtt aggg                                              24

<210> SEQ ID NO 96
<211> LENGTH: 24
<212> TYPE: DNA
<213> ORGANISM: Homo sapiens

<400> SEQUENCE: 96
ttagggttag ggttagggtt aggg                                              24

<210> SEQ ID NO 97
<211> LENGTH: 24
<212> TYPE: DNA
<213> ORGANISM: Homo sapiens

<400> SEQUENCE: 97
ttagggttag ggttagggtt aggg                                              24
```

-continued

```
<210> SEQ ID NO 98
<211> LENGTH: 24
<212> TYPE: DNA
<213> ORGANISM: Homo sapiens

<400> SEQUENCE: 98
ttagggttag ggttagggtt aggg                                              24

<210> SEQ ID NO 99
<211> LENGTH: 24
<212> TYPE: DNA
<213> ORGANISM: Homo sapiens

<400> SEQUENCE: 99
ttagggttag ggttagggtt aggg                                              24

<210> SEQ ID NO 100
<211> LENGTH: 24
<212> TYPE: DNA
<213> ORGANISM: Homo sapiens

<400> SEQUENCE: 100
ttagggttag ggttagggtt aggg                                              24
```